(12) United States Patent
Norita et al.

(10) Patent No.: US 7,492,398 B1
(45) Date of Patent: Feb. 17, 2009

(54) THREE-DIMENSIONAL INPUT APPARATUS AND IMAGE SENSING CONTROL METHOD

(75) Inventors: Toshio Norita, Osaka (JP); Kazuchika Sato, Kobe (JP); Hiroyuki Okada, Izumi (JP); Makoto Miyazaki, Ibaraki (JP); Koichi Kamon, Takatsuki (JP)

(73) Assignee: Minolta Co., Ltd, Osaka (JP)

( * ) Notice: Subject to any disclaimer, the term of this patent is extended or adjusted under 35 U.S.C. 154(b) by 0 days.

(21) Appl. No.: 09/405,848

(22) Filed: Sep. 27, 1999

(30) Foreign Application Priority Data

| Sep. 29, 1998 | (JP) | 10-274636 |
| Sep. 29, 1998 | (JP) | 10-274637 |
| Sep. 29, 1998 | (JP) | 10-274639 |
| Mar. 25, 1999 | (JP) | 11-081055 |

(51) Int. Cl.
H04N 3/14 (2006.01)
H04N 5/335 (2006.01)

(52) U.S. Cl. .................................................. 348/294

(58) Field of Classification Search .................. 348/296, 348/297, 302, 308, 309, 310, 294, 208.13; 358/520; 600/160; 356/376, 3.03, 3.04, 356/3.06, 485, 35, 357

See application file for complete search history.

(56) References Cited

U.S. PATENT DOCUMENTS

| 4,621,191 A | * | 11/1986 | Suzuki et al. .............. 250/201.7 |
| 5,083,150 A | * | 1/1992 | Nagasaki et al. ............... 396/49 |
| 5,182,658 A | * | 1/1993 | Ishizaki et al. ............... 358/483 |
| 5,589,909 A | * | 12/1996 | Kusaka ........................ 396/96 |
| 5,668,631 A | | 9/1997 | Norita et al. |
| 5,812,269 A | * | 9/1998 | Svetkoff et al. .............. 356/602 |
| 5,883,668 A | * | 3/1999 | Kazama et al. .............. 348/303 |
| 5,955,725 A | * | 9/1999 | Cattorini .................. 250/208.1 |
| 5,969,820 A | * | 10/1999 | Yoshii et al. ................. 356/623 |
| 6,248,133 B1 | * | 6/2001 | Komobuchi et al. ......... 348/315 |
| 6,503,195 B1 | * | 1/2003 | Keller et al. ................. 600/160 |

(Continued)

FOREIGN PATENT DOCUMENTS

JP 05-022670 1/1993

(Continued)

OTHER PUBLICATIONS

Japanese Office Action, issued in corresponding Japanese Patent Application No. JP 11-081055, dated on Jul. 7, 2007.

Primary Examiner—Yogesh Aggarwal
(74) Attorney, Agent, or Firm—McDermott Will & Emery LLP

(57) ABSTRACT

A three-dimensional input apparatus for generating data specifying the shape of an object by receiving the light from the object is disclosed. The detection light is irradiated toward the object by a projector so as to scan a virtual surface. An image sensing device detects the light reflected from the object. A controller thins out data and outputs it to the image sensing device in a direction corresponding to the main scanning direction of the virtual surface of the image sensing device. The controller also controls the image sensing device such that the light-receiving signal is repeatedly read on a line along the direction of movement of the received detection light in an effective area constituting a part of the image sensing surface thereby to read the light-receiving signal in the effective area.

5 Claims, 43 Drawing Sheets

U.S. PATENT DOCUMENTS 7,301,563 B1 * 11/2007 Kakinuma et al. ..... 348/208.13

FOREIGN PATENT DOCUMENTS

| JP | 7-174536 | 7/1995 |
| JP | 09-145319 | 6/1997 |
| JP | 9-287926 | 11/1997 |
| JP | 9-325019 | 12/1997 |
| JP | 10-68613 | 3/1998 |
| JP | 10-116334 | 5/1998 |
| JP | 10-173978 | 6/1998 |

* cited by examiner

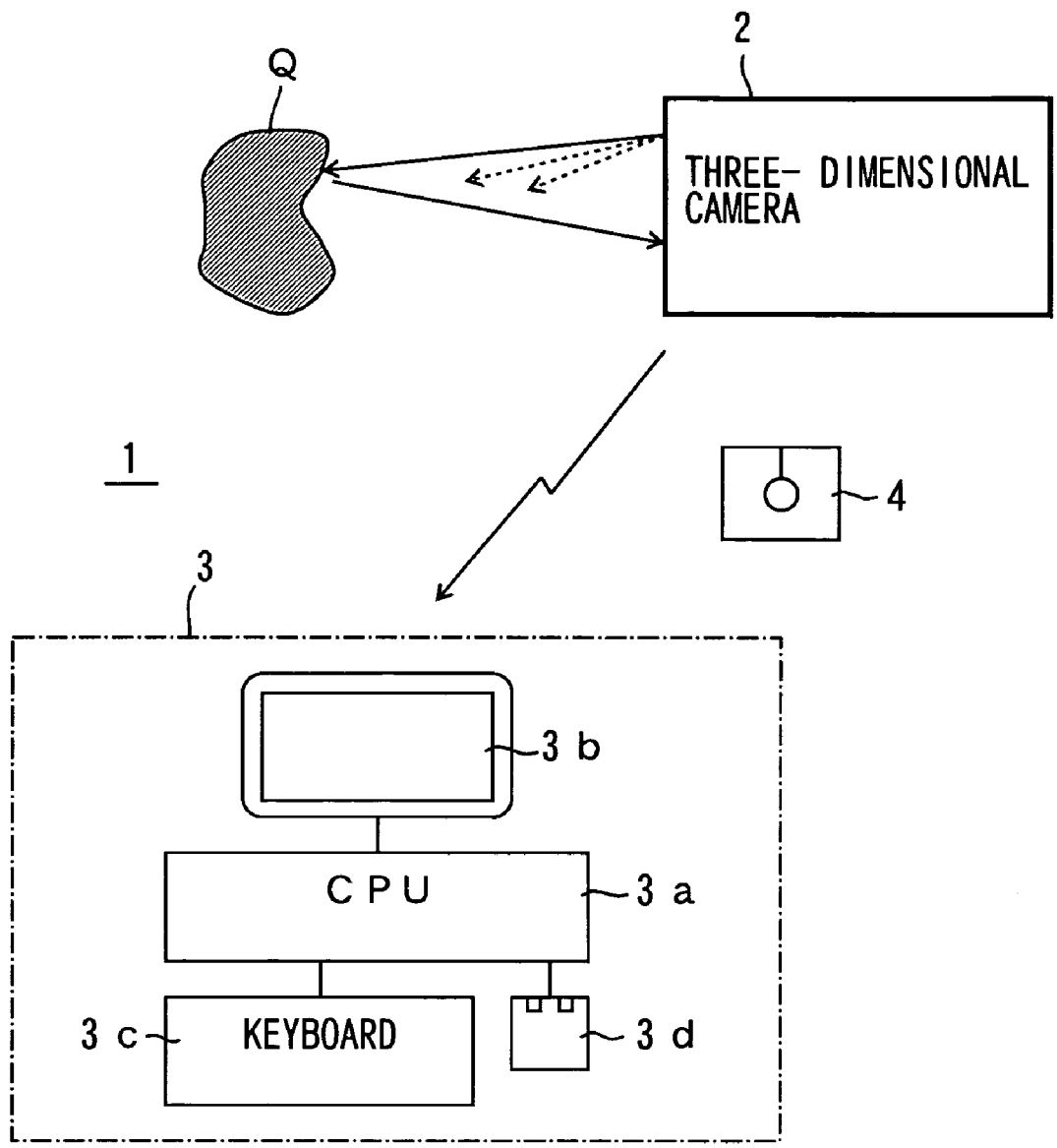

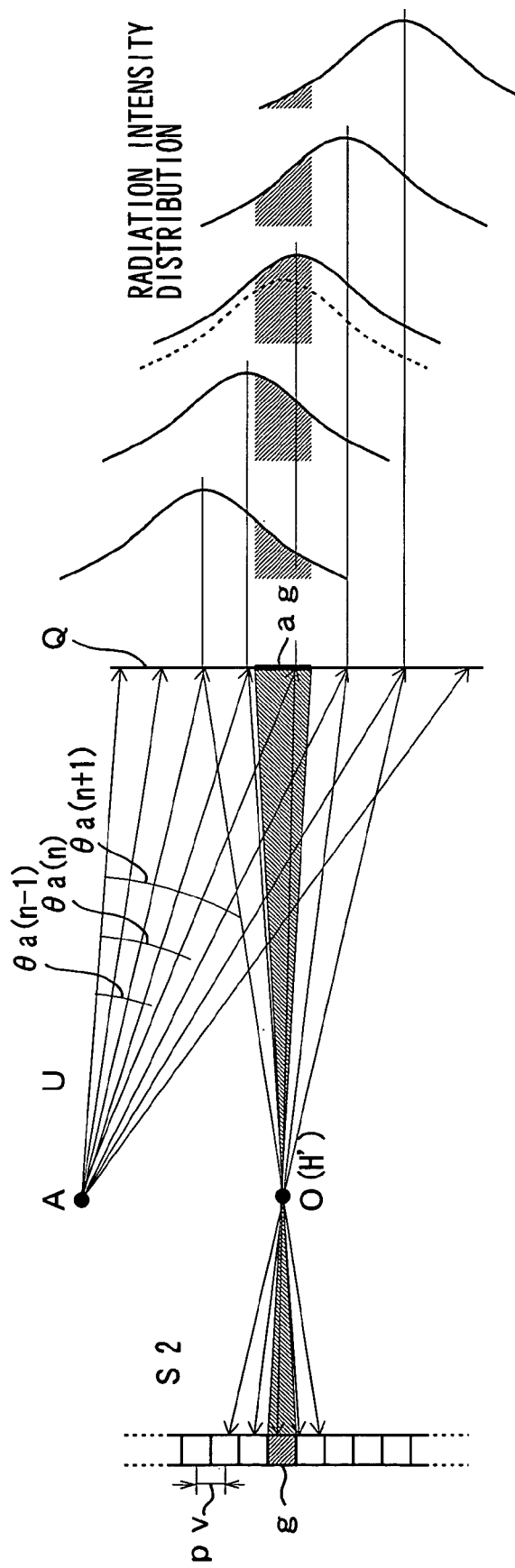
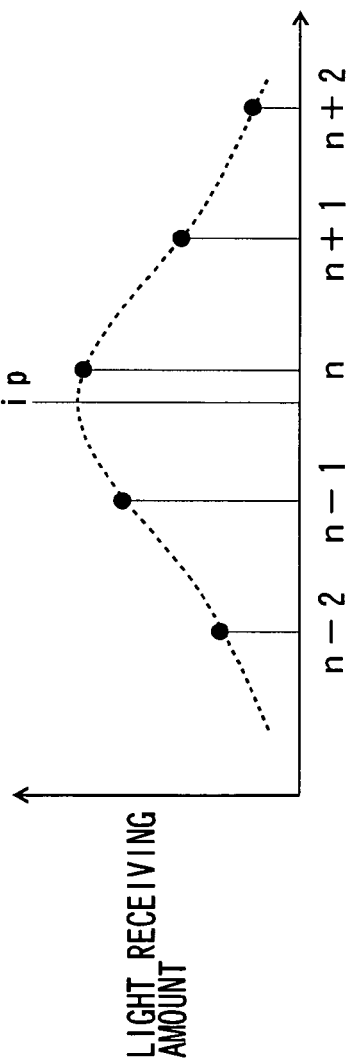
Fig. 5A
Fig. 5B

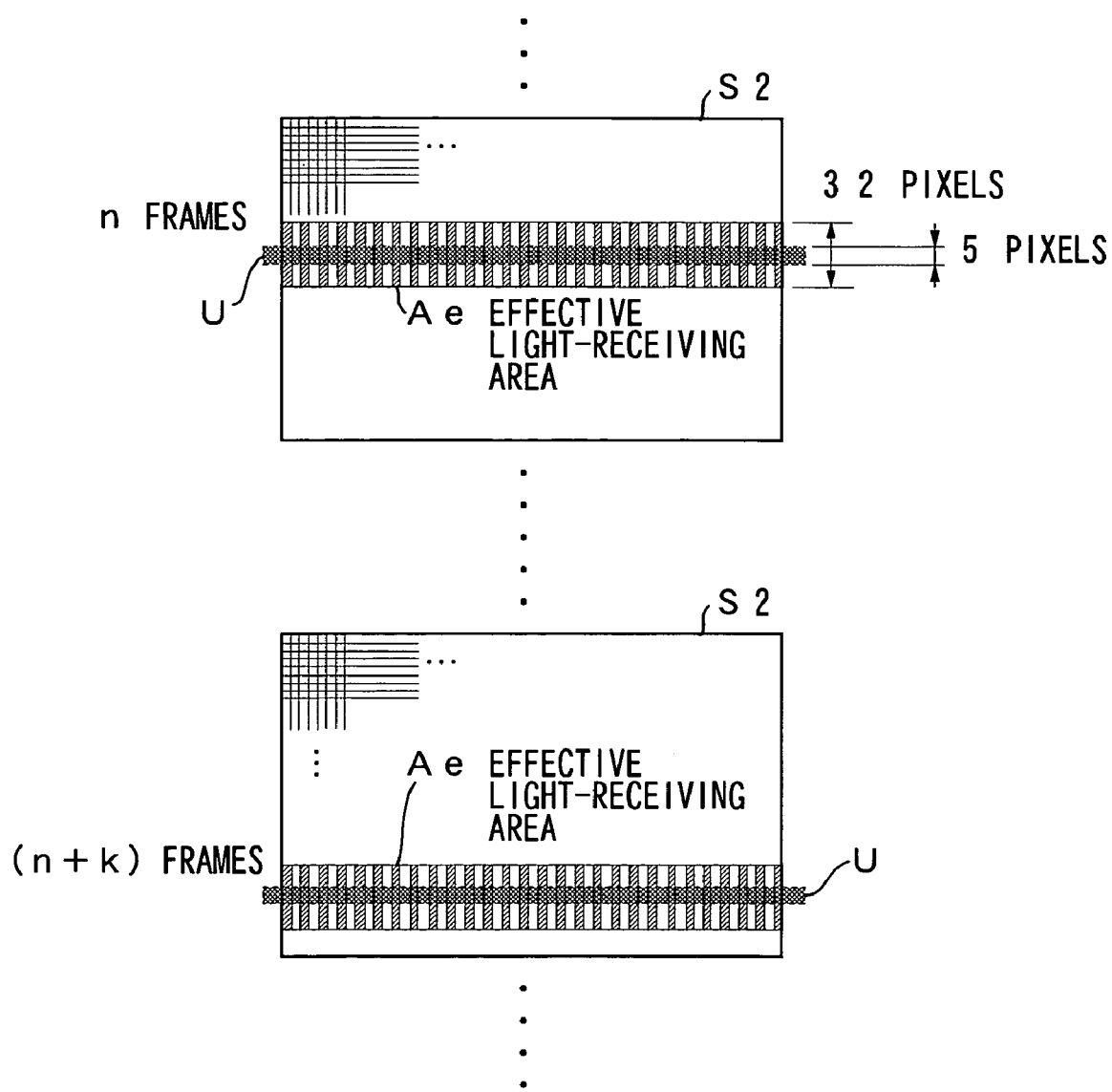

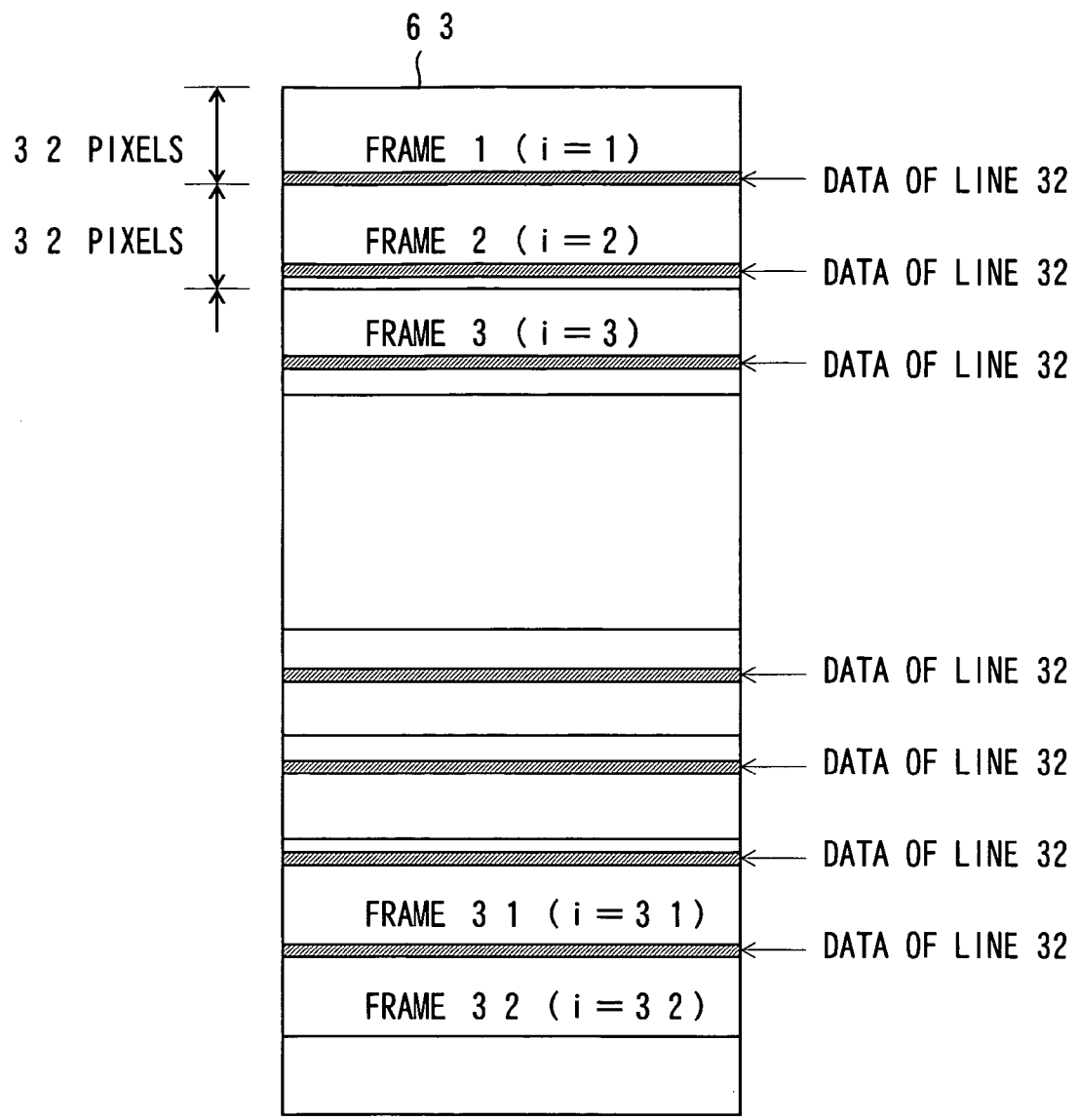

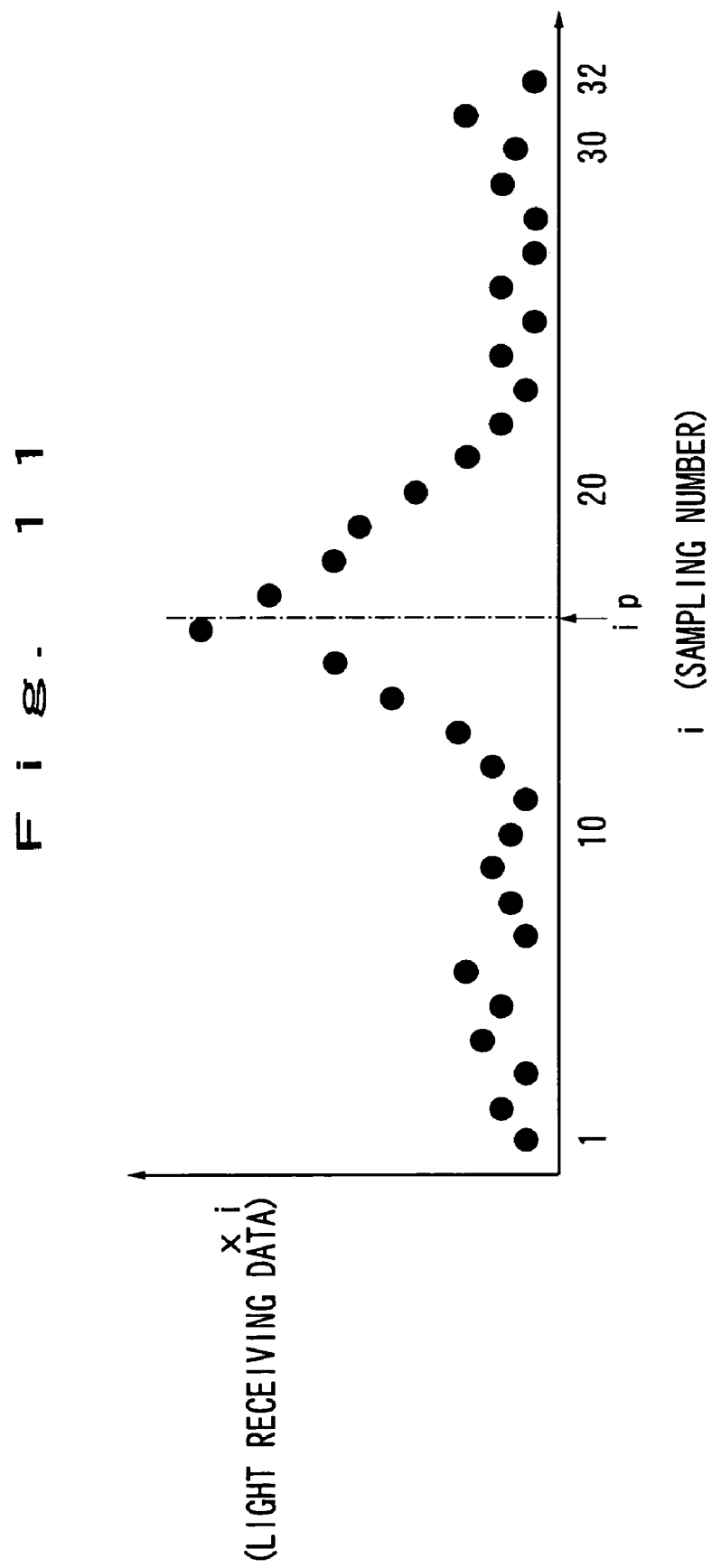

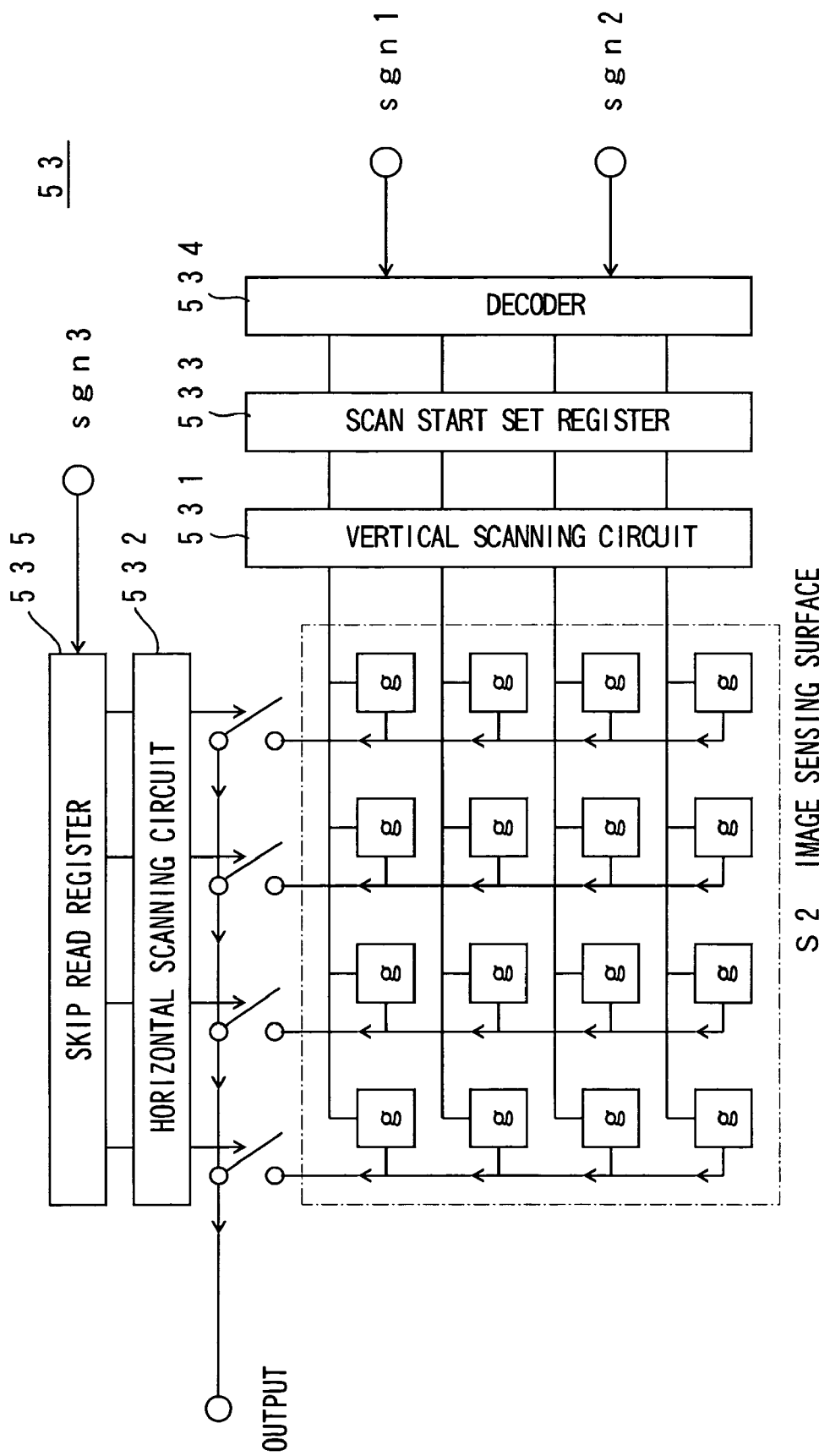

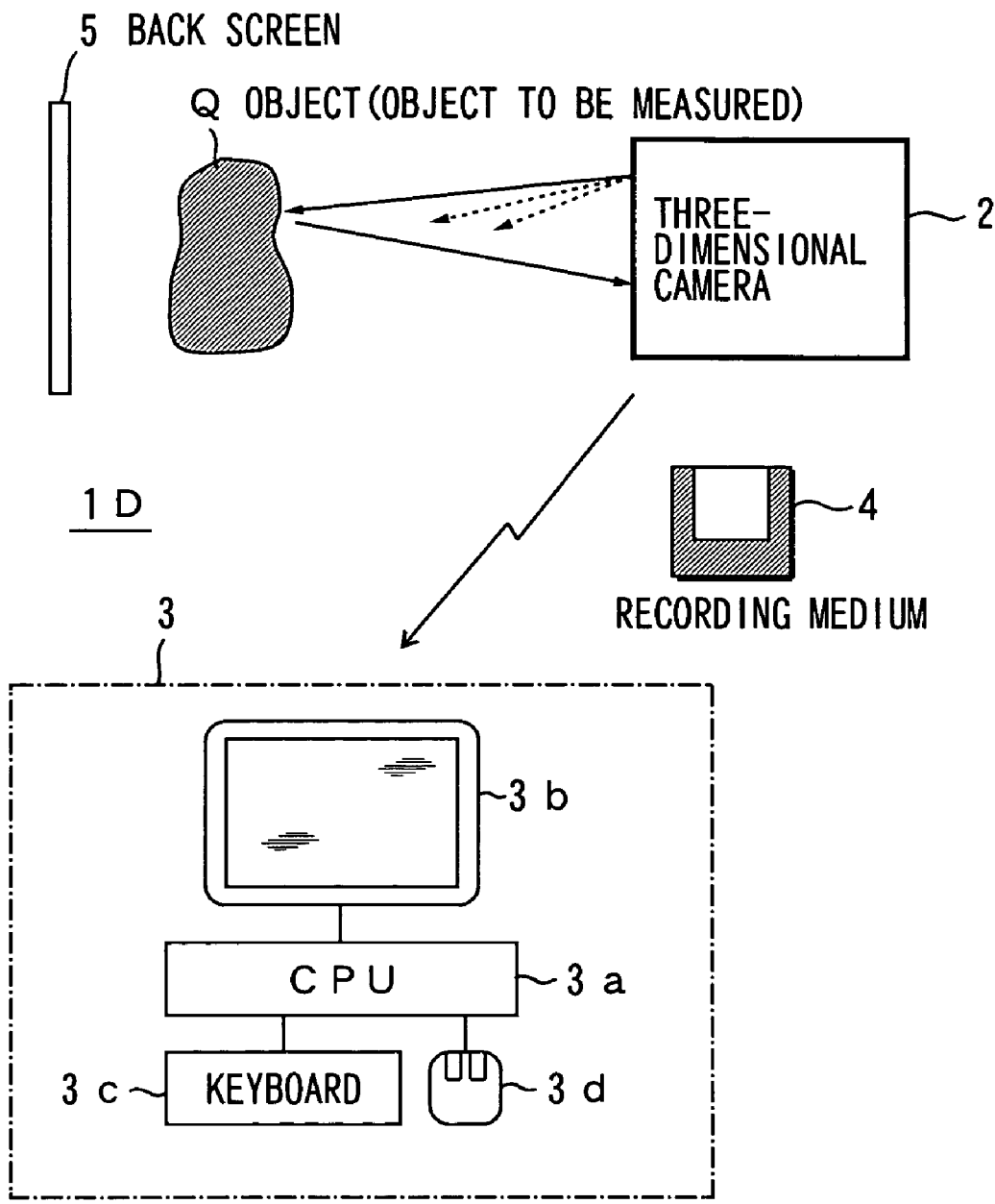

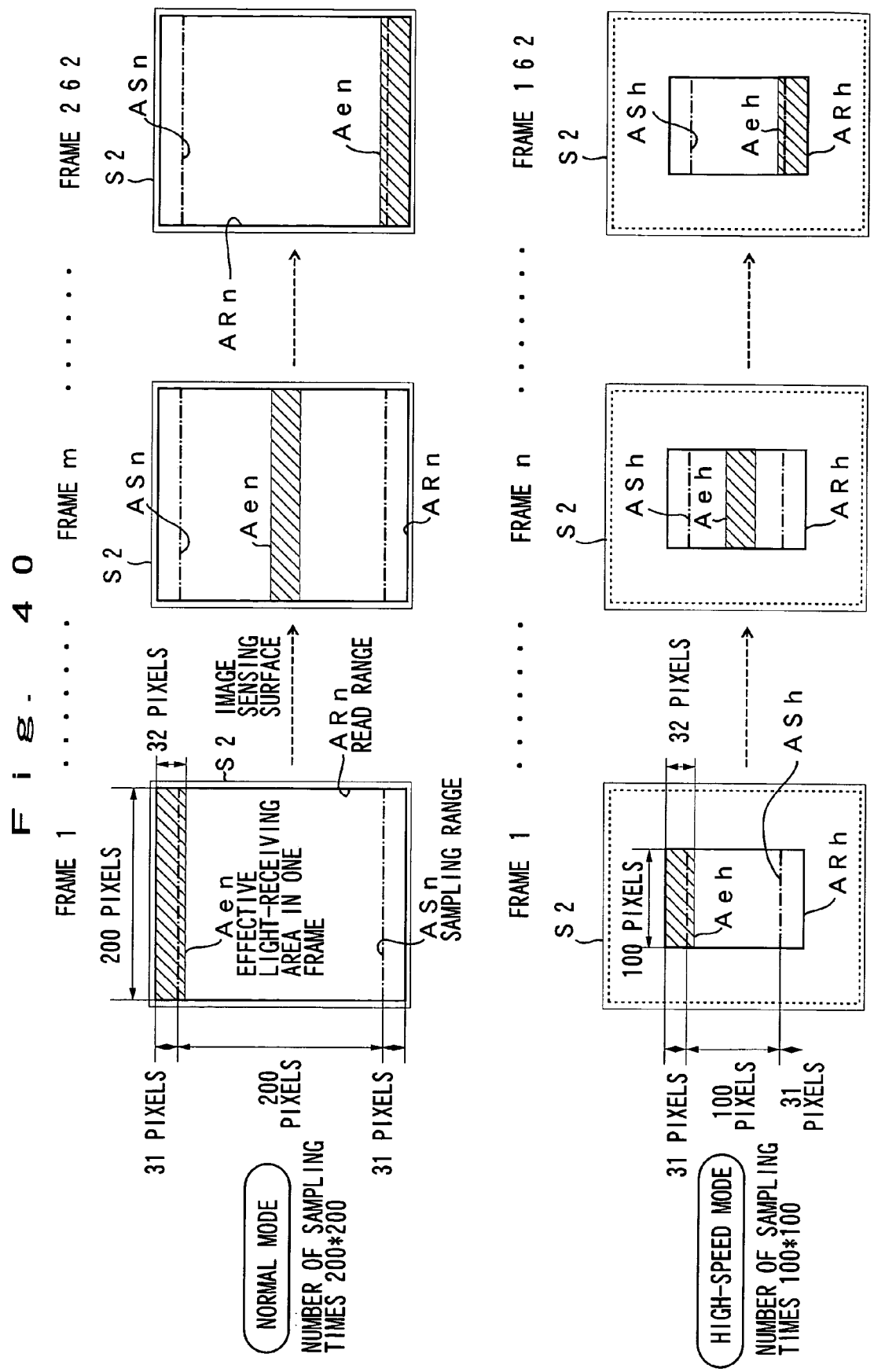

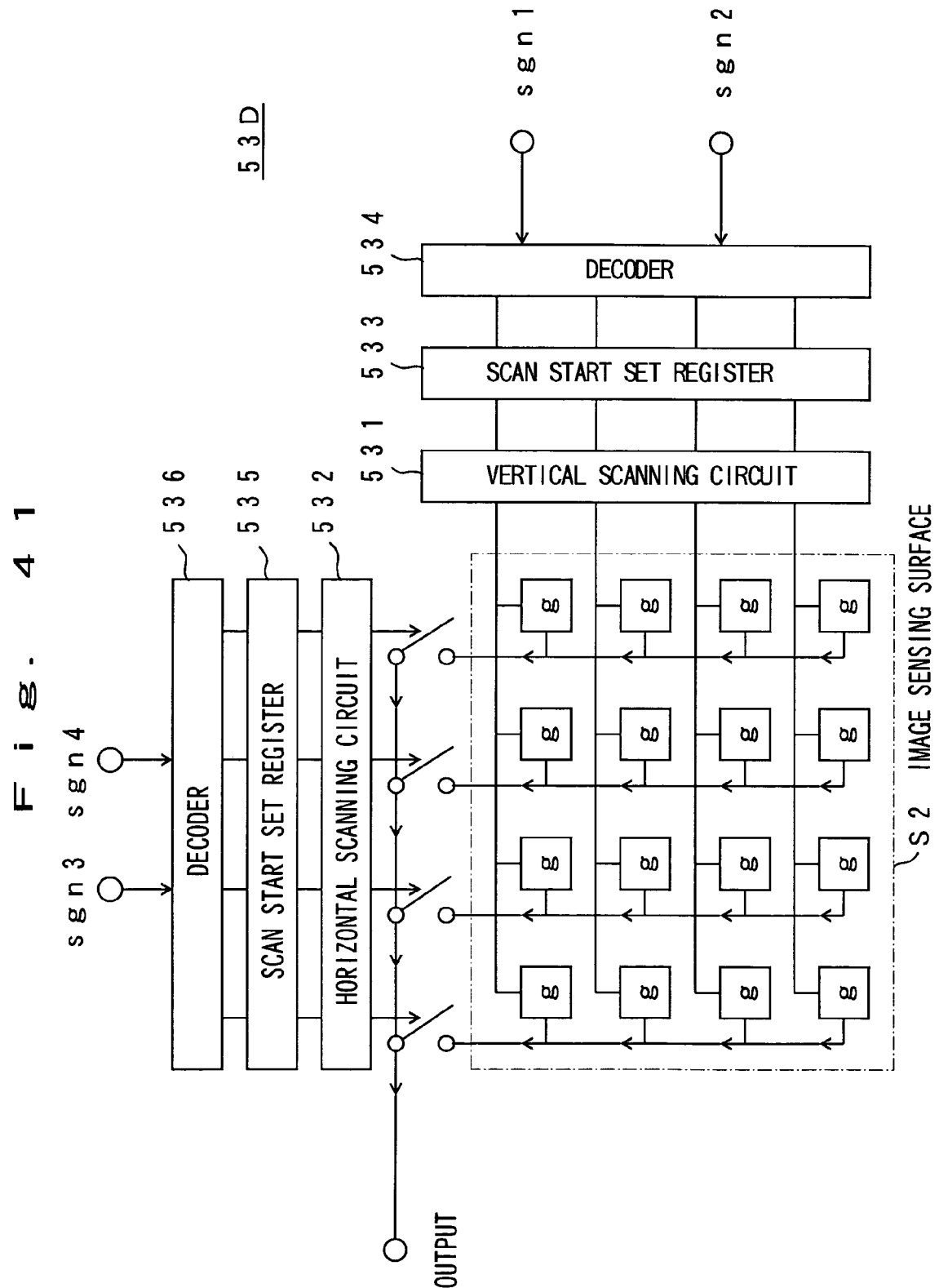

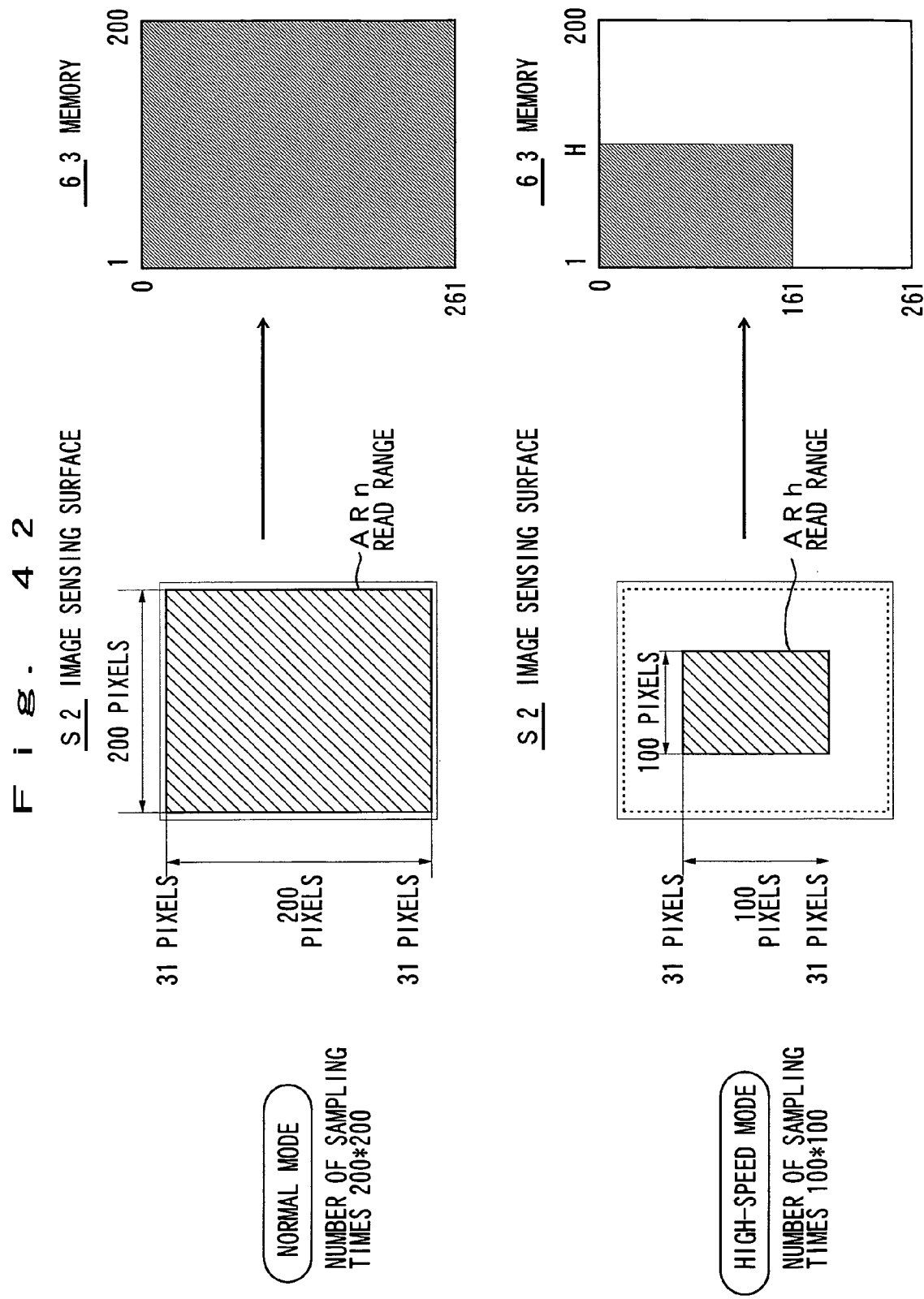

Fig. 44

(a) RELATIVE VALUE OF OUTPUT DATA AMOUNT : 1

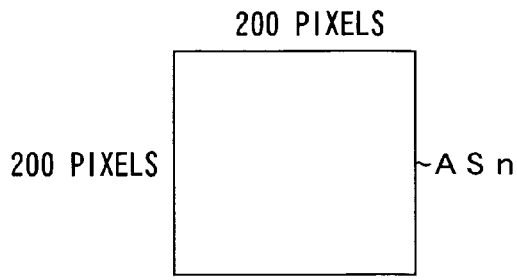
200 PIXELS × 200 PIXELS — ASn (b) RELATIVE VALUE OF OUTPUT DATA AMOUNT : 9/16

150 PIXELS × 150 PIXELS — ASh1

(c) RELATIVE VALUE OF OUTPUT DATA AMOUNT : 1/4

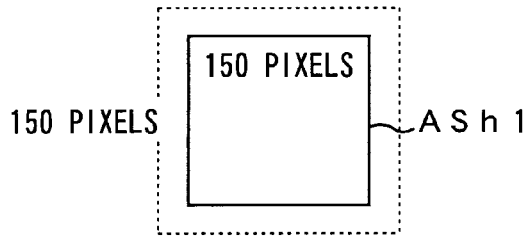
100 PIXELS × 100 PIXELS — ASh2

(d) RELATIVE VALUE OF OUTPUT DATA AMOUNT : 1/16

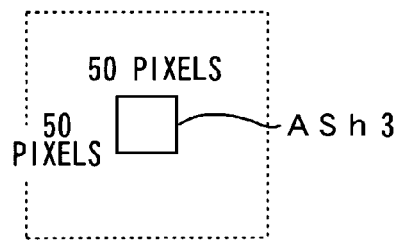
50 PIXELS × 50 PIXELS — ASh3

(e) RELATIVE VALUE OF OUTPUT DATA AMOUNT : 1/4

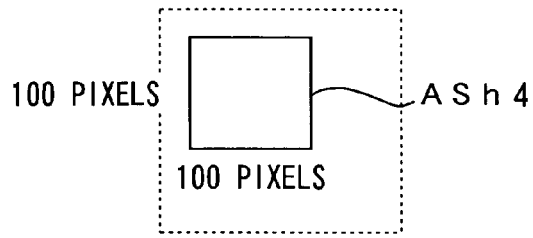
100 PIXELS × 100 PIXELS — ASh4

(f) RELATIVE VALUE OF OUTPUT DATA AMOUNT : 1/4

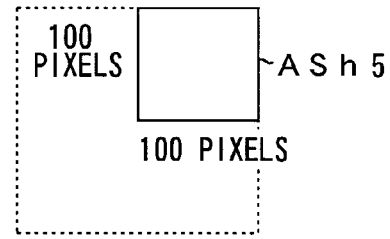
100 PIXELS × 100 PIXELS — ASh5

(g) RELATIVE VALUE OF OUTPUT DATA AMOUNT : 3/8

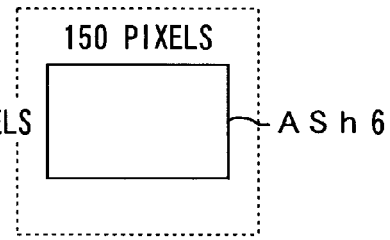
150 PIXELS × 100 PIXELS — ASh6

(h) RELATIVE VALUE OF OUTPUT DATA AMOUNT : 3/8

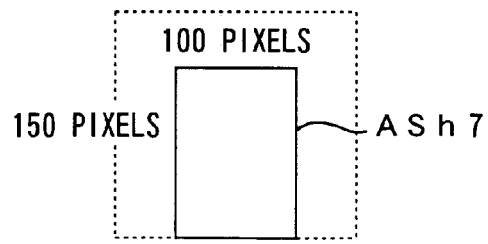
100 PIXELS × 150 PIXELS — ASh7

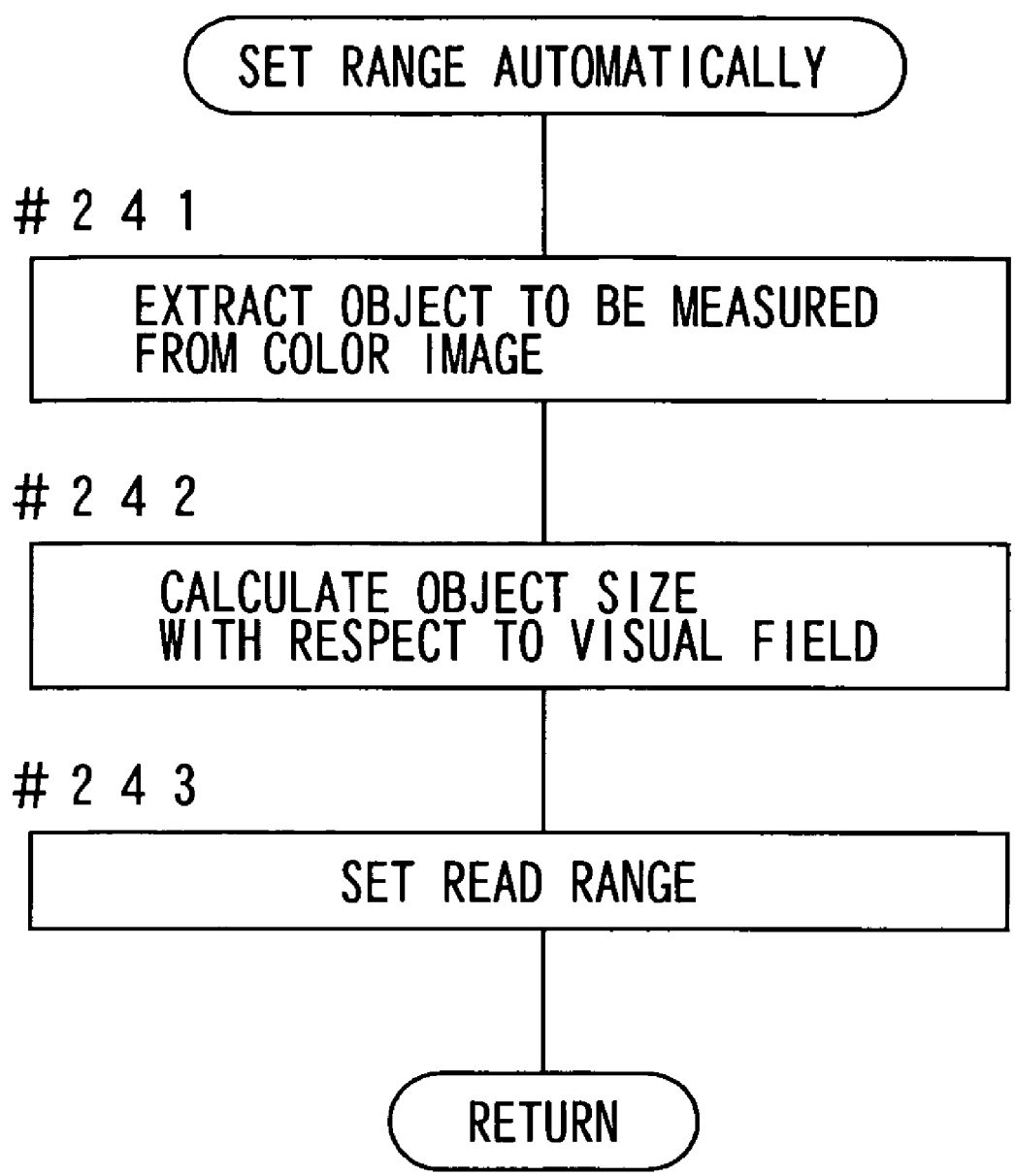

THREE-DIMENSIONAL INPUT APPARATUS AND IMAGE SENSING CONTROL METHOD

This application is based on Japanese Patent Application No. 274636/1998 filed on Sep. 29, 1998, No. 274637/1998 filed on Sep. 29, 1998, No. 274639/1998 filed on Sep. 29, 1998, and No. 81055/1999 filed on Mar. 25, 1999, the contents of which are incorporated herein by reference.

BACKGROUND OF THE INVENTION

1. Field of the Invention

The present invention relates to an apparatus for inputting and outputting three-dimensional data that determine the shape of an object by irradiating a detection light beam such as a slit light beam or a spot light beam toward the object so as to scan the object and image sensing control method.

2. Description of the Prior Art

Conventionally, a three-dimensional measuring apparatus (an apparatus for inputting three-dimensional data), which is a non-contact type and enables rapid measurement compared with a contact type, is used for data input into a CG system or a CAD system, physical measurement, visual sense of a robot or other applications.

A slit light projection method (also referred to as a light cutting method) is known as a non-contact type of three-dimensional measurement. By this method a distance image (three-dimensional image) can be obtained by scanning an object optically. The method is one of active measurement methods for taking an image of an object by irradiating a specific detection light beam (or a reference light beam). The distance image is a set of pixels that indicate three-dimensional positions of plural parts of the object. In the slit light projection method, a slit light beam having a slit-like section of the irradiated light beam is used as the detection light beam and a linear sequential scanning is performed for deflecting the detection light beam transversely of the slit. The longitudinal direction of the slit is a main scanning direction and the width direction thereof is a subscanning direction. At a certain time point in the scanning, a part of the object is irradiated and an emission line that is curved corresponding to ups and downs of the irradiated part appears on the image sensing surface (light-receiving surface). Therefore, a group of three-dimensional data that determine the shape of the object can be obtained by periodically sampling intensity of each pixel of the image sensing surface in the scanning.

A method is conventionally known in which, at a time of sampling the brightness on the image sensing surface, the objective of each sampling is limited to a partial belt-like zone (block), not the whole of the image sensing surface, on which the detection light is expected to be incident, and the belt-like zone is shifted along the subscanning direction for each sampling (Japanese Patent Application laid-open 9-145319(A)). In this method, the time required for each sampling can be shortened, so as to make scanning more rapidly, and the burden on the signal processing system can be reduced by reducing the amount of data.

By the way, the distance range (measurement range) where three-dimensional data input is possible depends on the width of the belt-like zone (the number of pixels along the subscanning direction) described above. Narrowing the width of the belt-like zone for improving the speed, therefore, causes a problem of the reduced measurement range. Thinning out the subscanning direction along which an image in the belt-like zone is read every other line, the speed can be increased while maintaining the measurement range. In such a case, however, the resolution in the depth direction of the three-dimensional data input is reduced to one half. In other words, it is impossible to obtain concavo-convex information of the object.

A CCD image sensor or a MOS type image sensor having a two-dimensional image sensing surface is used as an image sensing device (light-receiving device) of the three-dimensional measuring system described above.

The CCD image sensor is capable of resetting the accumulated electric charge and transferring the electric charge at the same timing for all the pixels on the image sensing surface. After accumulating the electric charge, each pixel data is read out sequentially. The pixel data obtained at this time are data which have been obtained at the same timing. Even when the detection light is moved, therefore, the image sensing is performed timely, thereby producing a superior three-dimensional image of the object.

In the MOS type image sensor, on the other hand, the operations of resetting, electric charge accumulation and reading are performed independently for each pixel. In other words, the image sensing timing deviates for each pixel data. It sometimes occurs therefore that a superior image of the object cannot be obtained.

With the MOS type image sensor, random access is possible and therefore the required pixels of the image sensing data can be partially selected so that the high-speed read operation is possible without reading the unrequired portion. The use of a MOS type image sensor as an image sensing device, therefore, can improve the image sensing speed.

As described above, for assuring a high-speed calculation of a three-dimensional image, only an effective light-receiving area which is a part of the image sensing surface is read out. And in order to improve the measuring resolution to be more accurate than a value corresponding to the pixel pitch in the image sensing device, a barycenter calculation is performed on the image sensing data obtained from a plurality of effective light-receiving areas.

Conventionally, a read operation of each pixel by using the MOS type image sensor as an image sensing device is performed by a horizontal read method in which each pixel is sequentially and continuously read out along the direction perpendicular to the direction in which the detection light moves on the image sensing surface (Japanese Patent Application laid-open No. 7-174536(A)).

When reading the image sensing data obtained by the MOS type image sensor, however, the effective light-receiving area is shifted line by line. Therefore, the timing of reading a specific intended pixel in the effective light-receiving area is quickened each time of shifting of the effective light-receiving area, thus deviating from the timing of shifting the effective light-receiving area by one line.

This deviation of timing is progressively increased with the sequential shifting of the effective light-receiving area for a specific intended pixel. Specifically, in the horizontal read method described above, each time the effective light-receiving area shifts, the read time of one line is added to the deviation of timing. As a result, the time lag increases from one line in maximum for the first read session to 31 lines at the 32nd read session.

In the case where the barycenter calculation is performed based on the data on a specific intended pixel in a plurality of effective light-receiving areas, therefore, the calculation result contains a considerable error and becomes unreliable. For the calculation result to be reliable, the correction process may be necessary for reducing the deviation of timing, such process is very complicated.

Also, in the three-dimensional measuring system described above, the amount of slit light received by the image sensing device varies with the reflectance of an object.

As long as the electric charge accumulation time of the image sensing device is fixed to a predetermined time, therefore, the output of the image sensing device is saturated for a high reflectance. Conversely, a low reflectance poses the problem of an inferior S/N ratio due to an excessively low output of the image sensing device.

For determining a three-dimensional shape (distance distribution) of an object, on the other hand, it is necessary to accurately detect the receiving position or the receiving timing of slit light. For this reason, as described above, the barycenter calculation is performed based on the sensor output produced before and after a particular position or time point. The barycenter calculation requires an accurate output of the image sensing device. In the case of an inferior S/N ratio as described above or in the case where the output of the image sensing device is saturated, an accurate barycenter calculation is difficult.

To solve this problem in the prior art, a slit light beam is projected once to produce an output of the image sensing device so as to set an appropriate accumulation time. The accumulation time thus set, however, is shared by all the pixels of the image sensing device, and therefore the problem described above still remains unsolved in the case where the reflectance of the object is partially low or high.

Also, in the three-dimensional measuring system described above, an object may decrease in size extremely as compared with the visual field of image sensing. The size of the object with respect to the visual field is determined by the image sensing angle of view and the image sensing distance. The angle of view can be adjusted by a zoom function but has a minimum value determined by the zoom specification. The image sensing distance also has a tolerance so that the image sensing at closer than a minimum distance (generally, several tens of centimeters to one meter) is impossible.

Conventionally, although the read range of the image sensing at each sampling in each main scanning is a part of the image sensing surface, the whole image sensing surface represents the read range in the context of the whole scanning period. In the case where an object is excessively small as compared with the visual field as mentioned above, therefore, the problem is that the unrequired data represents a large proportion of the data obtained by sampling, i.e. the data read operation from the image sensing device and subsequent data processing are very inefficient.

SUMMARY OF THE INVENTION

An object of the present invention is to shorten the time required for three-dimensional data input at a predetermined angle of view without reducing the resolution and the distance range capable of three-dimensional data input.

Another object of the present invention is to produce an accurate three-dimensional image without necessity of processing for correcting the deviation between the timing of reading an intended pixel in an effective light-receiving area and the timing of shifting the effective light-receiving area by one line.

Still another object of the present invention is to produce an output not saturated or an output superior in S/N ratio from an image sensing device.

A further object of the present invention is to shorten the time required for three-dimensional data input and to lighten the burden of data processing by reducing the wasteful reading of an image sensing device.

According to a preferred embodiment of the present invention, there is provided a three-dimensional data input apparatus for generating data specifying the shape of an object by detecting the light from an object comprising a projector for irradiating a detection light beam toward the object so as to scan a virtual surface, an image sensing device for receiving the light reflected from the object, and a controller for making the image sensing device output thinned-out data in a direction corresponding to the main scanning direction on the virtual surface.

According to another preferred embodiment of the present invention, there is provided a three-dimensional data input apparatus further comprising a controller for controlling the image sensing device by repeatedly reading a light-receiving signal on a line along the moving direction of the received detection light in an effective area constituting a part of the image sensing surface.

BRIEF DESCRIPTION OF THE DRAWINGS

FIG. 1 is a diagram showing a configuration of a measuring system according to the present invention.

FIGS. 5A and 5B are diagrams showing the principle of calculating a three-dimensional position in the measuring system.

FIG. 6 is a diagram showing the read range of an image sensor.

FIG. 8 is a diagram showing the light-receiving data stored in each frame.

FIG. 11 is a diagram showing the concept of the temporal barycenter.

FIG. 12 is a diagram showing a model configuration of an image sensor.

FIG. 37 is a diagram showing a configuration of a measuring system according to a fourth embodiment.

FIG. 40 is a diagram showing the read range of an image sensor.

FIG. 41 is a model diagram showing another example of the configuration of the image sensor.

FIG. 42 is a diagram showing the read data amount in normal mode and high-speed mode.

FIG. 44 is a diagram showing a modification of means for setting a sampling range.

FIG. 46 is a flowchart showing an automatic range setting subroutine.

DESCRIPTION OF THE PREFERRED EMBODIMENTS

First Embodiment

Figure 2A:
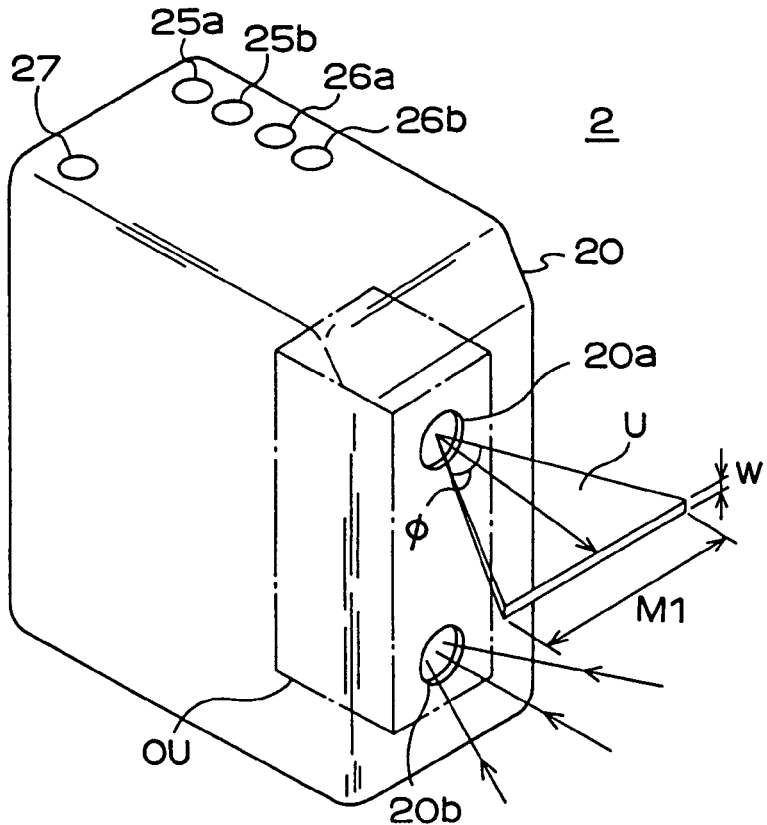
FIG. 2A is a perspective view showing the appearance of a three-dimensional camera.

FIG. 1 is a diagram showing a configuration of a measuring system 1 according to this invention.

The measuring system 1 comprises a three-dimensional camera 2 for conducting three-dimensional measurement by the slit light projection method, and a host 3 for processing output data of the three-dimensional camera 2.

The three-dimensional camera 2 outputs a two-dimensional image indicating color information of an object Q and the data required for calibration as well as the measurement data specifying the three-dimensional position of a plurality of sampling points on the object Q. The calculation processing for determining the coordinates of the sampling points using triangulation are performed by the host 3.

The host 3 is a computer system including a CPU 3a, a display 3b, a keyboard 3c and a mouse 3d. The CPU 3a has built therein software for processing the measurement data.

Data can be transmitted and received between the host 3 and the three-dimensional camera 2 in two forms, on-line by cable or infrared communication and off-line by a portable recording medium 4. The recording medium 4 includes a magneto-optic disk (MO), a mini-disk (MD) or a memory card.

Figure 2B:
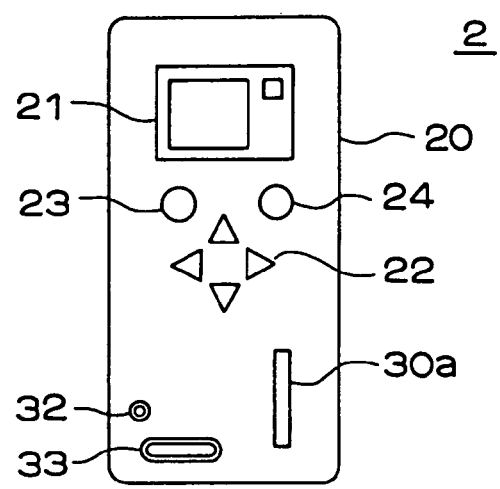
FIG. 2B is a back view showing the appearance of the three-dimensional camera.

FIGS. 2A and 2B are diagrams showing the outer appearance of the three-dimensional camera 2.

A projection window 20a and a light-receiving window 20b are formed in the front surface of a housing 20. The projection window 20a is located above the light-receiving window 20b. A slit light beam (a laser beam in stripe having a predetermined width w) U emitted by an internal optical unit OU proceeds toward an object to be measured through the projection window 20a. The irradiation angle φ of the slit light beam U along the length direction M1 is fixed. A portion of the slit light beam U reflected from the surface of the object is incident in the optical unit OU through the light-receiving window 20b. The optical unit OU includes a biaxial adjust mechanism for legitimizing the relationship between the projection axis and the light-receiving axis.

Zooming buttons 25a, 25b, manual focusing buttons 26a, 26b, and a shutter button 27 are provided on the upper surface of the housing 20. As shown in FIG. 2B, a liquid crystal display unit 21, a cursor button 22, a select button 23, a cancel button 24, an analog output terminal 32, a digital output terminal 33 and an insertion hole 30a of a recording medium 4 are arranged on the rear surface of the housing 20.

The liquid crystal display (LCD) unit 21 is used for displaying an operating screen and used as an electronic finder at the same time. An image sensing operator can set an image sensing mode with the buttons 22 to 24 on the rear side. A two-dimensional image signal of NTSC type, for example, is output from the analog output terminal 32. The digital output terminal 33 may be a SCSI terminal.

Figure 3:
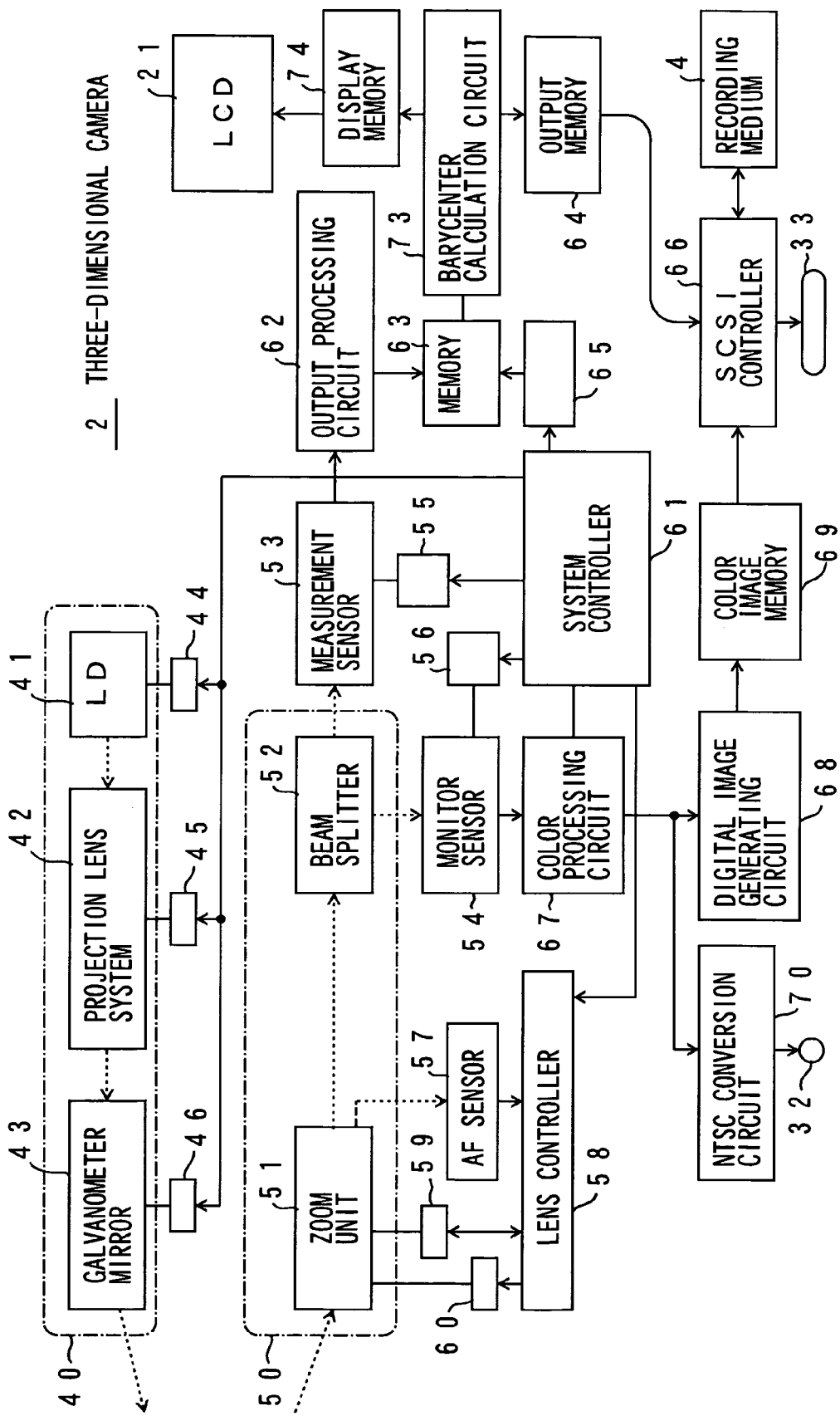
FIG. 3 is a block diagram showing the functional configuration of the three-dimensional camera.

FIG. 3 is a block diagram showing a functional configuration of the three-dimensional camera 2. In the diagram, solid arrows indicate the flow of electrical signals and dashed arrows indicate the flow of light.

The three-dimensional camera 2 includes two optical systems 40, 50 on the projection side and the light-receiving side, respectively, constituting the optical unit OU.

In the optical system 40, a laser beam having a wavelength of 685 nm emitted from a semiconductor laser (LD) 41 is converted into a slit light beam U as it passes through the projection lens system 42 and deflected by a galvanometer mirror (scanning means) 43. A driver 44 of the semiconductor laser 41, the drive system 45 of the projection lens system 42 and a drive system 46 of the galvanometer mirror 43 are controlled by a system controller 61.

In the optical system 50, on the other hand, the light focused by a zoom unit 51 is split by a beam splitter 52. The light having the bandwidth of the oscillation wavelength of the semiconductor laser 41 is incident on the image sensor 53 for measurement. The light in the visible bandwidth, on the other hand, is incident on a color sensor 54 for monitoring. The image sensor 53 is a MOS area sensor with pixels (light-receiving elements) arranged two-dimensionally and capable of reading an arbitrary pixel. The color sensor 54 is a CCD area sensor. The zoom unit 51 is of an internal focusing type so that a part of the incident light is used for auto focusing (AF). The AF function is realized by an AF sensor 57, a lens controller 58 and a focusing drive system 59. A zooming drive system 60 is provided for the electrically-operated zooming function.

The flow of information on the object in the three-dimensional camera 2 is as follows.

First, image sensing information from the image sensor 53 is transferred to an output processing circuit 62 in synchronism with clock from the driver 55. The output processing circuit 62 includes an amplifier for amplifying the photoelectric conversion signal of each pixel g output from the image sensor 53 and an AD converter for converting the photoelectric conversion signal into an 8-bit light-receiving data. A memory 63 is a read-write memory having a storage capacity of 200×32×33 bytes for storing the light-receiving data output from the output processing circuit 62. A memory control circuit 65 designates an address for writing into and reading from the memory 63.

A barycenter calculation circuit 73 generates a gray level image (distance image) corresponding to the shape of the object to be measured based on the light-receiving data stored in the memory 63 and outputs it to a display memory 74. Also, data for the base of calculating the three-dimensional position is calculated and output to the output memory 64. The gray level image stored in the display memory 74, the color image stored in a color image memory 69, an operation guide screen, etc. are displayed on the LCD 21.

The image sensing information from the color sensor 54, on the other hand, is transferred to the color processing circuit 67 in synchronism with the clock from the driver 56. The image sensing information, after color processing, is output on-line through a NTSC conversion circuit 70 and an analog output terminal 32, or quantized in a digital image generator 68 and stored in the color image memory 69. After that, the color image data is transferred from the color image memory 69 to the SCSI controller 66, output on-line from the digital output terminal 33, or stored in the recording medium 4 in a position corresponding to the measurement data. The color image is an image having the same angle of view as the distance image from the image sensor 53. Specifically, the visual image of light-receiving due to the color image sensor 54 substantially coincides with the visual field of light-receiving due to the image sensor 53. The color image is used as reference information in the application processing by the host 3. The process using the color information includes the process for generating a three-dimensional model by combining a plurality of measurement data having different camera viewing points and the process of thinning out the unrequired apexes of a three-dimensional model.

An operation order is sent to the system controller 61 from the operating unit including the buttons 22 to 24. The system controller 61 issues an instruction to a character generator (not shown) for displaying appropriate characters and symbols on the screen of the LCD 21. Also, the system controller 61 reads and variously analyzes the color image from the color image memory 69.

Figure 4A:
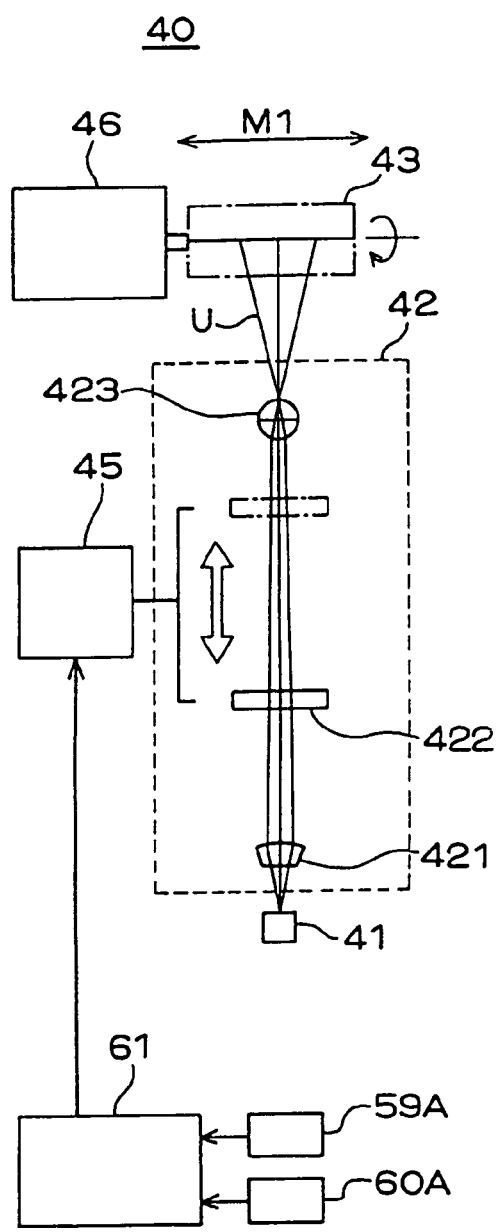
FIGS. 4A and 4B are diagrams showing a model configuration of a projection lens system.
Figure 4B:
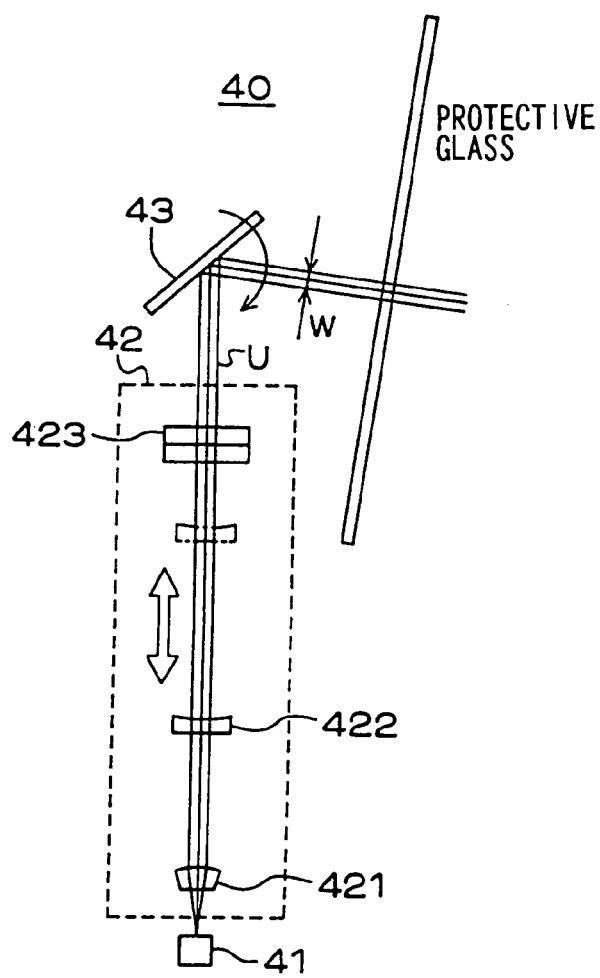

FIGS. 4A and 4B are model diagrams showing a configuration of the projection lens system 42. FIG. 4A is a front view thereof, and FIG. 4B is a side view thereof.

The projection lens system 42 is configured with three lenses including a collimator lens 421, a variator lens 422 and an expander lens 423. The laser beam emitted from the semiconductor laser 41 is optically processed to produce an appropriate slit light beam U in the following sequence. First, the beam is collimated by the collimator lens 421. Then, the variator lens 422 adjusts the laser beam diameter.

Finally, the beam is expanded along the slit length direction M1 by the expander lens 423.

The variator lens 422 is provided for making the slit light beam U having a width corresponding to three or more pixels to be incident on the image sensor 53 regardless of the image sensing distance or the image sensing angle of view. The drive system 45, in compliance with the instruction from the system controller 61, moves the variator lens 422 so as to maintain a constant width w of the slit light beam U on the image sensor 53. The variator lens 422 and the zoom unit 51 on the light-receiving side are operatively interlocked with each other.

By expanding the slit length before deflection by the galvanometer mirror 43, the distortion of the slit light beam U can be reduced as compared with when it is expanded after deflection. The expander lens 423 is arranged in the last stage of the projection lens system 42, i.e. in proximity to the galvanometer mirror 43, whereby the galvanometer mirror 43 can be reduced in size.

FIGS. 5A and 5B are diagrams showing the principle of calculating the three-dimensional position in the measuring system 1. For facilitating the understanding, the received light amount for each pixel g is shown only for five sampling sessions.

The object Q is irradiated with a comparatively wide slit light beam U representing a plurality of pixels on the image sensing surface (light-receiving surface) of the image sensor 53. Specifically, the width of the slit light beam U is assumed to represent five pixels. The slit light beam U is deflected downward in FIG. 5A so as to move by one pixel pitch pv on the image sensing surface S2 at each sampling period, so that the object Q (strictly speaking, a virtual plane at right angles to the depth) is scanned. The direction in which the slit light beam U is deflected is the subscanning direction. At each sampling period, the light-receiving data (photoelectric conversion information) corresponding to one frame is output from the image sensor 53. This deflection is actually effected at a conformal rate.

Reference is made to one pixel g of the image sensing surface S2. According to this embodiment, 32 pieces of light-receiving data are obtained by 32 sampling operations performed during the scanning. By the barycenter calculation for the 32 pieces of light-receiving data, the timing (temporal barycenter Npeak or the barycenter ip) is determined at which the optical axis of the slit light beam U passes through the object surface ag in the range covered by the intended pixel g.

In the case where the object Q has a flat surface free of noises caused by the characteristics of the optical system, the light-receiving amount of the intended pixel g is increased at the timing when the slit light beam U passes as shown in FIG. 5B, and generally assumes almost an normal distribution. In the case where the light-receiving amount is maximum at a timing between the nth session and the (n−1)th session as shown, the timing coincides substantially with the temporal barycenter Npeak.

The position (coordinates) of the object Q is calculated based on the relationship between the direction of irradiation of the slit light beam at the temporal barycenter Npeak thus determined and the direction of incidence of the slit light beam into the intended pixel. As a result, the measurement is possible with a resolution higher than that specified by the pixel pitch pv of the image sensing surface.

By the way, the light-receiving amount of the intended pixel g is dependent on the reflectance of the object Q. However, the ratio of each light-receiving amount between sampling sessions is constant regardless of the absolute light-receiving amount. In other words, the density of the object color has no effect on the measuring accuracy.

FIG. 6 is a diagram showing the read range of the image sensor 53.

As shown in FIG. 6, one frame is read in the image sensor 53 not over the whole image sensing surface S2 but only for the effective light-receiving area (striped image) Ae constituting a part of the image sensing surface S2 in order to increase the speed. Further, according to this embodiment, data is thinned out when being read in the direction corresponding to the main scanning direction of the object Q. The thinned-out reading will be described in detail later.

The effective light-receiving area Ae is an area on the image sensing surface S2 corresponding to the measurable distance range d' (FIG. 14) of the object Q at an irradiation timing of the slit light beam U, and is shifted by one pixel for each frame with the deflection of the slit light beam U. According to this embodiment, the number of pixels in the direction of shifting the effective light-receiving area Ae is fixed to 32.

There are 200 pixels along the length direction (horizontal direction) of the effective light-receiving area Ae. In the high-speed mode when thinned-out reading is carried out, however, a part of the 200 pixels (100 pixels in the case where the thin-out ratio m is 0.5, for example) are read.

As described above, the image sensor 53 is a MOS sensor capable of random access. Therefore, only the required pixels of the image sensing data can be selected and the read operation can be performed at high speed without reading the unrequired portion.

Figure 7A:
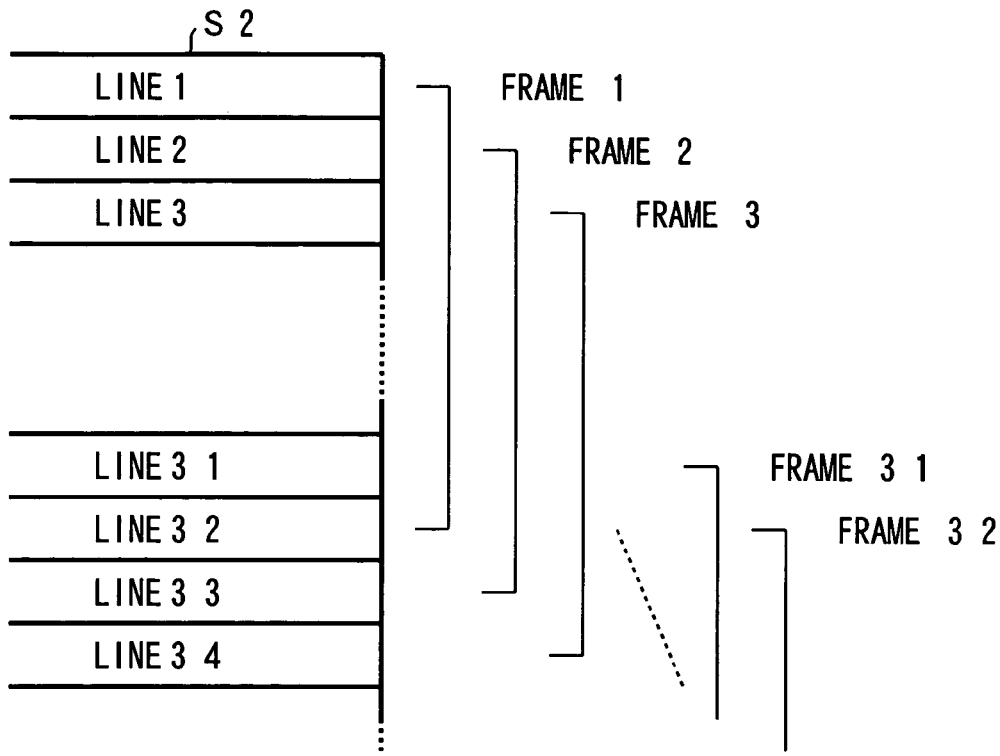
FIGS. 7A and B are diagrams showing the relationship between line and frame on an image sensing surface of the image sensor.
Figure 7B:
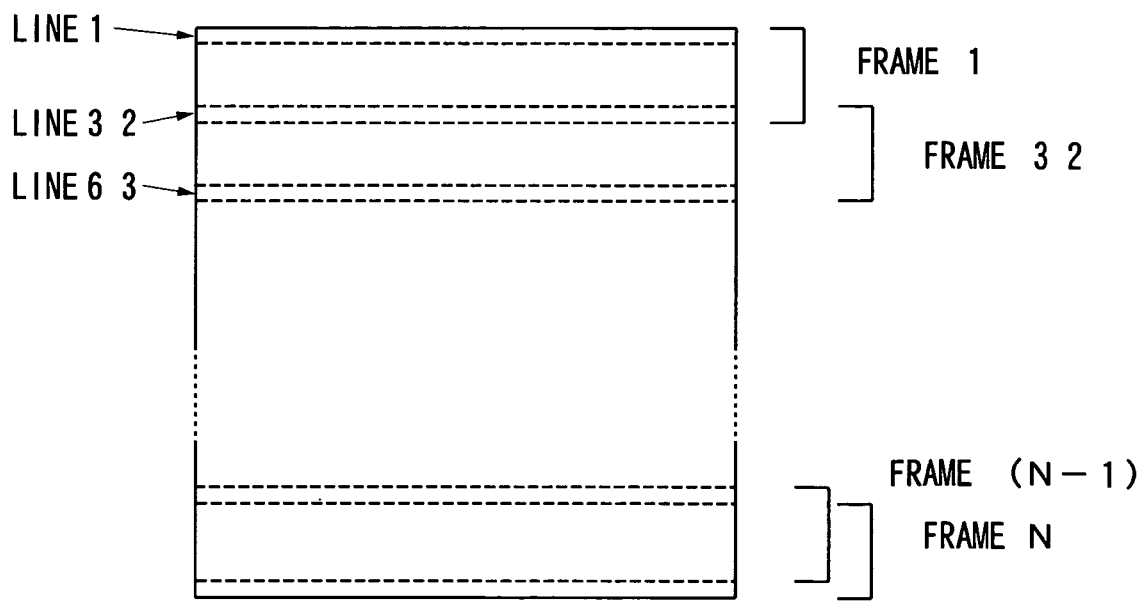
Figure 9:
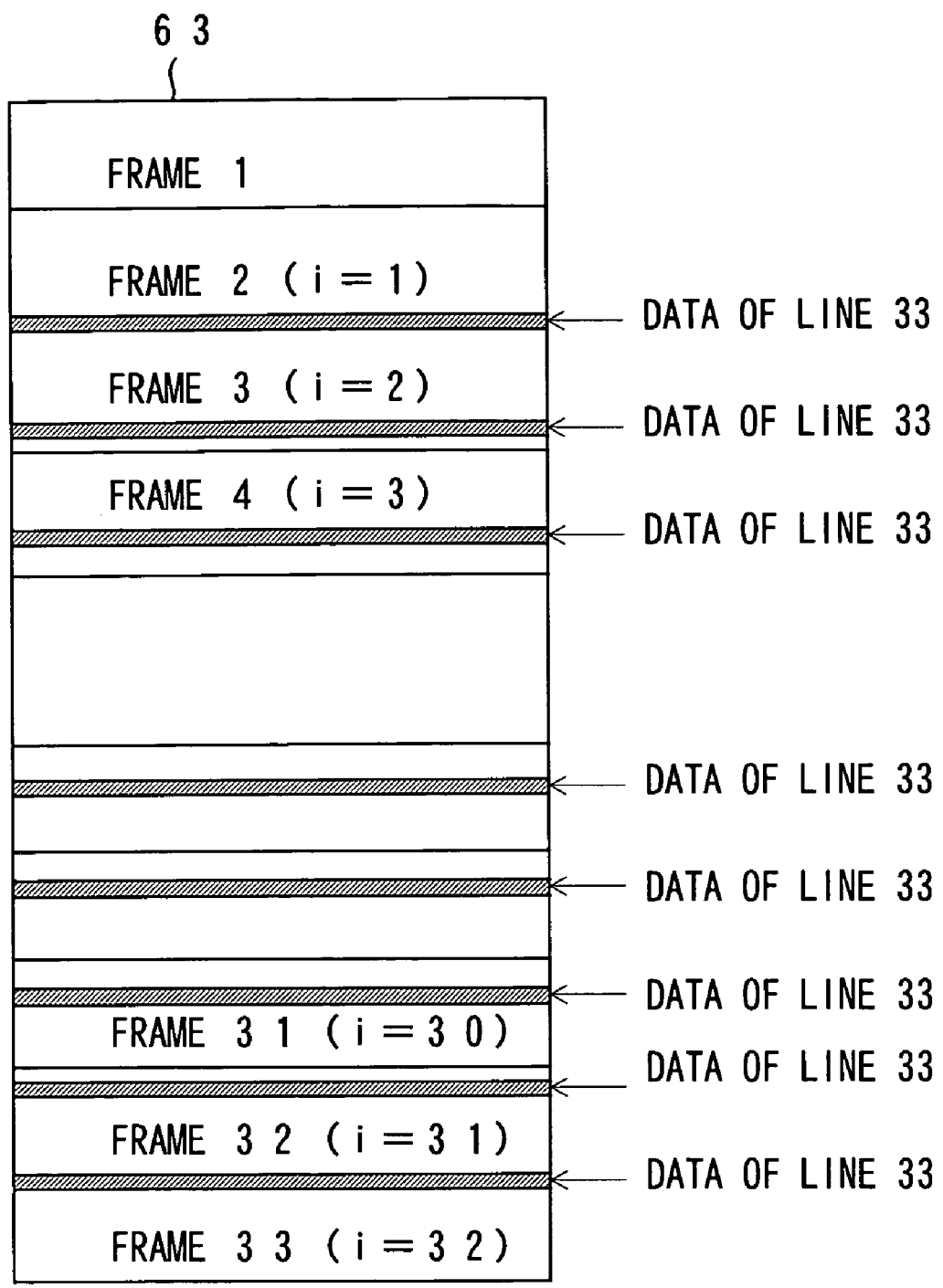
FIG. 9 is a diagram showing the light-receiving data stored in each frame.
Figure 10:
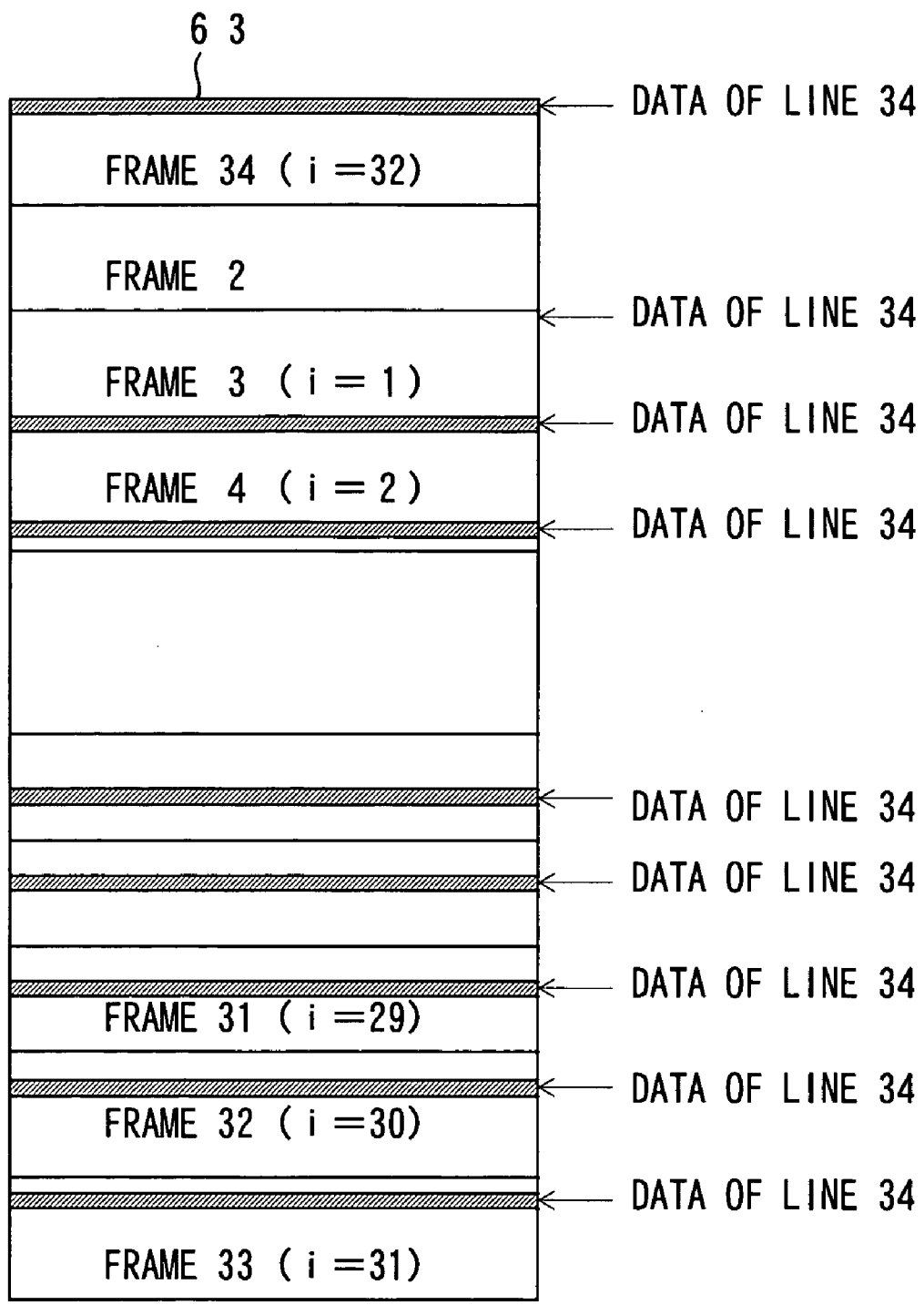
FIG. 10 is a diagram showing the light-receiving data stored in each frame.

FIGS. 7A and 7B are diagrams showing the relationship between the line and the frame on the image sensing surface S2 of the image sensor 53, and FIGS. 8 to 10 are diagrams showing the light-receiving data of each frame stored in the memory 63.

As shown in FIGS. 7A and 7B, the first frame of the image sensing surface S2 contains the light-receiving data corresponding to 32 lines (32×200 pixels) from line 1 constituting the head line of the read range to line 32 in normal mode. The light-receiving data of 32 lines are also contained in high-speed mode, although the number of pixels per line is less than 200. The frame 2 represents lines 2 to 33, and the frame 3 represents lines 3 to 34. In this way, each frame is shifted by one line. The frame 32 represents 32 lines from lines 32 to 63.

The light-receiving data of frames 1 to 32 are sequentially transferred to the memory 63 through the output processing circuit 62 and stored in the state shown in FIG. 8. Specifically, the memory 63 has stored therein the light-receiving data of frames 1, 2, 3 and so forth in that order. The data of line 32 contained in each frame is shifted upward one line for each frame, e.g. the 32nd line for frame 1, the 31st line for frame 2, and so on. Once the light-receiving data of frames 1 to 32 are stored in the memory 63, the temporal barycenter Npeak for each pixel of line 32 is calculated.

While the calculation is going on for line 32, the light-receiving data of frame 33 is transferred to and stored in the memory 63. As shown in FIG. 9, the light-receiving data of frame 33 is stored in the area next to frame 32 of the memory 63. Once the data of frame 33 is stored in the memory 63, the temporal barycenter Npeak is calculated for each pixel of line 33 contained in frames 2 to 33.

While the calculation for line 33 is going on, the light-receiving data of frame 34 are transferred to and stored in the memory 63. As shown in FIG. 10, the light-receiving data of frame 34 is overwritten in the area where frame 1 has been stored. At this time point, the data in frame 1 has been processed, and therefore the erasure thereof by overwrite poses no problem. After the data of frame 34 is stored in the memory 63, the temporal barycenter Npeak is calculated for each pixel of line 34, After processing the light-receiving data of frame 34, the light-receiving data of frame 35 is overwritten in the area where frame 2 has thus far been stored.

In this way, the temporal barycenter Npeak is calculated for a total of 200 lines up to the last line 231.

As described above, new light-receiving data are sequentially overwritten and stored in the areas where unrequired data have been stored among the light-receiving data stored in the memory 63, thereby making it possible to reduce the capacity of the memory 63.

The barycenter ip stored in the display memory 74 is displayed on the screen of the LCD 21. The barycenter ip is related to the position on the surface of the object Q to be measured. Thus, the value thereof increases in the case where the surface position of the object Q is close to the three-dimensional camera 2, and vice versa. Thus, the distance distribution can be expressed by displaying the variable density image with the barycenter ip as density data.

FIG. 11 is a diagram showing the concept of the temporal barycenter Npeak.

The temporal barycenter Npeak is the barycenter ip on the time axis for 32 light-receiving data in time series obtained by 32 sampling sessions. The sampling numbers 1 to 32 are assigned to the 32 light-receiving data of the respective pixels. For example, the ith light-receiving data is expressed as xi, where i is an integer of 1 to 32. In this case, i indicates a frame number as counted from the time when a pixel enters the effective light-receiving area Ae.

The barycenter ip for the 1st to 32nd light-receiving data x1 to x32 is determined by dividing the total sum Σi·xi of i·xi by the total sum Σxi of xi. Thus, $$ip = \frac{\sum_{i=1}^{32} i \cdot xi}{\sum_{i=1}^{32} xi}$$

The barycenter calculation circuit 73 calculates the barycenter ip for each pixel based on the data read from the memory 63. However, the data read from the memory 63 is not used as it is, but the value (0, if the particular value is negative) obtained by subtracting the steady light data ks from each data is used. In other words, the light-receiving data output from the image sensor 53 is offset by subtracting an amount corresponding to the steady light data ks.

The barycenter ip thus calculated is sequentially stored in the display memory 74 and displayed on the screen of the LCD 21. The barycenter ip, which is related to the surface position of the object Q to be measured, increases in value in the case where the surface position of the object Q is close to the three-dimensional camera 2, and vice versa. Thus, by displaying the variable density image with the barycenter ip of each pixel of the image sensing surface S2 as a density data, the distance distribution can be visualized as the result of measurement.

Now, a method of thinned-out read operation of the image sensor 53 will be explained.

Figure 13A:
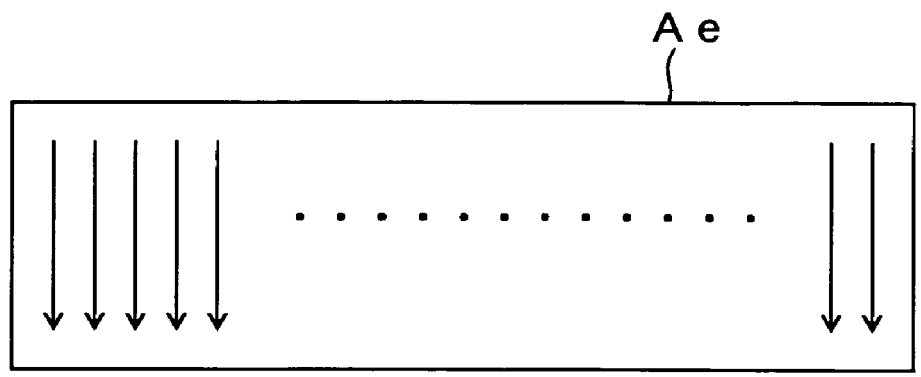
FIG. 13A is a diagram for explaining a method of reading by vertical scanning of the light-receiving area.
Figure 13B:
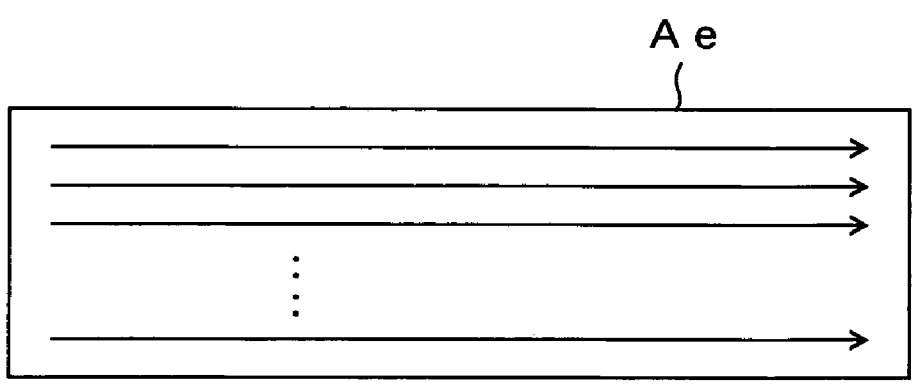
FIG. 13B is a diagram for explaining a method of reading by horizontal scanning of the light-receiving area.

FIG. 12 is a model diagram showing a configuration of the image sensor 53, and FIGS. 13A and 13B are diagrams for explaining the method of reading the light-receiving area Ae.

The image sensor 53 is an image sensing device of a type of the X-Y address scanning type in which the light-receiving information is read out by designating the pixels g of the image sensing surface S2 sequentially, and is capable of reading an arbitrary range of each pixel g by controlling a switch. Generally, by inputting a shift signal at a predetermined timing to a digital shift register constituting the vertical scanning circuit 531 and the horizontal scanning circuit 532, the line-by-line read operation is carried out. The line is a string of pixels along the horizontal direction. According to this embodiment, the horizontal direction is the one corresponding to the main scanning direction of scanning the object Q, and the vertical direction is the one corresponding to the subscanning direction (the direction of deflection of the slit light). Since the orientation of the image sensor 53 can be changed in accordance with the configuration of the optical system, however, the vertical direction referred to herein is not always coincident with the vertical direction in the real space.

The image sensor 53 includes a scan start set register 533 for giving an initial register value indicating the scan start line for the vertical scanning circuit 531, whereby the operation of reading the effective light-receiving area Ae (stripe image) is realized. Also, a skip read register 535 for giving a thin-out amount for horizontal shift is provided for the horizontal scanning circuit 532. As a result, the thinned-out read operation in the main scanning direction is realized.

A data signal sgn1 indicating the scan start position and a data signal sgn2 indicating the scan end position are input to the scan start set register 533, thereby the scan start set register 533 designates the position in the effective light-receiving area Ae from which the picked-up image (stripe image) is to be read. A data signal sgn3 indicating the skip read amount through a register 535 is input to the horizontal scanning circuit 532, thereby the horizontal scanning circuit 532 designates the thin-out ratio in the main scanning direction. In the normal mode, however, the skip read amount is set to zero to eliminate the thin-out operation.

Also, with the increase in the number of pixels of the image sensing surface S2, the number of bits of the data signal sgn1 increases. Therefore, a decoder 534 for the data signal sgn1 is desirably provided for reducing the input terminals. At the read start point, the contents of the scan start set register 533 are transferred in parallel to the vertical scanning circuit 531 thereby to set the scan start position and the scan end position.

The stripe image is read out not by repeating the horizontal scanning but by repeating the vertical scanning.

Specifically, in the prior art, as shown in FIG. 13B, one line along the length direction of the slit light is read by one horizontal scanning, and by repeating this process, the stripe image Ae is read out. According to this embodiment, in contrast, as shown in FIG. 13A, one line along the vertical direction is read out by one vertical scanning, and this process is repeated while shifting the position horizontally thereby to read out the stripe image Ae.

First, the image sensor 53 conducts the vertical scanning from the start position to the end position along the first column, i.e. on the first line along the vertical direction. In this way, a photo-electric conversion signal is output from the 33 pixel strings (=32+1) arranged in vertical direction. However, the photo-electric conversion signal only for 32 pixels out of the 33 pixels are stored in the memory 63. Then, the horizontal read position is shifted in accordance with the skip read amount set in the skip read register 535, followed by the vertical scanning again thereby to output a photo-electric conversion signal for 33 pixels. By repeating this operation, an image is output with the stripe image at a designated position thinned-out.

The read operation performed in the manner described above can complete the read operation of one frame within a much shorter time (the number of lines to be read is divided by the number of all areas) than when reading the images from all areas of the image sensing surface S2.

The reason why the read operation is performed in the range of the 33 pixels arranged in the vertical direction is as follows.

In the MOS sensor, an area, once read out, is reset to start for the next electric charge accumulation, while the electric charge accumulation is not interrupted in the area which has not been read. This poses no problem as far as the area next to be read is the same. In the case where a different area is to be read, however, image information of different accumulation time comes to coexist after the nth read operation and the (n+1)th read operation. Specifically, in the three-dimensional measurement by the light projection method, the effective light-receiving area Ae required to be read is shifted in the subscanning direction (direction perpendicular to the image sensing surface) with the deflection of the slit light beam U. Thus, the image read out from the area involving the nth and (n+1)th double read operations is associated with the accumulation time from the preceding (nth) read operation to the current (n+1)th read operation, while the image read newly from the area by the shift of the effective light-receiving area Ae is subjected to continuous photo-electric conversion from the first image sensing session. According to this embodiment, the area to be read is set to contain both the area currently required and the area next required. By doing so, the electric charge accumulation is always cleared in the preceding session for the area requiring the next read operation, thereby avoiding the problem that an image is fetched from the pixel of a different accumulation time.

Figure 14:
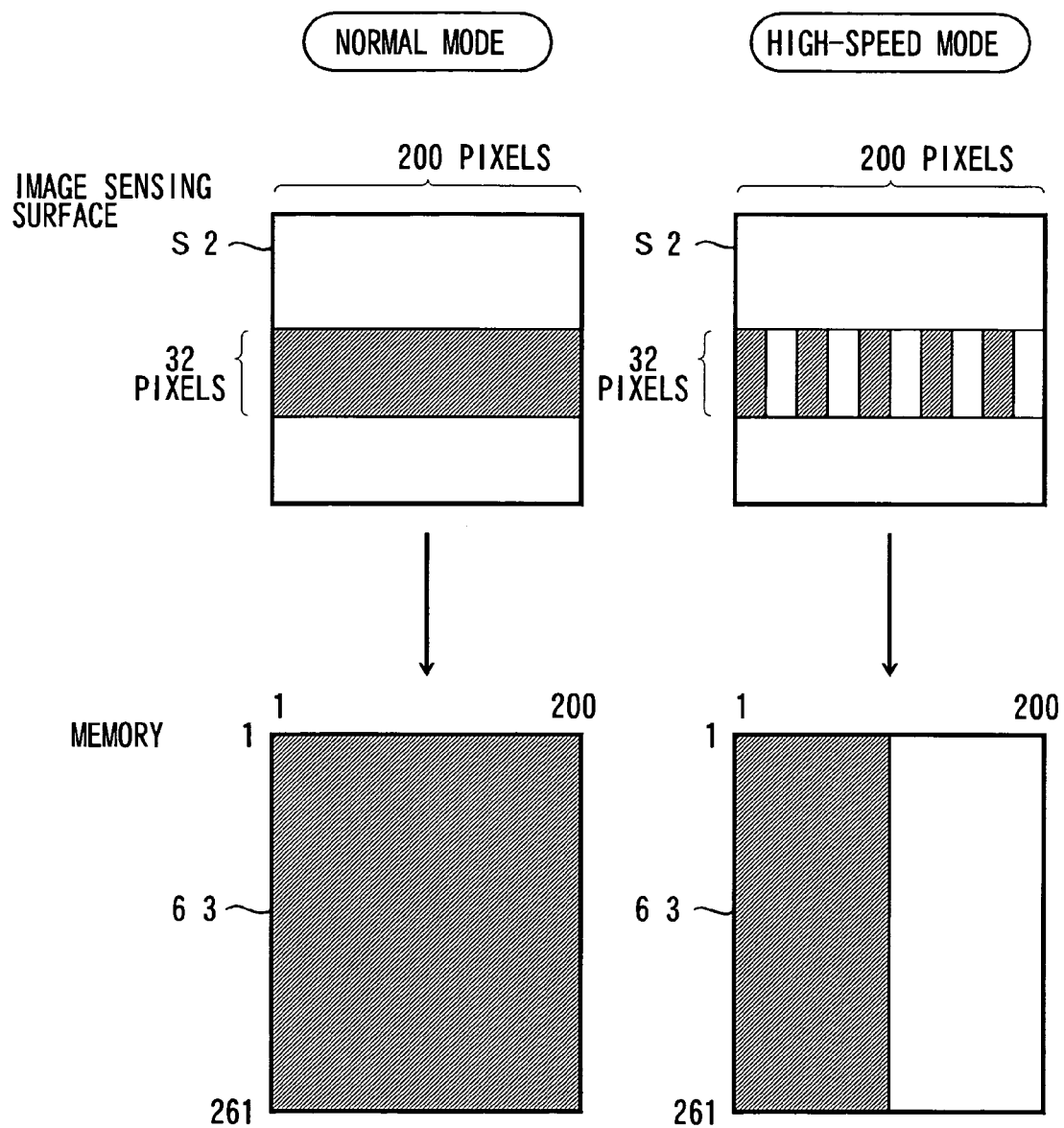
FIG. 14 is a diagram showing the manner in which a memory is used.

FIG. 14 is a diagram showing the manner in which the memory is used.

In a normal mode, the data of 200 pixels per line in the horizontal direction of the image sensing surface S2 are written in the memory 63 in the order of being read from the image sensor 53. In high-speed mode, on the other hand, the data read out by being thinned out along the horizontal direction of the image sensing surface S2 are sequentially written in the order of being read out with the addresses thereof arranged closely to each other.

The operation of the three-dimensional camera 2 and the host 3 will be explained below together with the measuring steps. Assume that the number of sampling points for measurement is 200×262 for a normal mode and 100×262 for a high-speed mode. In other words, the number of pixels is 262 and the substantial number of frames N is 231 along the width of the slit U on the image sensing surface S2.

A user (image sensing operator) sets the desired operation mode in accordance with the guide indicated on the operating screen displayed by the LCD 21. After that, while watching the color monitor image, the operator determines the position and angle of the camera and sets the angle of view. In the process, the zooming scanning is carried out as required.

In the three-dimensional camera 2, the diaphragm of the color sensor 54 is not adjusted, but the color monitor image with the exposure controlled by the electronic shutter function is displayed, so that the diaphragm is kept open so as to secure as much incident light of the image sensor 53 as possible.

Figure 15:
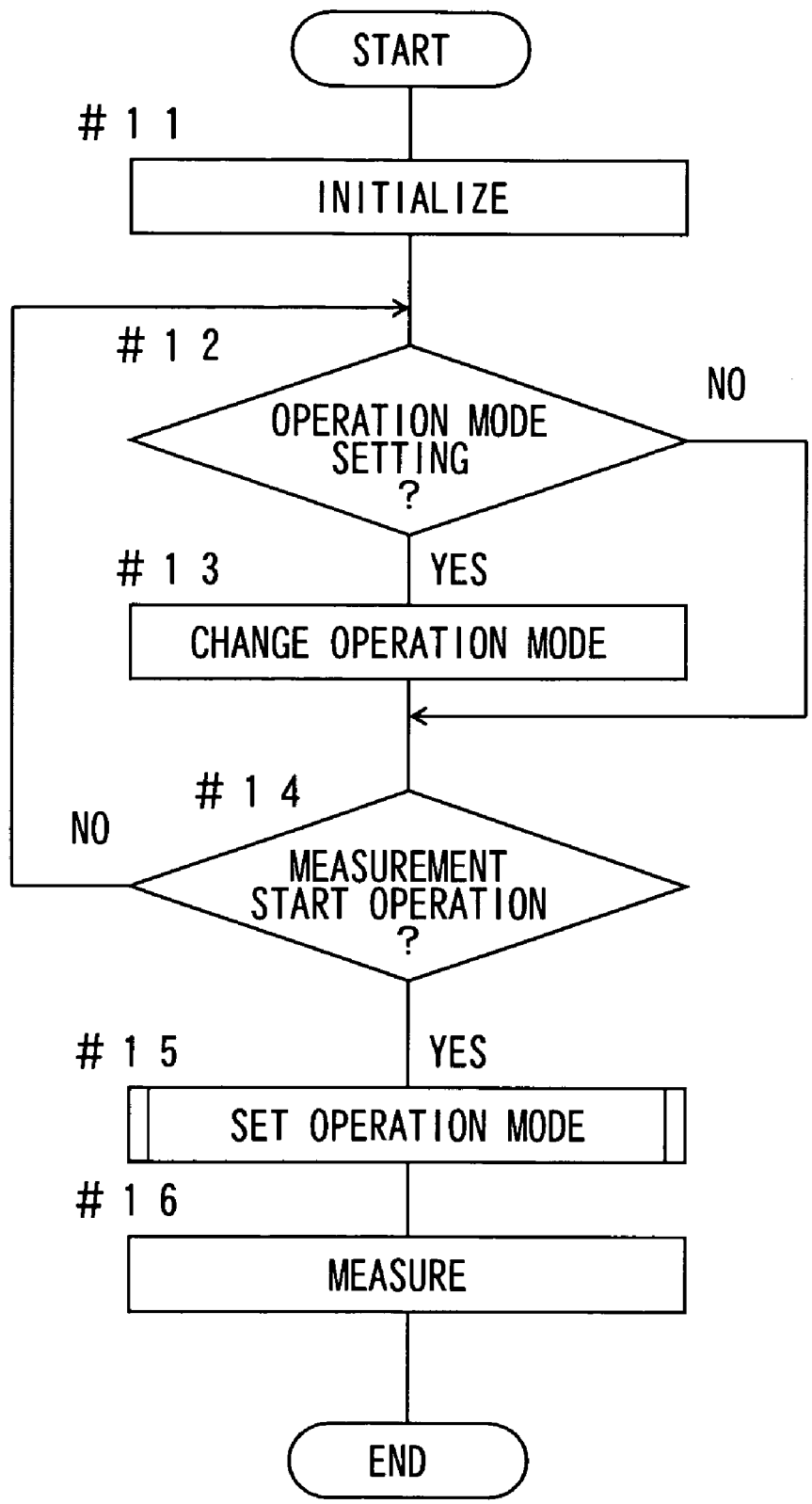
FIG. 15 is a flowchart schematically showing the operation of the three-dimensional camera.

FIG. 15 is a flowchart showing the concept of operation of the three-dimensional camera 2.

After initialization with power switched on, the three-dimensional camera 2 stands by waiting for the operation by the user (#11). Once the process is performed for setting an operation mode, the contents of mode change are stored (#12, #13). Upon instruction to start measurement by turning on the shutter button 27, the operation mode is set and measurement is conducted (#14 to #16).

Figure 16:
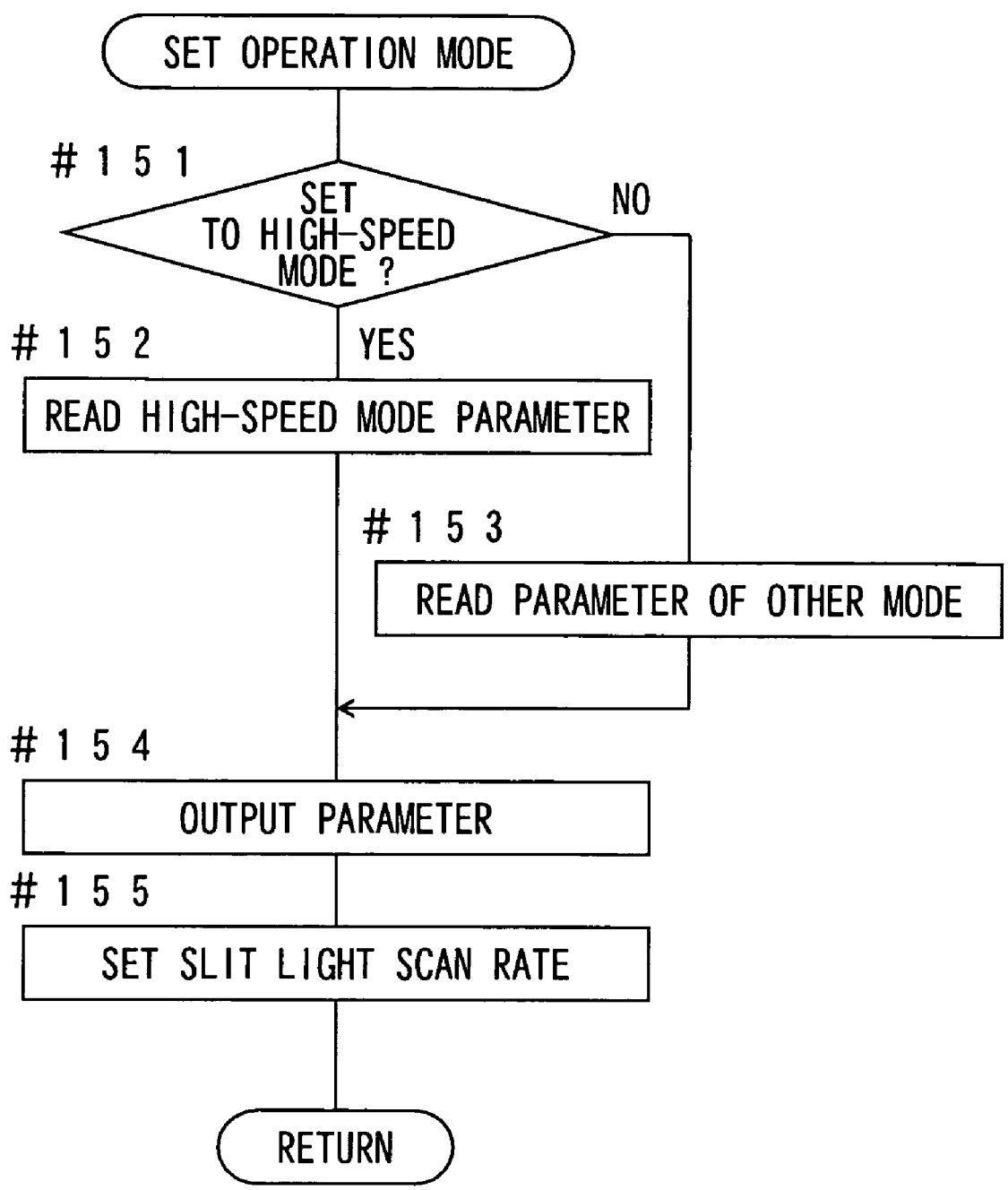
FIG. 16 is a flowchart of an operation mode setting subroutine.

FIG. 16 is a flowchart for the operation mode setting subroutine.

In the case where the high-speed mode is set, the parameter for the thinned-out read operation described above is read from a control data ROM (#151, #152). In the case where another mode is set, the parameter for the particular mode is read out (#151, #153). The parameter thus read is applied to the object to be controlled, after which the position of the virtual surface providing a reference surface for measurement is determined in accordance with the zooming and focusing conditions. Then, the deflection angle range and the scanning rate of the slit light beam U are set (#154, #155). By the way, the operation mode is set either by switch or button operation or by remote control from an external unit.

Figure 17:
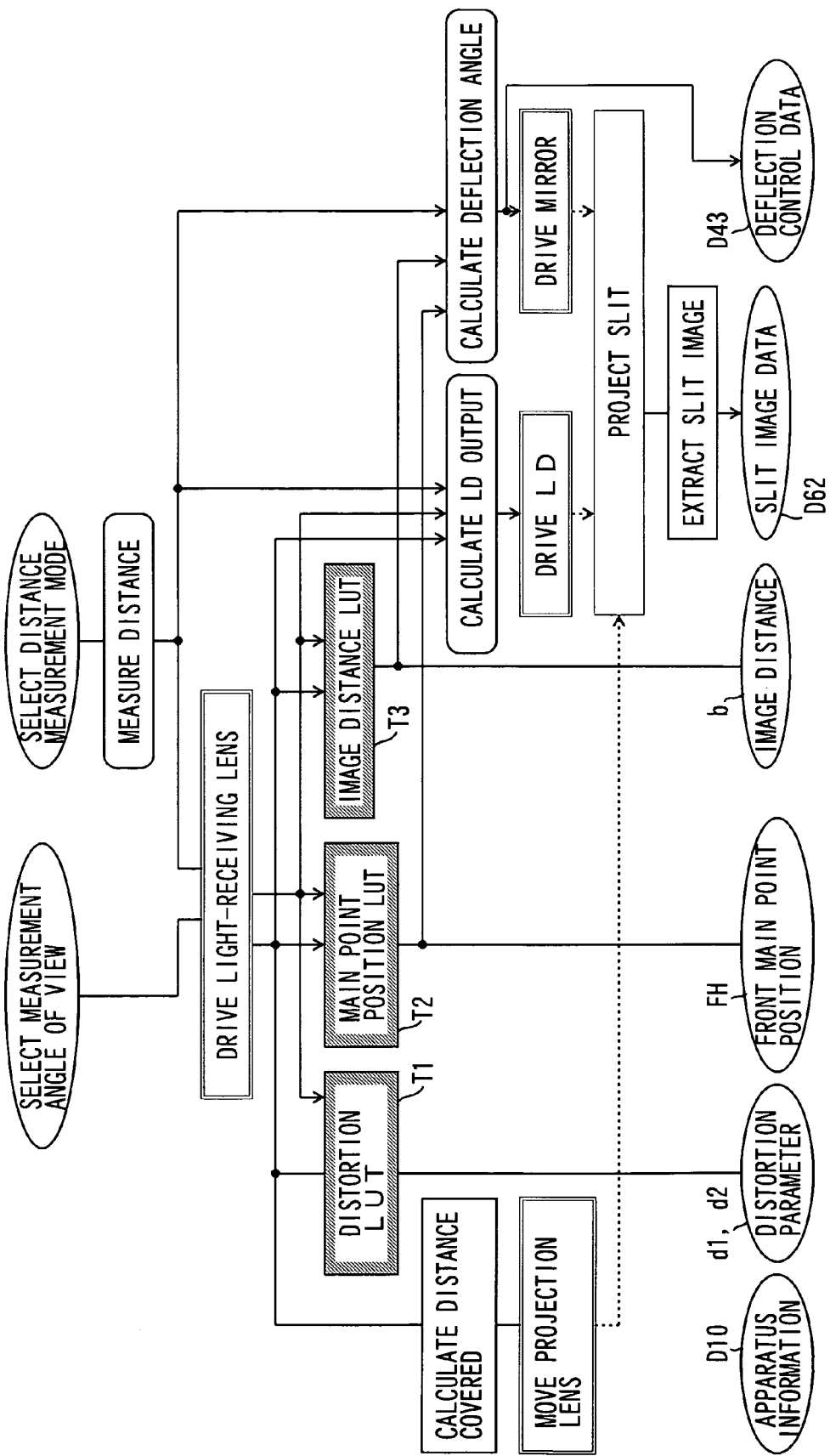
FIG. 17 is a diagram showing the data flow in the three-dimensional camera.
Figure 18:
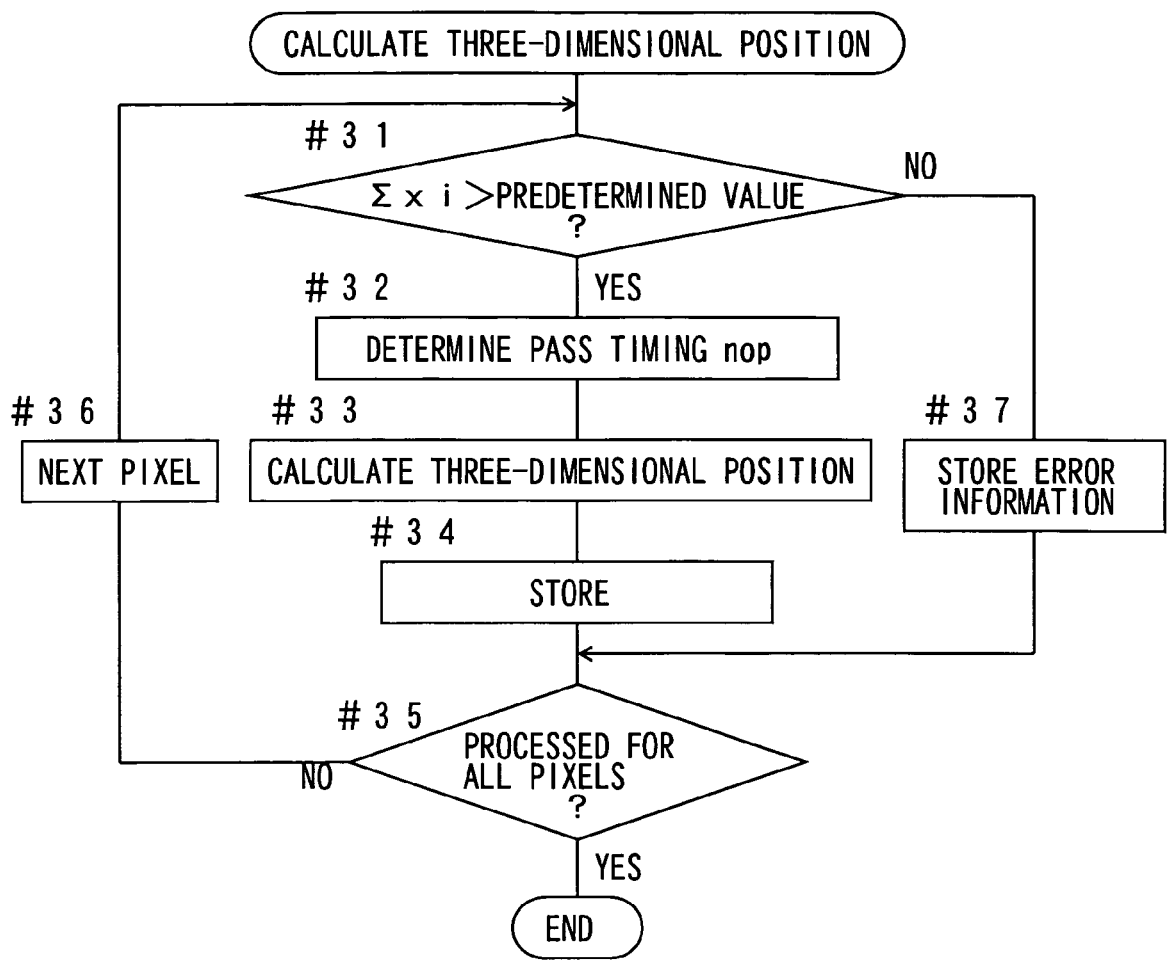
FIG. 18 is a flowchart showing the processing steps of the three-dimensional position calculation in a host.
Figure 19:
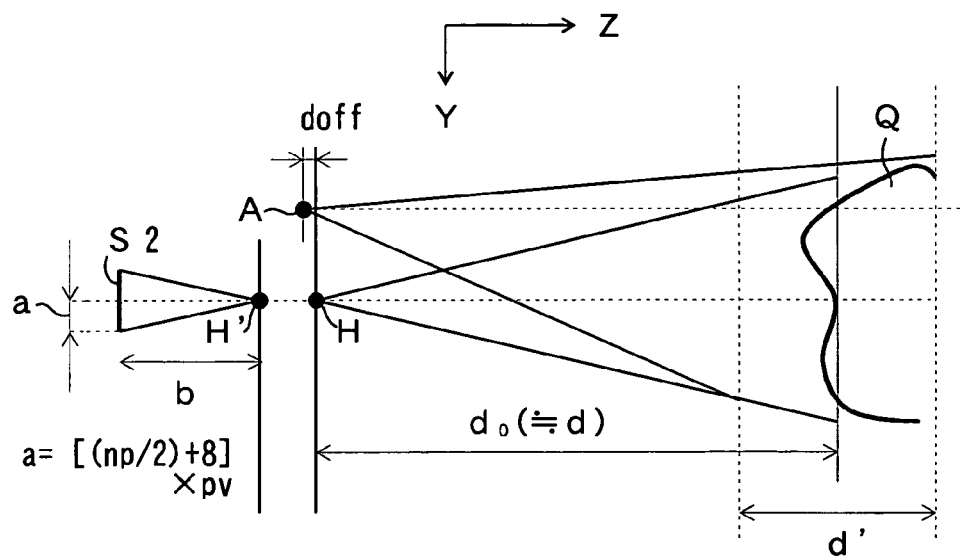
FIG. 19 is a diagram showing a relationship between each point in an optical system and an object.

FIG. 17 is a diagram showing the data flow in the three-dimensional camera 2, FIG. 18 is a flowchart showing the processing steps of three-dimensional position calculation in the host 3, and FIG. 19 is a diagram showing the relationship between each point in the optical system and the object Q.

In accordance with the user operation of selecting the angle of view (zooming), the variator portion of the zoom unit 51 is moved. Also, the focusing portion is moved as manual or automatic focusing. An approximate distance do with the object is measured in the process of focusing.

In response to the lens drive of the light-receiving system described above, the distance covered by the variator lens 422 on the projection side is calculated by a calculation circuit not shown, and based on the calculation result, the movement of the variator lens 422 is controlled.

The system controller 61 reads the output (supply amount Ed) of the focusing encoder and the output (zoom increment fp) of the zooming encoder through the lens controller 58. Within the system controller 61, a distortion table T1, a main point position table T2 and an image distance table T3 are referred to, so that the image sensing condition data corresponding to the supply amount Ed and the zoom increment fp are output to the host 2. The image sensing condition data include the distortion parameter (lens distortion correction factors d1, d2), the front main point position FH and the image distance b. The front main point position FH is expressed as the distance between the front end point F and the front main point H of the zoom unit 51. The front terminal point F is fixed, and therefore the front main point H can be specified by the front main point position FH.

The system controller 61 calculates the output (laser intensity) of the semiconductor laser 41 and the deflection conditions (scan start angle, scan end angle and deflection angle speed) of the slit light beam U. The method of this calculation will be described in detail.

First, assuming that a flat object exists in an approximate object distance do, the projection angle is set so as to receive the reflected light at the center of the image sensor 53. The activation with pulses for calculation of the laser intensity described below is effected at the projection angle thus set.

Then, the laser intensity is calculated. In calculating the laser intensity, the human body may be measured and therefore security should be considered. First, the LD41 is activated with pulses with minimum intensity of LDmin thereby to fetch the output of the image sensor 53. Among the signals for a plurality of pixels thus fetched, the ratio between the maximum value MAX [Son(LDmin)] and the proper level Styp is calculated and a provisional laser intensity LD1 is set as follows.

$$LD1 = LDmin \times Styp/MAX[Son(LDmin)]$$

Then, the output of the image sensor 53 is fetched again by activation with pulses at the laser intensity of LD1. In the case where the signal [Son(LD1)] thus fetched is a proper level Styp or a value about it, LD1 is determined as the laser intensity LDs. Otherwise, a new provisional laser intensity LD1 is set based on the laser intensity LD1 and MAX[Son(LD1)], and the output of the image sensor 53 is compared with the proper level Styp. Until the output of the image sensor 53 reaches a value within the tolerance, the provisional setting of the laser intensity and the confirmation of the appropriateness are repeated. By the way, the output of the image sensor 53 is fetched for the whole image sensing surface 2. This is by reason of the fact that the light-receiving position of the slit light beam U cannot be easily estimated with high accuracy from the passive distance calculation with the auto focusing (AF). The charge accumulation time of the image sensor 53 is the time corresponding to one field (1/60 seconds, for example), and is longer than the accumulation time for the actual measurement. As a result, the sensor output equivalent to the actual measurement is obtained by activation with pulses.

Then, the distance d with the object is determined by triangulation from the projection angle and the light-receiving position of the slit light beam U as of the time when the laser intensity is determined.

Finally, the deflection conditions are calculated based on the distance d with the object determined as above. The calculation of the deflection conditions takes into account the offset doff in Z direction (along the depth) between the front main point H of the light-receiving system providing a measurement reference point of the object distance d and the projection start point A. Also, in order to secure the measurable distance range d' at the end in scanning direction as at the central portion, a predetermined amount (eight pixels, for example) of overscan is conducted. The scan start angle th1, the scan end angle th2 and the deflection angular speed ω are given as follows:

$$th1 = \tan^{-1}[\beta \times pv(np/2+8)+L)/(d+doff)] \times 180/\pi$$

$$th2 = \tan^{-1}[-\beta \times pv(np/2+8)+L)/(d+doff)] \times 180/\pi$$

$$\omega = (th1 - th2)/np$$

where β is the image sensing magnification (=d/effective focal length freal), pv the pixel pitch, np the number of effective pixels along Y direction on the image sensing surface S2, and L the base line length.

Under the conditions thus calculated, the main light emission is started, and the object Q is scanned (slit projection), so that the data D62 stored in the output memory 64 are sent to the host 2 through the output processing circuit 62, the memory 63 and the center-of-gravity calculation circuit 73. At the same time, the system information D10 indicating the deflection conditions (deflection control data) and the specification of the image sensor 53 are also sent to the host 3. Table 1 shows a summary of the main data sent to the host 3 from the three-dimensional camera 2.

TABLE 1

|  |  | Data contents | Data range |
|---|---|---|---|
| Measurement data | | Σxi  200 × 200 × 13 bit | |
| | | Σi · xi  200 × 200 × 18 bit | |
| Imaging conditions | | Image distance b | 0.0000~200.00 |
| | | Front main point position FH | 0.00~300.00 |
| | | Slit deflection start angle th1 | |
| | | Deflection angular speed ω | |
| Apparatus information | | Number of pixels for measurement (number of sampling times in X & Y directions) | 1~ |
| | | Sensor pixel pitch pu, pv | ~0.00516~ |
| | | Projection system position (around X, Y, Z axes) | 0.00~±90.00 |
| | | Projection system position (along X, Y, Z axes) | 0.00~±300.00 |
| | | Lens distortion correction factor d1, d2 | |
| | | Sensor center pixel u0, v0 | 0.00~256.00 |
| 2-dimensional image | | R plane  512 × 512 × 8 bit | 0~255 |
| | | G plane  512 × 512 × 8 bit | 0~255 |
| | | B plane  512 × 512 × 8 bit | 0~255 |

As shown in FIG. 18, the three-dimensional position calculation process is executed in the host 3, whereby a three-dimensional position (coordinates X, Y, Z) with 200 (or a fewer number in the high-speed mode) sampling points (pixels) per line is calculated. The sampling point is the intersection between the camera line of view (straight line connecting a sampling point and the front main point H) and the slit surface (the optical axis plane of the slit light beam U irradiating the sampling point).

In FIG. 18, it is first determined whether the total sum Σxi of xi sent from the three-dimensional camera 2 is more than a predetermined value or not (#31). In the case where xi is small, i.e. in the case where the total sum Σxi of the slit light components is less than a predetermined reference, a considerable error exists. For the pixel involved, therefore, the three-dimensional position is not calculated, but data indicating "error" is set and stored (#37). In the case where Σxi exceeds a predetermined value, on the other hand, a sufficient accuracy can be obtained and therefore the three-dimensional position is calculated.

Prior to the calculation of the three-dimensional position, the timing nop at which the slit light beam U passes is calculated (#32). The pass timing nop is determined by calculating (Σi·xi)/(Σxi) for i of 1 to 32, determining the barycenter ip (temporal barycenter Npeak), and adding the line number thereto.

In this way, the barycenter ip thus calculated represents the timing in 32 frames for which the pixel output is obtained, and therefore by adding the line number, it can be converted into the pass timing nop from the scanning start. Specifically, the line number is 32 for the pixels of the line 32 calculated first, and 33 for the next line 33. Each time the line of the intended pixel g advances, the line number increases by one. However, these values can be replaced by another proper value. The reason is that in calculating the three-dimensional position, the rotational angle (the1) around the X axis or the angular speed (the4) around the X axis in equation (3) constituting a coefficient and described later can be properly set by calibration.

Then, the three-dimensional position is calculated (#33). The three-dimensional position thus calculated is stored in the memory area corresponding to the particular pixel (#34), followed by a similar process being performed for the next pixel (#36). Upon complete processing for all the pixels (YES in #35), the routine is terminated.

Now, a method of calculating the three-dimensional position will be explained.

The camera view equations are given by (1) and (2).

$$(u-u0)=(xp)=(b/pu) \times [X/(Z-FH)] \qquad (1)$$

$$(v-v0)=(yp)=(b/pv) \times [Y/(Z-FH)] \qquad (2)$$

where b is the image distance, FH the front main point position, pu the pixel pitch in horizontal direction on the image sensing surface, pv the pixel pitch in vertical direction on the image sensing surface, u the pixel position in horizontal direction on the image sensing surface, u0 the central pixel position in horizontal direction on the image sensing surface, v the pixel position in vertical direction on the image sensing surface, and v0 the central pixel position in vertical direction on the image sensing surface.

The slit surface equations is given by (3).

$$\begin{bmatrix} \cos(the3) & -\sin(the3) & 0 \\ \sin(the3) & \cos(the3) & 0 \\ 0 & 0 & 1 \end{bmatrix} \begin{bmatrix} \cos(the2) & 0 & \sin(the2) \\ 0 & 1 & 0 \\ -\sin(the2) & 0 & \cos(the2) \end{bmatrix} \qquad (3)$$

$$\begin{bmatrix} 1 & 0 & 0 \\ 0 & \cos(the1+the4 \cdot nop) & -\sin(the1+the4 \cdot nop) \\ 0 & \sin(the1+the4 \cdot nop) & \cos(the1+the4 \cdot nop) \end{bmatrix}$$

$$\begin{bmatrix} 0 \\ 1 \\ 0 \end{bmatrix} [x \quad Y-L \quad Z-s] = 0$$

the1: Rotation angle around X axis
the2: Inclination angle around Y axis
the3: Inclination angle around Z axis
the4: Angular speed around X axis
nop: Pass timing
(=temporal barycenter ip+line No.)
L: Base line length
s: Offset at origin A The geometric distortion is dependent on the angle of view. The distortion occurs substantially about the central pixel. The distortion amount, therefore, can be expressed by the function of the distance from the central pixel. In this case, the distortion amount is approximated by the tertiary function of the distance. Assume that the secondary correction factor is d1 and the tertiary correction factor is d2. The pixel position u', v' after correction is given by equations (4) and (5).

$$u'=u+d1 \times t2^2 \times (u-u0)/t2+d2 \times t2^3 \times (u-u0)/t2 \qquad (4)$$

$$v'=v+d1 \times t2^2 \times (v-v0)/t2+d2 \times t2^3 \times (v-v0)/t2 \qquad (5)$$

$$t2=(t1)^{-2}$$

$$t1=(u-u0)^2+(v-v0)^2$$

In equations (1) and (2) described above, u' is substituted into u, and v' into v, whereby the three-dimensional position taking into the distortion into account can be determined. By the way, for the calibration, refer to the detailed disclosure in the Institute of Electronics, Information and Communication Engineers literature PRU 91-223, "Geometric correction of image without positioning the camera," by Onoda and Kanaya, and "High-accuracy calibration method of range finder based on three-dimensional model of optical system," by Ueshiba, Yoshimi and Ohshima, IEICE journal D-II Vol. J74-D-II No. 9, pp. 1227-1235, September '91.

In the embodiment described above, the ratio of the thinned-out read operation of the image sensor 53 can be arbitrarily changed according to the setting of the skip read amount applied to the horizontal scanning circuit 532.

In the case where the skip read amount is one pixel, for example, the signal is thinned out at the rate of every other pixel, so that the read time and the data amount are reduced to one half of those in the normal mode.

As described above, according to the first embodiment, the time required for three-dimensional data input of a predetermined angle of view can be shortened without reducing the distance range capable of three-dimensional data input and the resolution. Also, the number of sampling sessions (resolution) in the main scanning direction can be selected by the user in accordance with applications.

In the embodiment described above, the slit light is used as the detection light. Instead, the spot light may be used for scanning by deflecting it in the main scanning direction and the subscanning direction. Also, in place of the MOS area sensor as the image sensor 53, the CCD area sensor can be used in the case where the only purpose is to reduce the data amount. In such a case, all the pixels, after being read out once, can be stored in every other pixel.

The three-dimensional position can be calculated by the three-dimensional camera 2 instead of the host 3. Also, it is possible to calculate the three-dimensional position by a look-up table method. In the optical system 50 on the light-receiving side, the image sensing magnification can be changed by replacement lenses instead of by the zoom unit 51.

Second Embodiment

The basic configuration of the second embodiment is the same as that of the first embodiment. Specifically, FIGS. 1 to 5B, 7A to 10 and 17 to 19 and the description thereof applicable to the first embodiment are also applicable to the second embodiment. Only the portions of the second embodiment different from the first embodiment will be explained below.

The first embodiment refers to both the normal mode and the high-speed mode of the method of reading the frame by the image sensor 53. In the second embodiment, on the other, only the normal mode will be described.

Figure 20:
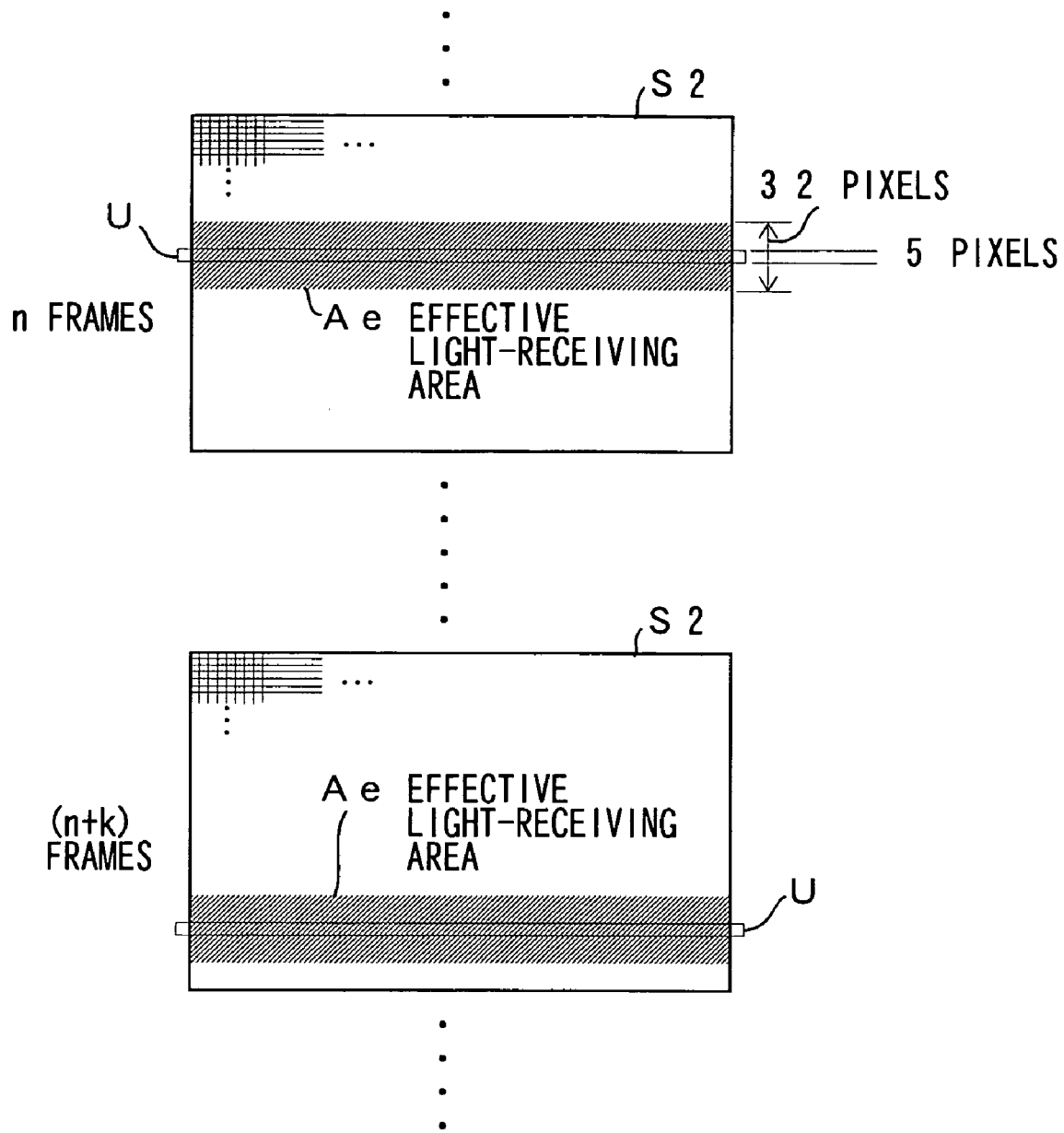
FIG. 20 is a diagram showing the read range of the image sensor.

FIG. 20 is a diagram showing the read range of the image sensor, and corresponds to FIG. 6 of the first embodiment. As shown in FIG. 20, in the normal mode, the thinned-out read operation is not performed unlike in the first embodiment, but all the data in the effective light-receiving area Ae are read out. Specifically, the skip read amount is set to zero in the skip read register 535 of FIG. 12, thereby reading the whole of the effective light-receiving area Ae without thin-out. As a result, each frame of the image sensing surface S2 shown in FIGS. 7A and 7B contains the light-receiving data for 32 lines (32×200 pixels).

In the second embodiment, as explained with reference to the first embodiment, the vertical read method is used for reading data from the effective light-receiving area Ae in the image sensor 53. According to the vertical read method, the data of each pixel in the effective light-receiving area Ae sequentially continues to be read along the same direction as the direction in which the slit light beam U moves on the image sensing surface S2. In the horizontal read method, by contrast, the data of each pixel are read out along the direction perpendicular to the direction in which the slit light beam U moves on the image sensing surface S2. By applying the vertical read method, as compared with the horizontal read method, the accuracy of the calculation of the barycenter is improved. The reason for this will be explained with reference to FIGS. 21 to 30.

First, it will be explained why the accuracy of the calculation of the temporal barycenter is improved by the application of the vertical read method.

Figure 21:
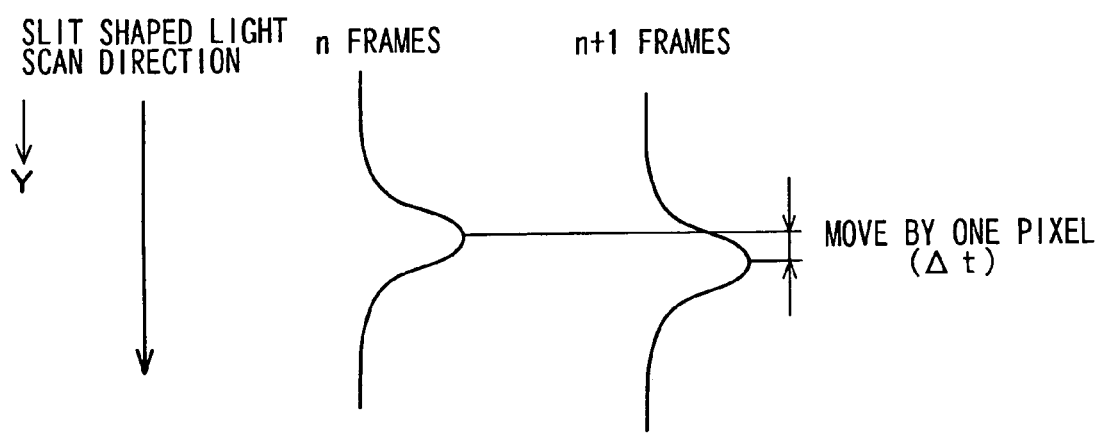
FIG. 21 is a diagram showing the direction of movement and the distance covered by the movement of the slit light on the image sensing surface.
Figure 22:
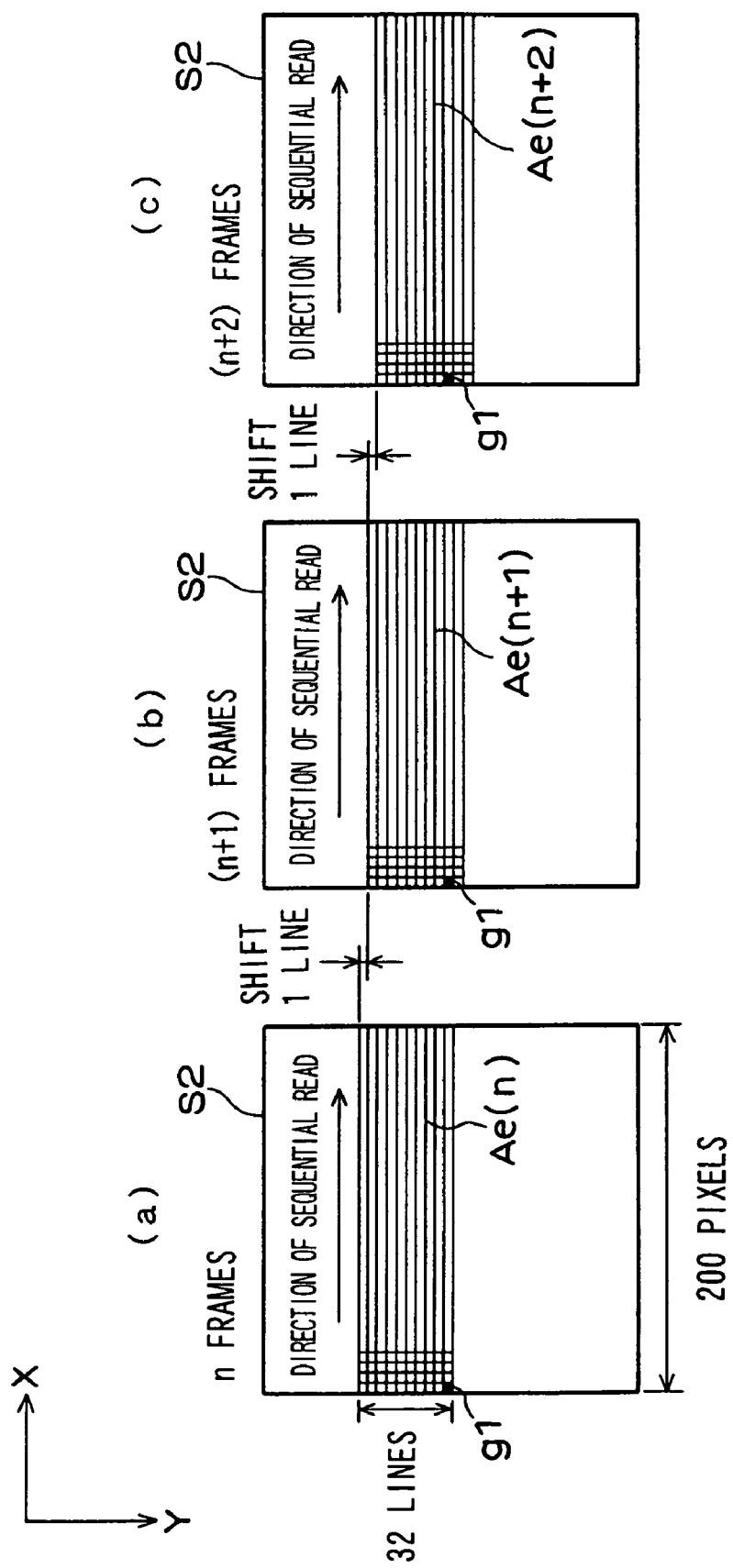
FIG. 22 is a diagram for explaining the timing of reading an intended pixel in the effective light-receiving area according to the horizontal read method.
Figure 23:
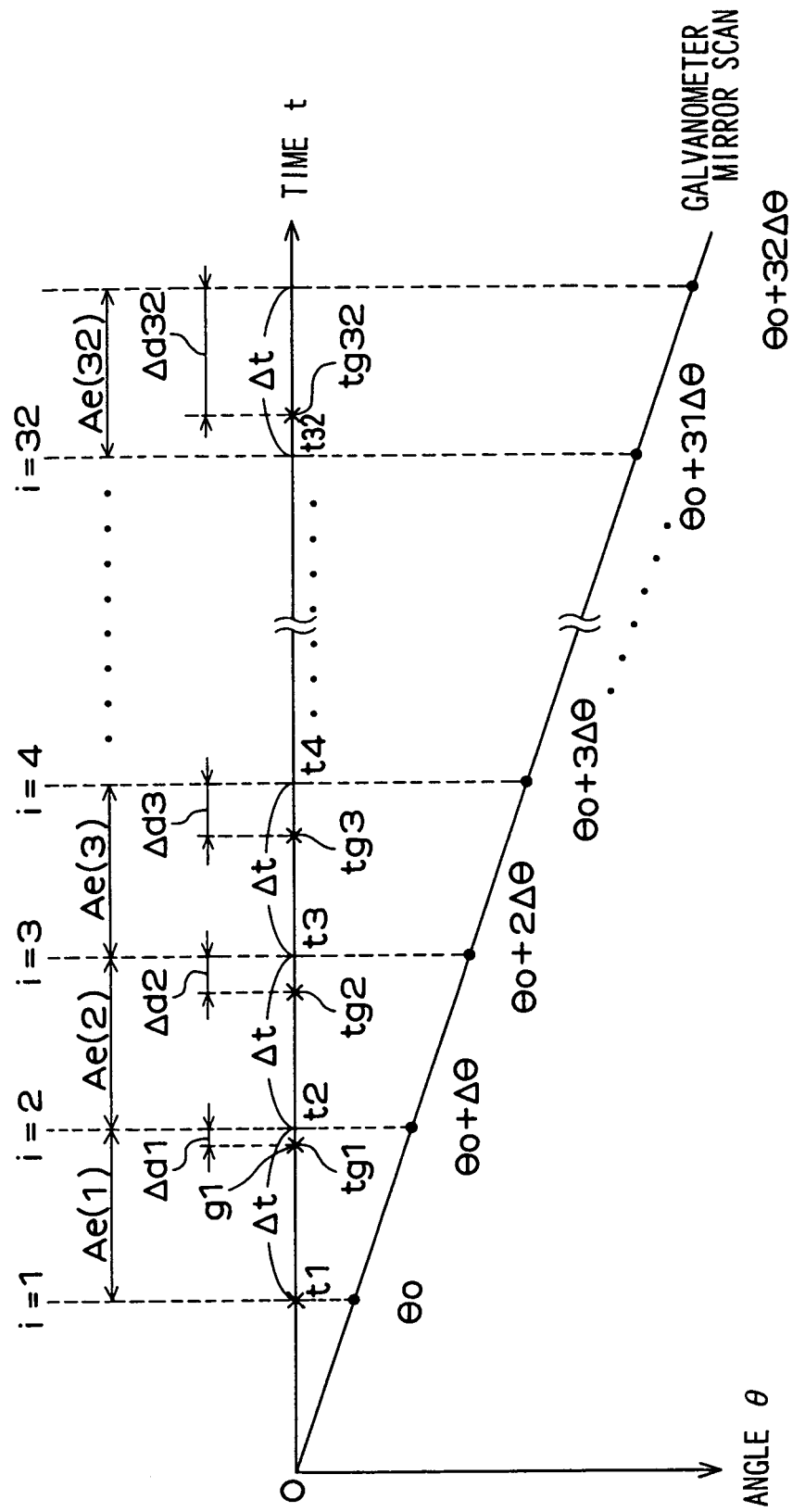
FIG. 23 is a diagram showing the deviation between the timing of reading an intended pixel in the effective light-receiving area according to the horizontal read method and the timing of shifting the effective light-receiving area by one line.
Figure 24:
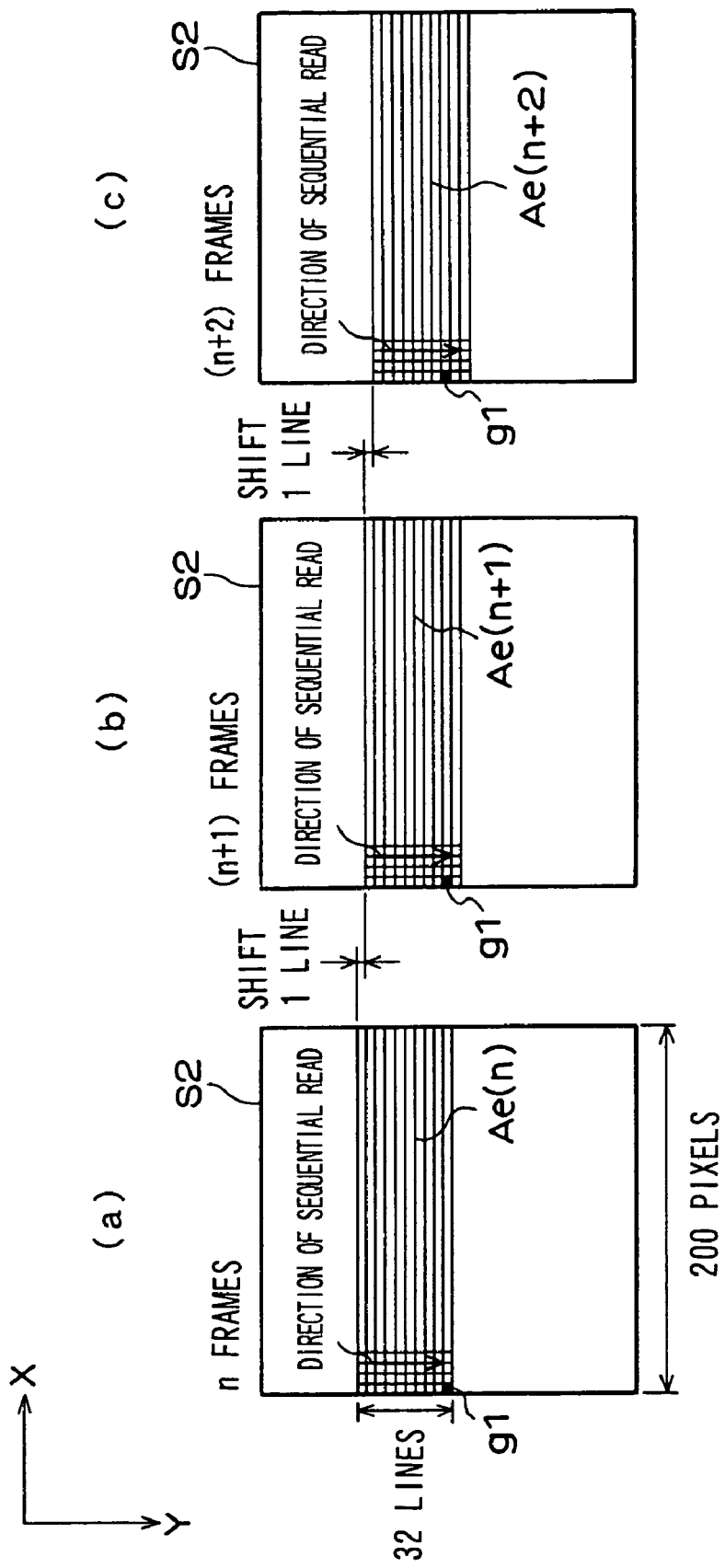
FIG. 24 is a diagram for explaining the timing of reading an intended pixel in the effective light-receiving area according to the vertical read method.
Figure 25:
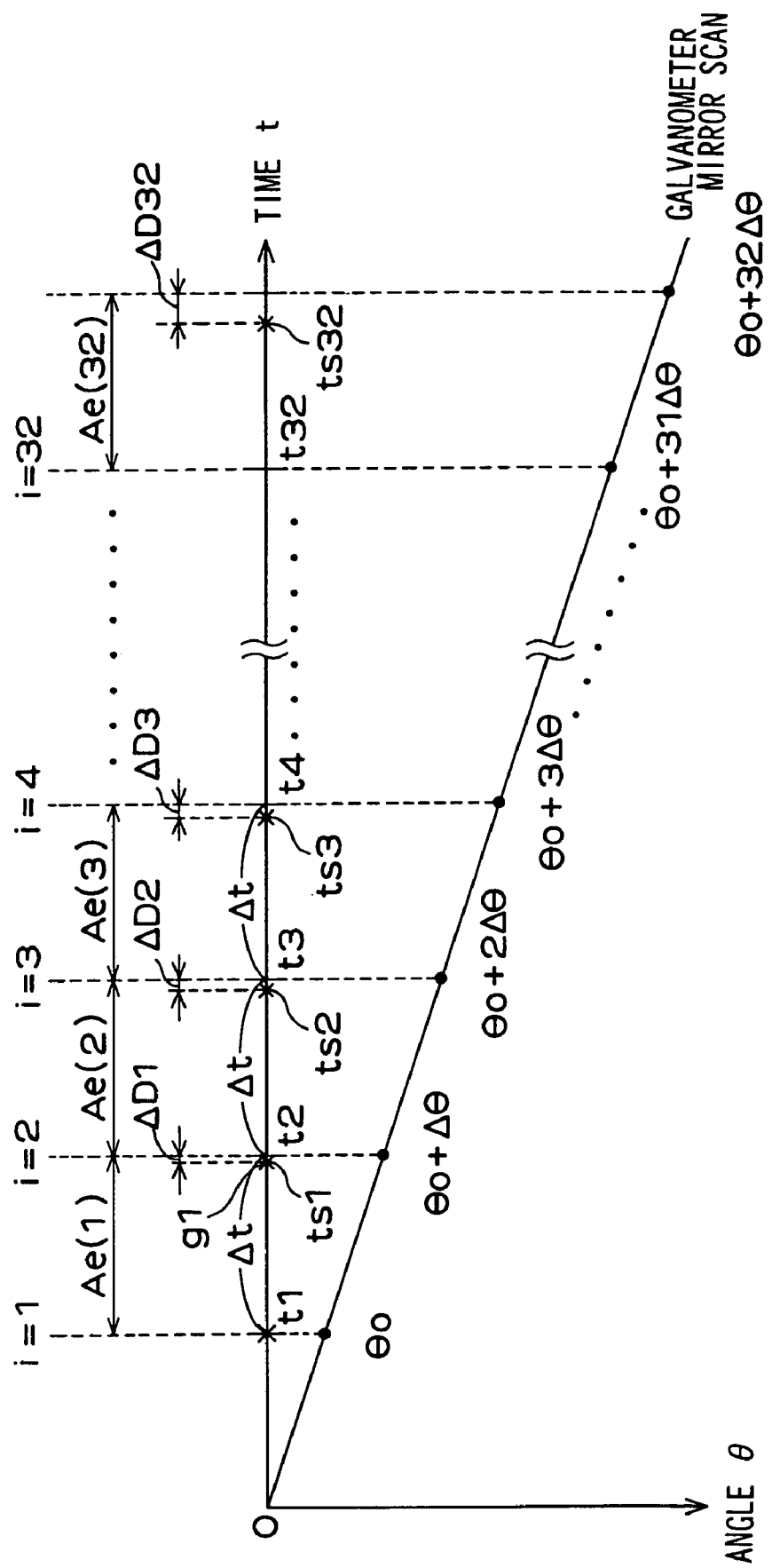
FIG. 25 is a diagram showing the deviation between the timing of reading an intended pixel in the effective light-receiving area according to the vertical read method and the timing of shifting the effective light-receiving area by one line.

FIG. 21 is a diagram showing the direction of movement and the distance covered by the movement of the slit light beam U on the image sensing surface S2, FIG. 22 is a diagram for explaining the timing of reading an intended pixel g1 of the effective light-receiving area Ae in the application of the horizontal read method, FIG. 23 is a diagram showing the deviation between the timing of reading the intended pixel g1 in the effective light-receiving area Ae and the timing of shifting the effective light-receiving area Ae by one line in an application of the horizontal read method, FIG. 24 is a diagram for explaining the timing of reading an intended pixel g1 of the effective light-receiving area Ae in an application of the vertical read method, and FIG. 25 is a diagram showing the deviation between the timing of reading the intended pixel g1 in the effective light-receiving area Ae and the timing of shifting the effective light-receiving area Ae by one line in an application of the vertical read method.

In FIGS. 22 and 24, the effective light-receiving areas Ae(n) to Ae(n+2) represent those of the nth to (n+2)th frames, respectively. In FIGS. 17 and 19, the abscissa represents the time and the ordinate the inclination angle of the galvanometer mirror 43 for deflecting the slit light beam U.

As shown in FIG. 21, upon complete reading of all the pixels, the effective light-receiving area Ae shifts by one line in Y direction. In the meantime, the slit light beam U moves by one line in Y direction (vertical direction or read direction).

In FIG. 22(a), assume that the horizontal read method is used, i.e. that the pixels of a line are sequentially read out and upon complete reading of the particular line, the pixels on the next line are sequentially read out in X direction. Until complete reading of the effective light-receiving area Ae(n), the time H (=200×32) is required from the start of reading, where H is the time required for reading one pixel. This time (200×32) H is equal to the time required for the slit light beam U to move by one line in Y direction on the image sensing surface S2 (Δt in FIG. 23).

Upon complete reading of the effective light-receiving area Ae(n), the effective light-receiving area Ae(n) shifts by one line in Y direction and assumes the effective light-receiving area Ae(n+1). For the effective light-receiving area Ae(n+1), like for the effective light-receiving area Ae(n), the horizontal read method is used for read operation. Upon complete reading, the effective light-receiving area Ae(n+1) shifts by one line in Y direction into the effective light-receiving area Ae(n+2), so that the effective light-receiving area Ae(n+2) is read out. This process of the read operation followed by shift is carried out from the first effective light-receiving area Ae(1) to the 32nd effective light-receiving area Ae(32).

In FIGS. 22(a) and 22(b), after the intended pixel g1 is read out in the effective light-receiving area Ae(n) until it is read in the effective light-receiving area Ae(n+1), the time $$199H+(200\times30)H+1H=(200\times31)H$$

is required. This is equivalent to the time between tg1 and tg2, for example, in FIG. 23.

Similarly, in FIGS. 22(b) and 22(c), until the intended pixel g1 is read out in the effective light-receiving area Ae(n+1) until it is read in the effective light-receiving area Ae(n+2), the time $$199H+200H+(200\times29)H+1H=(200\times31)H$$

is required (tg2 to tg3, for example, in FIG. 23).

Similar calculations show that the time of one period required from reading an intended pixel g1 in a given effective light-receiving area to the time of reading it is read in the next effective light-receiving area is always (200×31)H. This time of one period is the same for an arbitrary intended pixel.

In other words, the read cycle of an arbitrary intended pixel is (200×31)H. Thus, each time the effective light-receiving area Ae shifts one line in Y direction, the read timing for an intended pixel is advanced by $$(200\times32)H-(200\times31)H=200H$$

as compared with the timing of shifting the effective light-receiving area Ae by one line.

As shown in FIG. 23, the time lag ($\Delta$d1, $\Delta$d2, $\Delta$d3, . . . ) providing the deviation between the timing of reading an intended pixel in the effective light-receiving area Ae and the timing of shifting the effective light-receiving area Ae by one line increases to double, triple, quadruple, and so on progressively with the shift of the effective light-receiving area Ae, until for the Mth (M: integer) effective light-receiving area Ae(M), the time lag $\Delta$dM becomes $$\Delta dM=\{200\times(M-1)\}H$$

Thus, the time lag $\Delta$d32 of (200×31)H develops in the 32nd effective light-receiving area Ae(32).

In this way, in the horizontal read method, the time lag described above increases by the length equal to the read time of one line for each one-line shift of the effective light-receiving area Ae.

Figure 30:
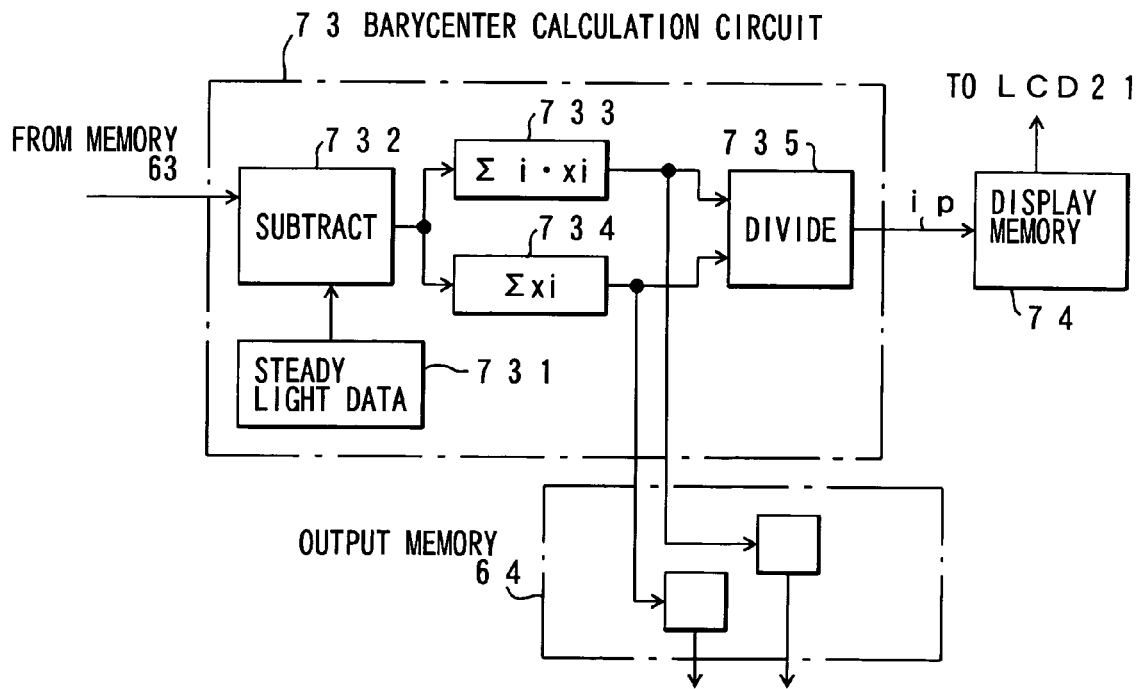
FIG. 30 is a diagram showing a configuration of a barycenter calculation circuit.

The temporal barycenter Npeak is calculated by the barycenter calculation circuit 73 of FIG. 30.

As shown in FIG. 30, the barycenter calculation circuit 73 includes a steady light data storage unit 731, a subtractor 732, a first adder 733, a second adder 734 and a divider 735. These components, which can be realized by software, can also be configured with hardware circuits in part or in whole.

In an application of the horizontal read method, the light-receiving data obtained during the period from time tg1 to tg32 (FIG. 23) is used as x1 to x32 in equation (6). Since i remains an integer, however, a considerable error comes to be included in the calculation result. For the calculation result to be reliable, the correction process is required for minimizing the deviation of the timing described above. In the case where the barycenter calculation circuit 73 is partly or wholly configured with hardware, a correction circuit is required inconveniently.

In the application of the vertical read method, in contrast, no considerable error is included in the calculation result of the temporal barycenter for the reason mentioned below.

In FIG. 24(a), assume that the vertical read method is used, i.e. that the pixels on one column along Y direction are sequentially read in Y direction and at the end of complete reading of the column, the pixels on the column next in X direction are read sequentially in Y direction. Until the complete reading of an effective light-receiving area Ae(n), the time of (200×32)H is required from the start of reading, where H is the time required for reading one pixel. This time of (200×32)H is equal to the time during which the slit light beam U moves by one line in Y direction on the image sensing surface S2 ($\Delta$t in FIG. 25).

In FIG. 24, as in FIG. 22, upon complete reading of a given effective light-receiving area Ae, the particular effective light-receiving area shifts by one line in Y direction. These read and shift operations are repeated from the first effective light-receiving area Ae(1) to the 32nd effective light-receiving area Ae(32).

After the intended pixel g1 is read in an effective light-receiving area Ae(n) until it is read in the effective light-receiving area Ae(n+1), the time $$(32\times199)H+31H=\{(200\times31)+199\}H$$

is required. This is equivalent to the time from ts1 to ts2, for example, in FIG. 25.

Also, after the intended pixel g1 is read in the effective light-receiving area Ae(n+1) until it is read in the next effective light-receiving area Ae(n+2), the time $$1H+(32\times199)H+30H=\{(200\times31)+199\}H$$

is required (equivalent to the time from tg2 to tg3, for example, in FIG. 25).

Calculating in similar fashion, one period of time after an intended pixel g1 is read in a given effective light-receiving area until it is read in the next effective light-receiving area is always given as $\{(200\times31)+199\}$ H.

This one-period time is the same for any arbitrary intended pixel.

In other words, the read cycle for an arbitrary intended pixel is given as $\{(200\times31)+199\}$ H, and each time the effective light-receiving area Ae shifts by one line in Y direction, the read timing is advanced by $$(200\times32)H-\{(200\times31)+199\}H=1H$$

The time lags $\Delta$D1, $\Delta$D2, $\Delta$D3 and so on providing the deviation between the timing of reading the intended pixel from the effective light-receiving area Ae and the timing of shifting the effective light-receiving area Ae by one line increase to double, triple, quadruple, and so on with the advance of the shift of the effective light-receiving area Ae, until in the Mth (M: integer) effective light-receiving area, the time lag $\Delta$DM becomes $$\Delta DM=\{1\times(M-1)\}H$$

It follows that the time lag of 1×31H develops in the 32nd effective light-receiving area Ae(32). This time lag, however, is considerably smaller than the corresponding figure for the horizontal read method. Even in the case where the resolution of the temporal barycenter is set to one eighth (i.e. 4×200H) of the time (32×200H) required for reading the effective light-receiving area, therefore, no large error is included in the calculation result and a reliable calculation result is obtained. In this way, the application of the vertical read method improves the accuracy of the calculation of the temporal barycenter as compared with the application of the horizontal read method.

Thus, the application of the vertical read method eliminates the need of correcting the deviation between the timing of reading an intended pixel in the effective light-receiving area and the timing of shifting the effective light-receiving area by one line, thereby producing a highly accurate three-dimensional image.

Also, in the case of the vertical read method, the spatial barycenter can be calculated with higher accuracy than when the horizontal read method is applied. The reason for this is described below.

Figure 26:
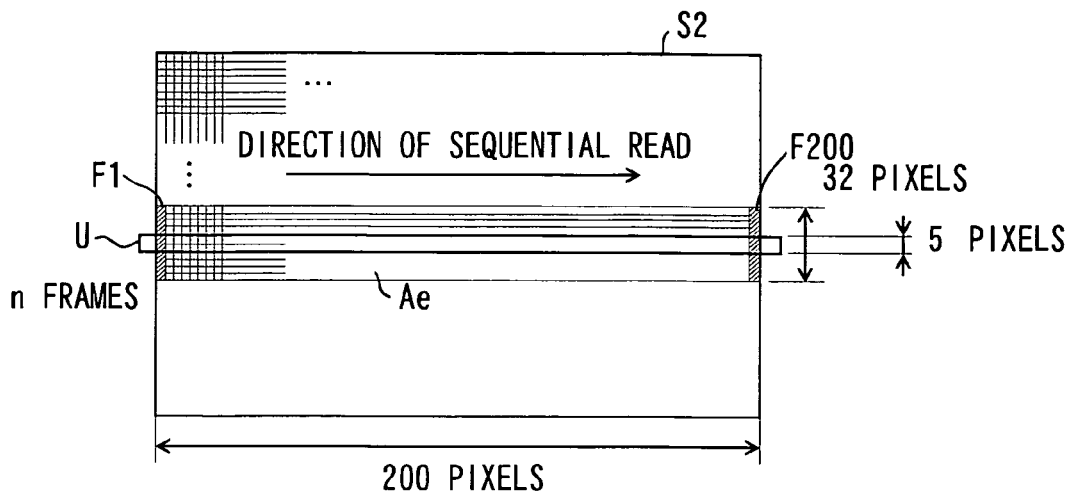
FIG. 26 is a diagram for explaining the read time of each pixel in the effective light-receiving area according to the horizontal read method.
Figure 27:
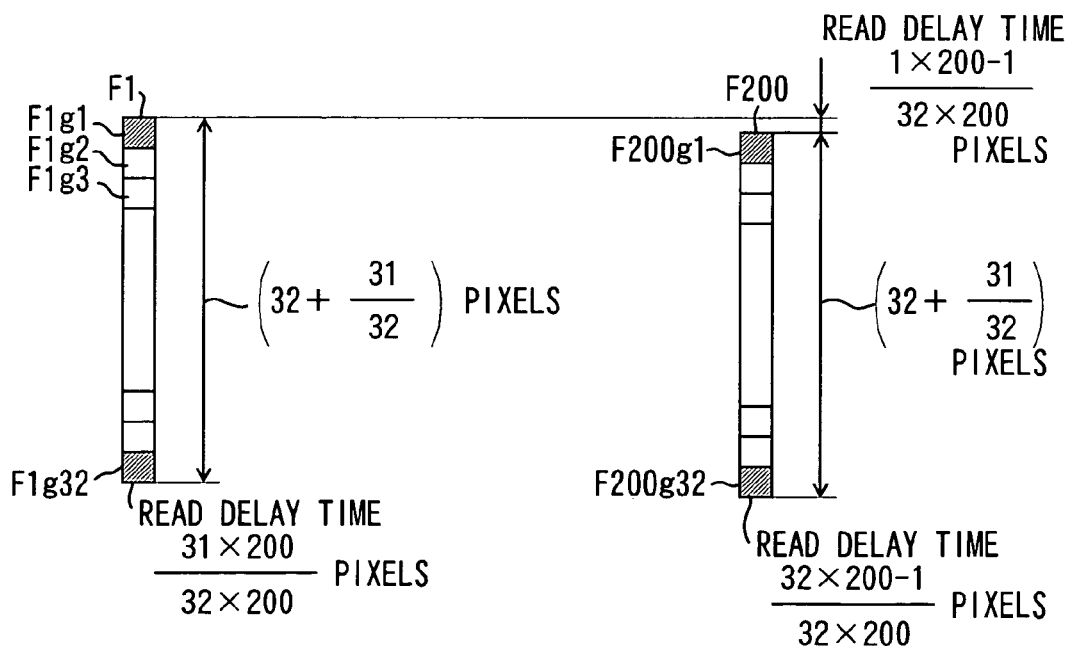
FIG. 27 is a diagram showing the deviation of the timing of reading each pixel in a predetermined column according to the horizontal read method.
Figure 28:
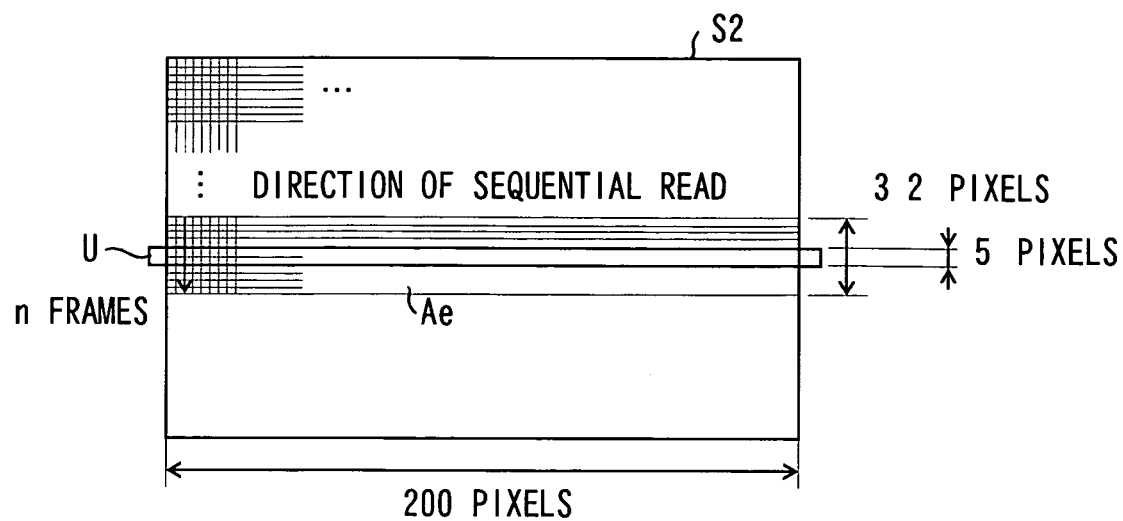
FIG. 28 is a diagram for explaining the timing of reading each pixel in the effective light-receiving area according to the vertical read method.
Figure 29:
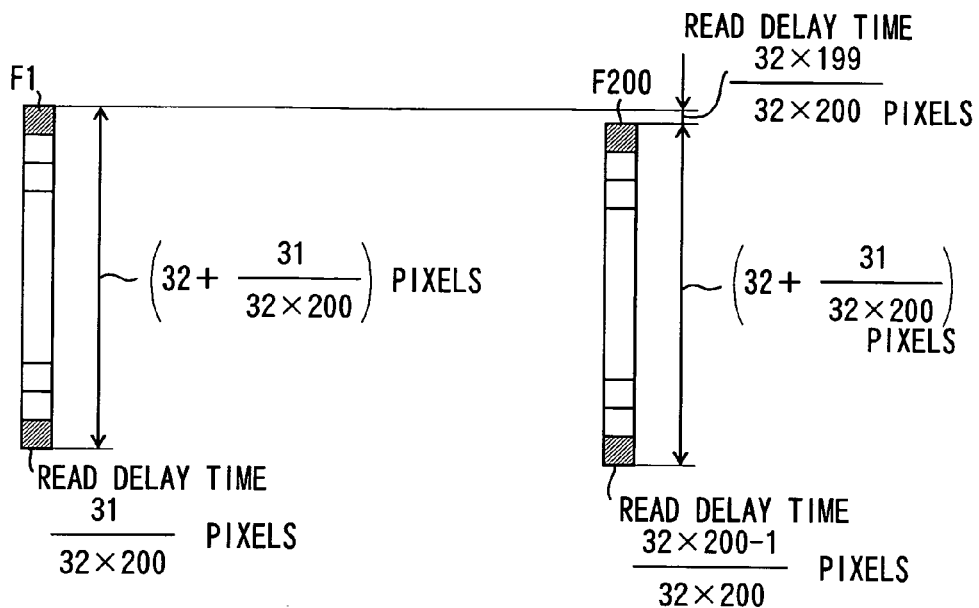
FIG. 29 is a diagram showing the deviation of the timing of reading each pixel in a predetermined column according to the vertical read method.

FIG. 26 is a diagram for explaining the read time of each pixel of the effective light-receiving area Ae in the application of the horizontal read method, FIG. 27 is a diagram showing a read time lag developed when reading the pixels in a predetermined column in the application of the horizontal read method, FIG. 28 is a diagram for explaining the read time of each pixel of the effective light-receiving area Ae in the application of the vertical read method, and FIG. 29 is a diagram showing a read time lag developed when reading the pixels in a predetermined column in the application of the vertical read method. In FIG. 26, the use of the horizontal read method requires the time (200×32)H from the read start until the complete reading of the effective light-receiving area Ae.

As shown in FIG. 27, assume that the pixels in the leftmost column F1 in the diagram are read by the horizontal read method. The time for reading one line, i.e. (1×200) H is required from the timing of reading the pixel F1g1 to the timing of reading the pixel F1g2 in the next line in the column F1. Also, the time of reading 31 lines, i.e. (31×200)H is required from the timing of reading the pixel F1g1 to the timing of reading the pixel F1g32 on the last line.

It follows, therefore, that in the case of reading the pixel F1g2 in the effective light-receiving area Ae, the data obtained is the one received from the slit light beam U after the lapse of the time (1×200)H from the time of reading the pixel F1g1 in the effective light-receiving area Ae. Also, in the case where the pixel F1g3 is read, the data obtained is the one received from the slit light beam U after the lapse of the time (2×200)H from the time when the pixel F1g1 is read. In similar fashion, for the pixel F1gM (M: integer), the data obtained is the one received from the slit light beam U after the lapse of time {(M−1)×200}.

When reading the pixels of the rightmost column F200 in the diagram by the horizontal read method, the time for reading one line, i.e. (1×200)H is required from the timing of reading the pixel F200g1 to the timing of reading the pixel F200g2 on the next line. Also, the time for reading 31 lines, i.e. (31×200)H is required from the timing of reading the pixel F200g1 to the timing of reading the pixel F200g32 on the last row.

In other words, when calculating the barycenter for the pixel data obtained from column F1 in the effective light-receiving area Ae, the data obtained for the pixel F200g2 is the one received from the slit light beam U after the lapse of time (1×200)H from the time of reading the starting pixel F200g. For the pixel F1g3, on the other hand, the data obtained is the one received from the slit light beam U after the lapse of time (2×200)H from the time of reading the starting pixel F1g1. In similar fashion, for the pixel F200gM (M: integer), the data obtained is the one received from the slit light beam U after the lapse of time {(M−1)×200}H.

The time (32×200)H is required for reading all the pixels in the effective light-receiving area Ae. When calculating the spatial barycenter of the pixels F1g1 to F1g32, the pixels F200g1 to F200g32, etc., therefore, the effective light-receiving area Ae is shifted more in Y direction by an width equivalent to (31×200)H/(32×200)H=31/32 pixels.

In calculating the spatial barycenter Mpeak, the output (x) from the image sensor 53 is sampled at predetermined periods. In accordance with the timing of each sampling session, the total sum $\Sigma(x \cdot i)$ of the product $(x \cdot i)$ of the position (i) and the output (x) and the total sum $\Sigma(x)$ of the output (x) for the pixels existing in a predetermined light-receiving width are calculated. From these, the spatial barycenter Mpeak=$\Sigma(x \cdot i)/\Sigma(x)$ is calculated.

In calculating the spatial barycenter, the position associated with the maximum light-receiving amount at a specified timing is detected based on the barycenter ip (spatial barycenter Mpeak) calculated by the barycenter calculation for the pixels (32 pixels over 32 lines according to this embodiment) in the effective light-receiving area Ae. The spatial barycenter is desirably calculated for the data of the pixels juxtaposed in Y direction in each of the columns F1 to F200 along Y direction and obtained at the same time.

As described above, the reading operation performed by the repeated horizontal scan extends the shift width of the effective light-receiving area Ae in Y direction by an amount equivalent to 31/32 pixels. This is indicative of the fact that the spatial barycenter is calculated for the slit light beam U that has slid temporally by an amount equivalent to 31/32 pixels, but not for the slit light beam U that has been obtained at the same timing, and therefore the position associated with the maximum light-receiving amount at a specified timing cannot be determined accurately.

In the vertical read method shown in FIG. 28, in contrast, the width by which the effective light-receiving area Ae shifts in Y direction can be suppressed as compared with when the read operation is performed by the horizontal read method.

In FIG. 28, the time (200×32)H is required from the read start time until complete reading of the effective light-receiving area Ae.

As shown in FIG. 29, assume that the pixels on the leftmost column F1 in the diagram are sequentially read by the vertical read method. For the column F1, the time for reading one pixel, i.e. 1H is required from the timing of reading the pixel F1g1 to the time of reading the pixel F1g2 on the next line. Also, the time for reading 31 pixels, i.e. 31H is required from the timing of reading the pixel F1g1 to the timing of reading the pixel F1g32 on the last line.

For the pixel. F1gM (M: integer), it follows that the data is obtained in the form received from the slit light beam U after the lapse of time {(M−1)×1}H.

This is also true for the case in which the pixels of the rightmost column F200 in the diagram are read by the vertical read method.

The reading of all the pixels of the effective light-receiving area Ae takes the time (31×1)H. When calculating the spatial barycenter for the pixels F1g1 to F1g32 and the pixels F200g1 to F200g32, therefore, the width of the shift of the effective light-receiving area Ae in Y direction extends by an amount equivalent to (31×1)H/(32×200)H={31/(32×200)} pixels.

This value is considerably smaller than the 31/32 pixels which is the amount of the extension for the horizontal read method.

As a result, even in the case where the resolution of the spatial barycenter is one eighth of each pixel in the effective light-receiving area, for example, a reliable calculation result is obtained without any large error being included in the calculation result.

In this way, according to the second embodiment, a highly accurate three-dimensional image can be produced without any need of correcting the deviation between the timing of reading an intended pixel in the effective light-receiving area and the timing of shifting the effective light-receiving area by one line.

Third Embodiment

The basic configuration according to the third embodiment is the same as that of the first and second embodiments. Specifically, FIGS. 1 to 5B, FIGS. 7A to 10 and FIGS. 17 to 19 for the first embodiment and FIG. 20 for the second embodiment and the description thereof are applicable also to the third embodiment. In the description that follows, therefore, the portions not included in the first and second embodiments will be explained.

In the third embodiment, the image sensing information from the image sensor 53 is stored in a memory 63 through a select circuit 75 in synchronism with the clock from a driver 55. The image sensor 53 is controlled by a control signal in such a manner that the light-receiving data are read destructively. As a result, the light-receiving data S (T/n) having the charge accumulation time T/n and the light-receiving data S (T) having the charge accumulation time T, that is, n times larger than T/n are produced. An explanation will be given of a specific case in which n=4.

In FIG. 3, the light-receiving data S (T/4) and the light-receiving data S (T) are output as a digital value from the output processing circuit 62.

The select circuit 75 processes the light-receiving data S (T/4) and the light-receiving data S (T) in the following manner. Specifically, the light-receiving data S (T), if is not saturated, is output as it is, while in the case where the light-receiving data S (T) is saturated, on the other hand, data four times as large as the light-receiving data S (T/4) are output. The configuration and operation of the select circuit 75 will be described in detail later.

In FIG. 5A, the slit light beam U reflected by the object Q enters the image sensing surface S2 of the image sensor 53. The slit light beam U moves by one pixel pitch pv on the image sensing surface S2 at each sampling period.

The image sensor 53 outputs the light-receiving data S (T/4) and the light-receiving data S (T) at each sampling period. These outputs include the first frame F (T/4) including the light-receiving data S (T/4) corresponding to one frame and the second frame F (T) including the light-receiving data S (T) corresponding to one frame are output for each effective light-receiving area Ae. In other words, the light-receiving data representing a total of two frames are output. In the process, the deflection is effected actually at a conformal speed.

Figure 31:
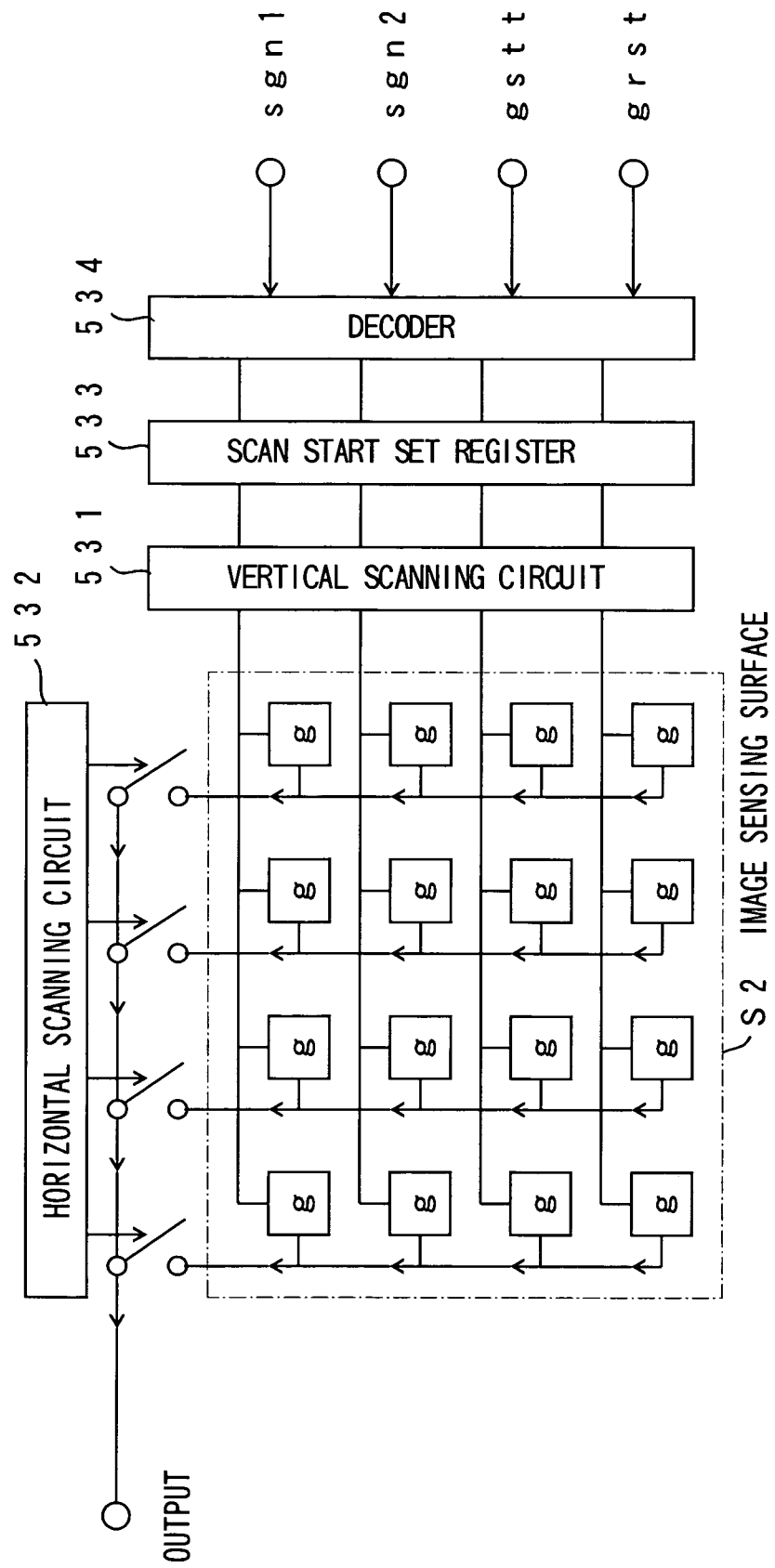
FIG. 31 is a diagram showing a model configuration of the image sensor.

FIG. 31 is a model diagram showing another configuration of the image sensor.

An image sensor 53C is basically the same as the image sensor 53 shown in FIG. 12. Thus, in the description that follows, the image sensor 53C will be referred to as the image sensor 53.

The data signals sgn1, sgn2 input to the scan start set register 533 cause a stripe image in the effective light-receiving area Ae to be designated and read out. Also, by inputting the read start signal gstt and the reset signal grst separately from each other, the non-destructive read operation is performed. Specifically, the non-destructive read operation is carried out when only the read start signal gstt is input, after which the charge accumulation is continued until the reset signal grst is input.

The "non-destructive read operation" is a method of reading the light-receiving data from the image sensing device in such a manner that the particular light-receiving data (charge) remain as they are in the image sensing device as far as no reset signal is applied thereto.

Now, the configuration and operation of the select circuit 75 will be explained in detail.

Figure 32:
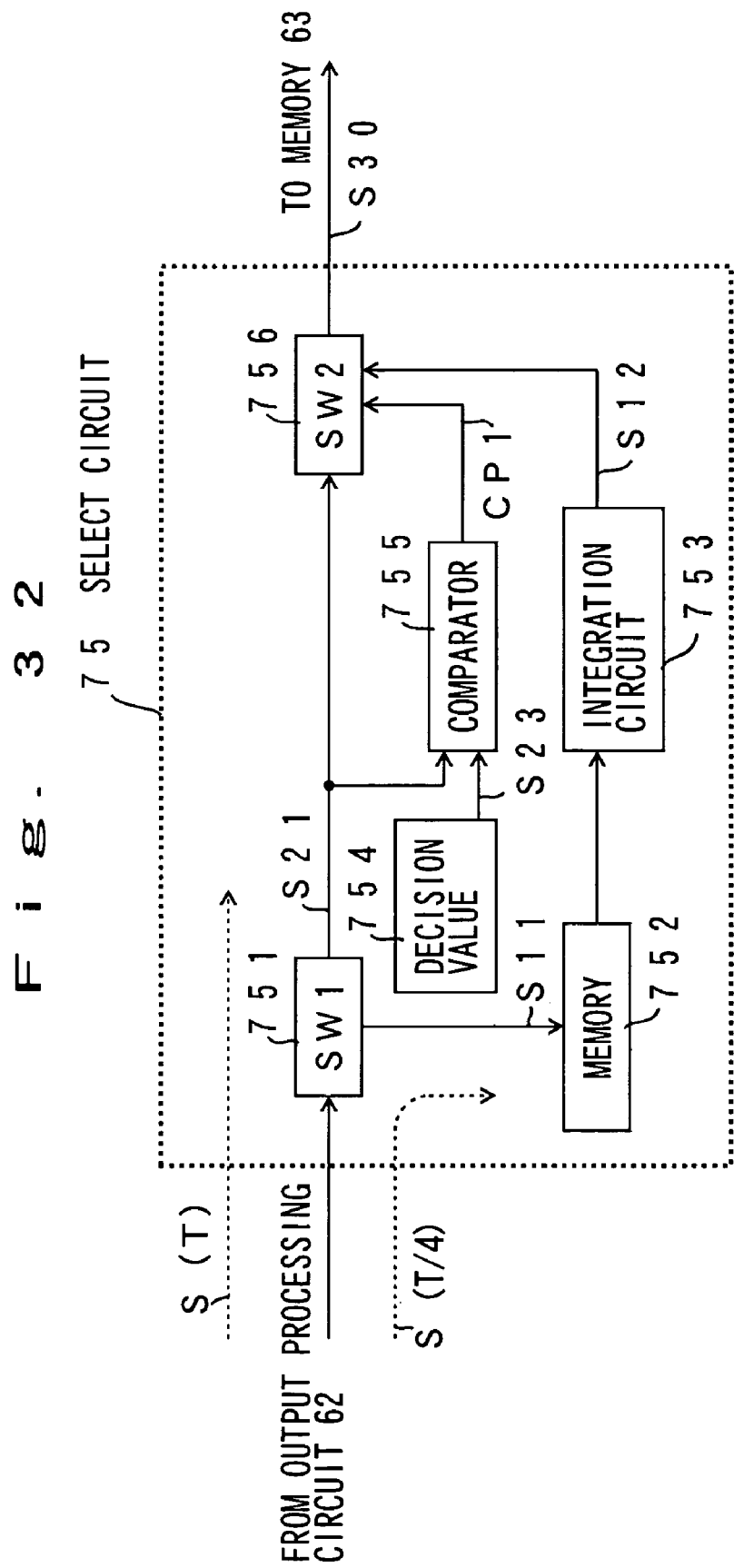
FIG. 32 is a block diagram showing a configuration of a selecting circuit.

FIG. 32 is a block diagram showing a configuration of the select circuit 75.

As shown in FIG. 32, the select circuit 75 includes switch circuits 751, 756, a memory 752, an integration circuit 753, a decision value circuit 754 and a comparator circuit 755.

The switch circuit 751 sends the light-receiving data S (T/4) of the first frame F (T/4) transferred thereto from the output processing circuit 62 to the memory 752 as the light-receiving data S11, and the light-receiving data S (T) of the second frame F (T) to the switch circuit 756 and the comparator circuit 755 as the light-receiving data S21.

The memory 752 is a read-write memory having a storage capacity of 200×32 bytes for storing all the light-receiving data S11.

The integration circuit 753 calculates and sends the light-receiving data S12 four times as large as the light-receiving data S11 to the switch circuit 756.

The decision value circuit 754 sets a decision value S23 providing a reference for saturation decision of the light-receiving data S21 in the comparator circuit 755. A specific example of the decision value S23 is "255".

The comparator circuit 755 compares the light-receiving data S21 with the decision value S23, and generates a control signal CP1 based on the comparison result and sends it to the switch circuit 756. The control signal CP1 controls the switch circuit 756 in the following manner.

Figure 34A:
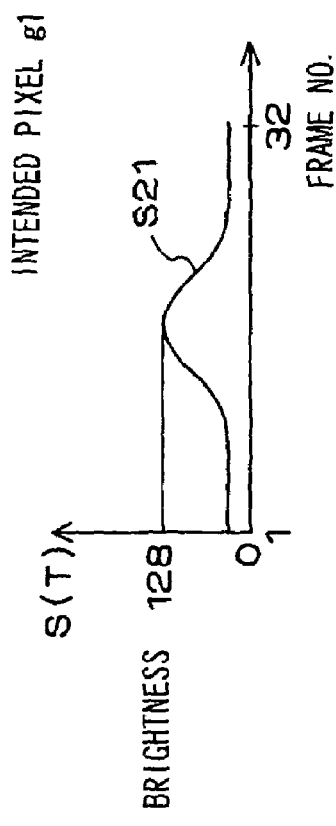
FIGS. 34A to 34D are diagrams showing an example distribution of the light-receiving data in the case where the charge accumulation time is T/4 and T.
Figure 34B:
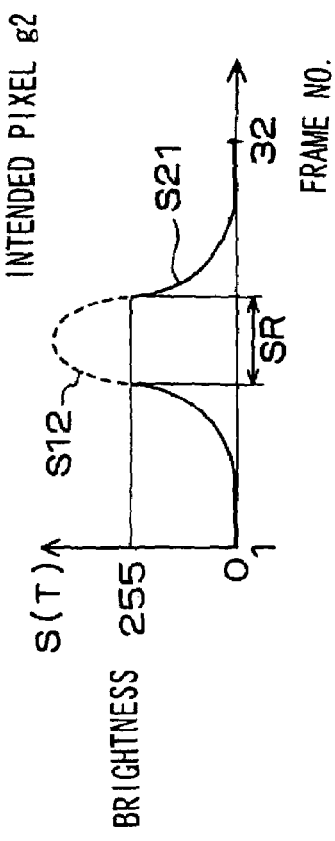
Figure 34C:
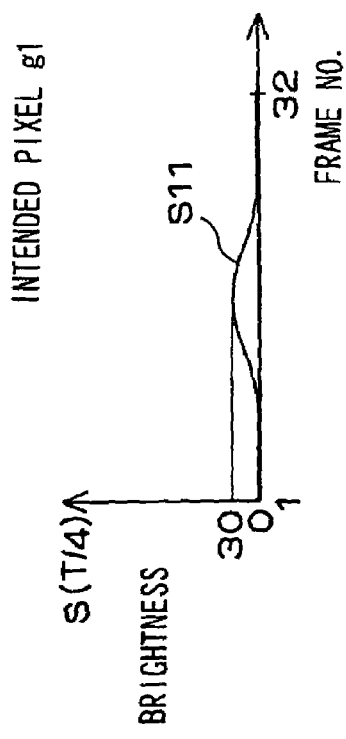
Figure 34D:
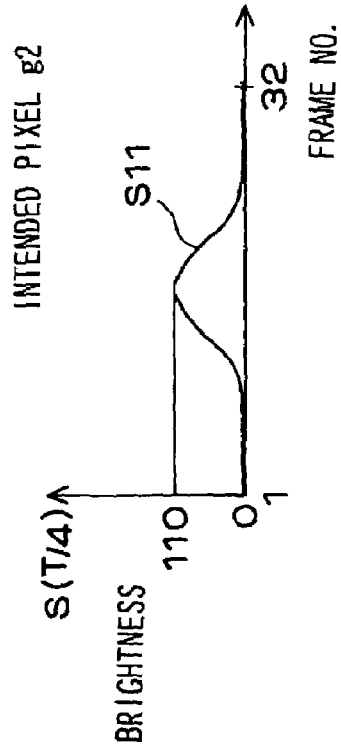

Specifically, in the case where the light-receiving data S21 are not saturated, the particular light-receiving data S21 are transferred as they are to memory 63 through the switch circuit 756 (See the portion defined by solid line in FIG. 34D). In the case where the light-receiving data S21 are saturated, on the other hand, the light-receiving data S12, i.e. a value for times as high as the light-receiving data S (T/4) of the first frame F (T/4) are transferred to the memory 63 through the switch circuit 756 (See the portion defined by dashed line in FIG. 34D).

In this way, it is determined whether the light-receiving data S (T) are saturated or not for all the pixels of the second frame F (T) according to whether the decision value "255" has been reached or not. In the case where the light-receiving data S (T) is not saturated, the particular light-receiving data S (T) is used, while in the case where the light-receiving data S (T) is saturated, on the other hand, a signal four times as large as the light-receiving data S (T/4) is sent to the memory 63 as 8-bit or 10-bit light-receiving data S30.

In short, the light-receiving data obtained from the image sensor 53 can be read out as a large value without being affected by noises.

As a result, in the case where the barycenter is calculated for the light-receiving data S30, a highly accurate three-dimensional image can be determined.

In the embodiments described above, the accumulation time is set in two stages of T and T/4. Instead, more stages of accumulation time can be set. For example, three or more stages including T, T/2, T/4, T/8 or T, T/3, T/9 can be set. Among the signals obtained from the accumulation time thus set, a signal having the longest accumulation time, i.e. a signal having a high output level is selected.

Now, with reference to FIGS. 33 and 36, an explanation will be given of the process in which the light-receiving data 30 are output from the select circuit 75 and the temporal barycenter and the spatial barycenter are calculated for the light-receiving data S30 by use of specific numerical values applied to the light-receiving data S (T) and S (T/4).

First, the process of calculating the temporal barycenter will be explained.

Figure 33:
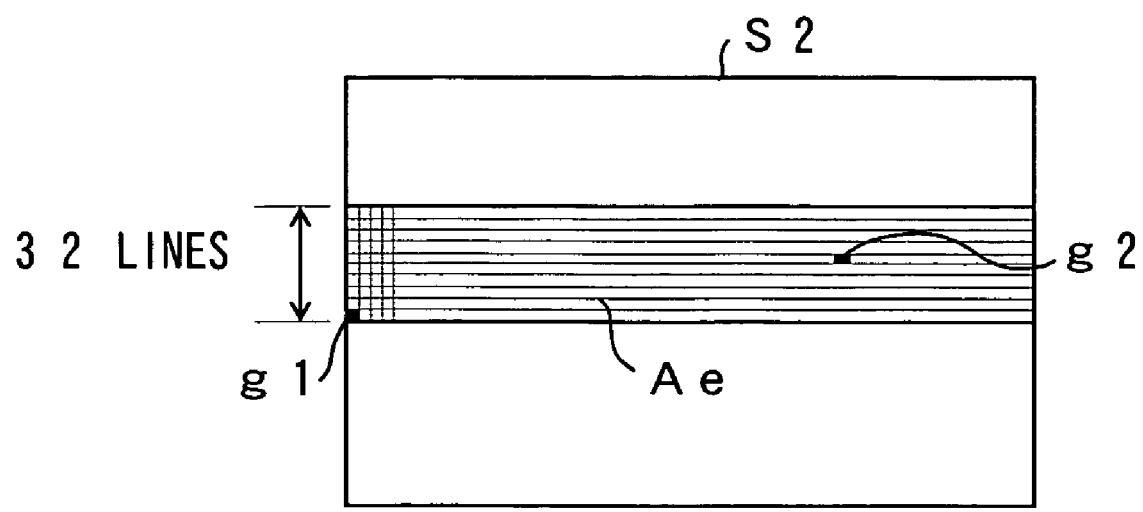
FIG. 33 is a diagram showing an intended pixel in the effective light-receiving area.

FIG. 33 is a diagram showing mutually different intended pixels g1, g2 in the effective light-receiving area Ae, and FIGS. 34A to 34D are diagrams showing an example of light-receiving data distribution in each frame in the case where the charge accumulation time for the intended pixels g1, g2 are T/4 and T, respectively.

FIG. 34A is a diagram showing an example of light-receiving data distribution in each frame in the case where the charge accumulation time for the intended pixel g1 is T/4, FIG. 34B is a diagram showing an example of light-receiving data distribution in each frame in the case where the charge accumulation time for the intended pixel g1 is T, FIG. 34C is a diagram showing an example of light-receiving data distribution in each frame in the case where the charge accumulation time for the intended pixel g2 is T/4, and FIG. 34D is a diagram showing an example of light-receiving data distribution in each frame in the case where the charge accumulation time for the intended pixel g2 is T.

As shown in FIG. 34A, in the case where the peak value of the light-receiving data read after the accumulation time of T/4 for the intended pixel g2 is 30, i.e. in the case where the peak value is considerably smaller than the saturation value "255" of the light-receiving data, the temporal barycenter is calculated for the intended pixel g1.

Then, the calculation result is low in accuracy. This is because the S/N ratio of the intended pixel g1 is low.

By the way, in calculating the temporal barycenter Npeak, the output (x) from the image sensor 53 within a predetermined period of time is sampled at predetermined cycles for each pixel. The total sum Σ(x·i) of the product (x·i) of the output (x) constituting the sampling value and the sampling timing (i) and the total sum Σ(x) of the output (x) are calculated. These values are used for calculating the temporal barycenter Npeak=Σ(x·i)/Σ(x).

As shown in FIG. 34B, on the other hand, the peak value of the light-receiving data read after the accumulation time T four times as long as the accumulation time T/4 for the preceding read session for the intended pixel g1 is 128.

By the way, "128" is about four times as large as 30.

In this way, the light-receiving data S21 read after the accumulation time T has a larger S/N ratio than the light-receiving data S11 read after the accumulation time T/4.

Also, as shown in FIG. 34C, in the case where the peak value of the light-receiving data read after the accumulation time T/4 for the intended pixel g2 is 110, on the other hand, it is impossible to use the same method as the one used for the intended pixel g1, i.e. the method of calculating the temporal barycenter using the light-receiving data S21 read after the accumulation time T which is four times as large as the charge accumulation time T/4 of the preceding read session for the intended pixel g2. The direct use of such a method would cause the saturation of the light-receiving data S21 for a plurality of frames in the section SR as shown by solid line in FIG. 34D.

In such a case, the value S12 equal to the light-receiving data S11 multiplied by 4 is used as the value of the light-receiving data S21 in the section SR. By doing so, the light-receiving data high in S/N ratio can be obtained also for the intended pixel g2.

By performing the process described above for an arbitrary intended pixel in the effective frame Ae, the calculation result of the temporal barycenter is affected by less noises, thereby producing a three-dimensional image high in accuracy.

Now, an explanation will be given of the process of calculating the spatial barycenter.

Figure 35:
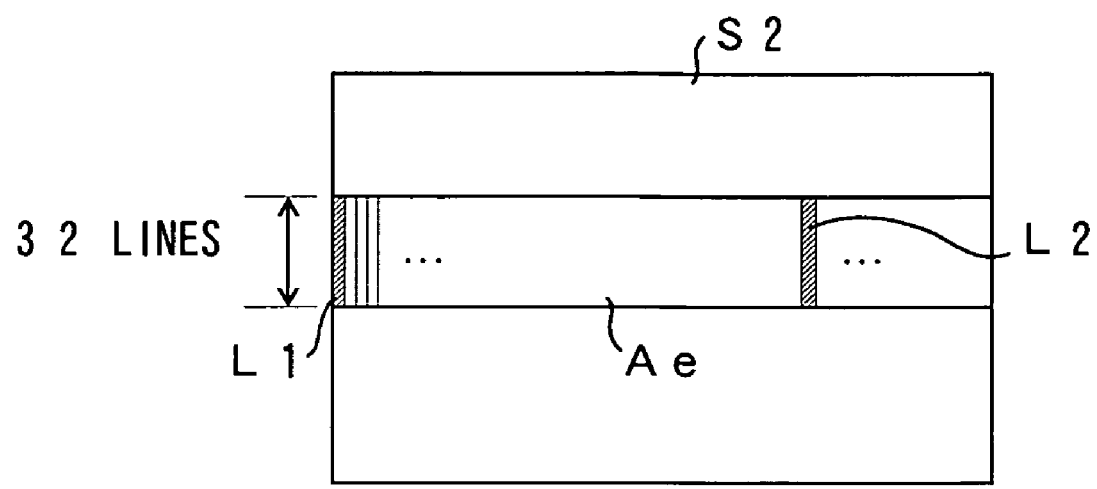
FIG. 35 is a diagram showing an intended pixel column in the effective light-receiving area.

FIG. 35 is a diagram showing different intended pixel strings L1, L2 in the effective light-receiving area Ae, and FIGS. 36A to 36D are diagrams showing an example distribution of the light-receiving data in each frame in the case where the charge accumulation time for the intended pixel strings L1 and L2 are T/4 and T, respectively.

Figure 36A:
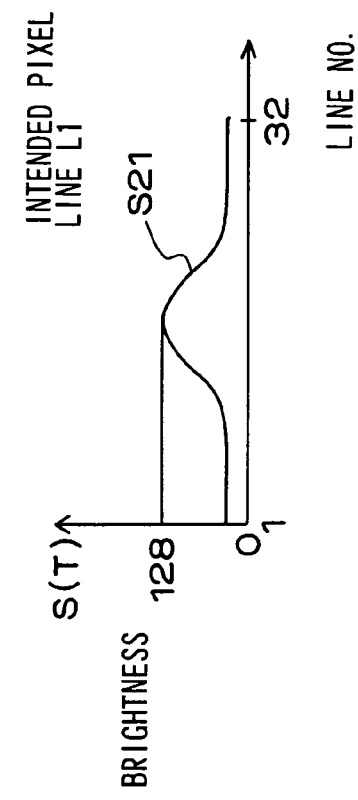
FIGS. 36A to 36D are diagrams showing an example distribution of the light-receiving data in the case where the charge accumulation time is T/4 and T.
Figure 36B:
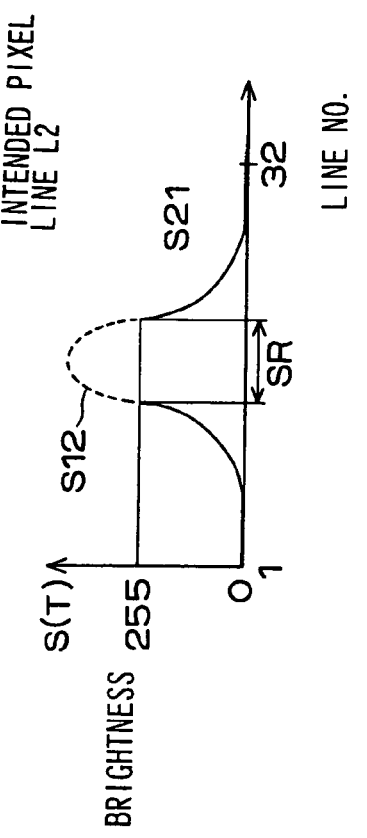
Figure 36C:
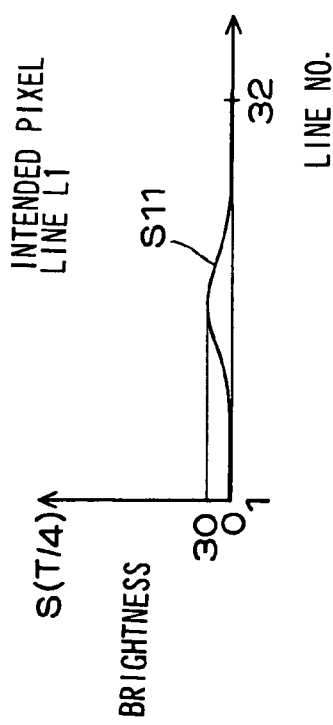
Figure 36D:
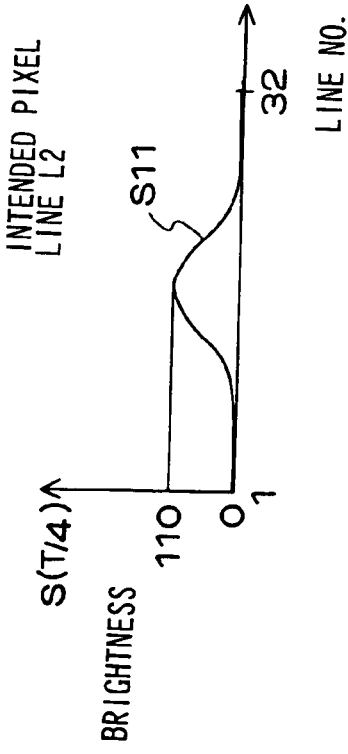

FIG. 36A is a diagram showing an example distribution of the light-receiving data in each frame in the case where the charge accumulation time for the intended pixel string L1 is T/4, FIG. 36B is a diagram showing an example distribution of the light-receiving data in each frame in the case where the charge accumulation time for the intended pixel string L1 is T, FIG. 36C is a diagram showing an example distribution of the light-receiving data in each frame in the case where the charge accumulation time for the intended pixel string L2 is T/4, and FIG. 36D is a diagram showing an example distribution of the light-receiving data in each frame in the case where the charge accumulation time for the intended pixel string L2 is T.

As shown in FIG. 36A, in the case where the peak value of the light-receiving data is 30 in each frame for the charge accumulation time T/4 of the intended pixel string L1, i.e. in the case where the peak value is considerably smaller than the saturation value "255" of the light-receiving data, calculation of the spatial barycenter for the intended pixel string L1 would lead to the calculation result of a low accuracy. This is because the S/N ratio of the intended pixel string L1 is low.

By the way, in calculating the spatial barycenter Mpeak, the output (x) from the image sensor 53 is sampled at a predetermined period. The total sum Σ(x·i) of the product (x·i) of the position (i) the output (x) of the pixels within a predetermined light-receiving width and the total sum Σ(x) of the output (x) are calculated in a manner corresponding to the timing of each sampling session. These values are used for calculating the spatial barycenter Mpeak=Σ(x·i)/Σ(x).

In such a case, the intended pixels g1, g2 described for the calculation of the temporal barycenter are regarded as the intended pixel strings L1, L2, respectively, so that the result of calculation of the spatial barycenter is affected by less noises, thereby producing a very accurate three-dimensional image.

As described above, according to the third embodiment, the output not saturated can be obtained from the image sensing device. In addition, an output of a superior S/N ratio can be produced from the image sensing device. Thus, the S/N ratio of the light-receiving data output from an image sensor capable of non-destructive read operation such as a MOS type image sensor is improved for producing a highly accurate three-dimensional image.

In the third embodiment, the light-receiving data S (T/4) is produced as a first frame F (T/4) equivalent to one frame by the image sensor 53 separately from the light-receiving data S (T) as a second frame F (T) equivalent to one frame. In view of this, a buffer memory for sequentially storing the light-receiving data corresponding to each frame for each pixel may be provided as a separate entity from the image sensor 53, so that the light-receiving data for the respective frames are output at the same time from a buffer memory.

The third embodiment uses the light-receiving data S (T/4) having a charge accumulation time of T/4 and the light-receiving data S (T) having a charge accumulation time T four times as long as T/4. In place of the light-receiving data S (T), however, the light-receiving data having a charge accumulation time double, triple, six times or eight times as long as the charge accumulation time T/4 of the light-receiving data S (T/4) may be used. In such a case, a data conversion table can be used for calculating the light-receiving data S12 of a value corresponding to the magnification with respect to the light-receiving data S11.

Fourth Embodiment

A basic configuration of the fourth embodiment is identical to but partially different from that of the first embodiment. Specifically, FIGS. 2, 4 and 11 and the description with reference thereto applicable to the first embodiment are also applicable to the fourth embodiment. Also, some parts of the other diagrams applicable to the first embodiment are also applicable to the fourth embodiment. Further, the diagrams used for explaining the fourth embodiment are identical in many parts to the diagrams used for explaining the first embodiment. In the description that follows, the portions not included in the other embodiments will be explained.

In the fourth embodiment, the read range on the light-receiving surface of an image sensing device is variable. The size and position of the range may be set arbitrarily or may be selected from a plurality of predetermined choices. The advisability of change is either determined automatically or designated by the user or an external device. In the case of automatic determination, the light-receiving area of the light-receiving surface entered by the detection light reflected from the object is estimated, and in the case where the light-receiving area is smaller than a setting, the read range is reduced. In the case where the light-receiving area is not smaller than the setting, on the other hand, the read range is maximized. The light-receiving area as referred herein is defined as a mass of pixels entered (strictly, expected to be entered) by the detection light at any time point during the period from the start and end of scanning an object. In the case where the slit light is used as the detection light, for example, the light-receiving area at a given time point during the scan is linear, and with the progress of the scan, moves into a planar area so that it finally becomes planar over the entire scanning period.

This light-receiving area can be estimated with a sufficiently high practical accuracy by image sensing the object with the same angle of view as the received detection light, for example, and extracting an object image by image processing of the picked-up image.

FIG. 37 is a diagram showing a configuration of a measuring system 1D according to the fourth embodiment.

The basic configuration of the measuring system 1D is the same as that of the measuring system 1 according to the first embodiment. A two-dimensional color image is used as reference information for correcting a three-dimensional model in the host 3, ID information for facilitating the understanding by the user that the three-dimensional model is that of an object Q, and framing information for automatically setting the read range unique to the invention. To facilitate the extraction of an object image from the color image, a blue back screen 5 is arranged on the back of the object Q for three-dimensional measurement.

Figure 38:
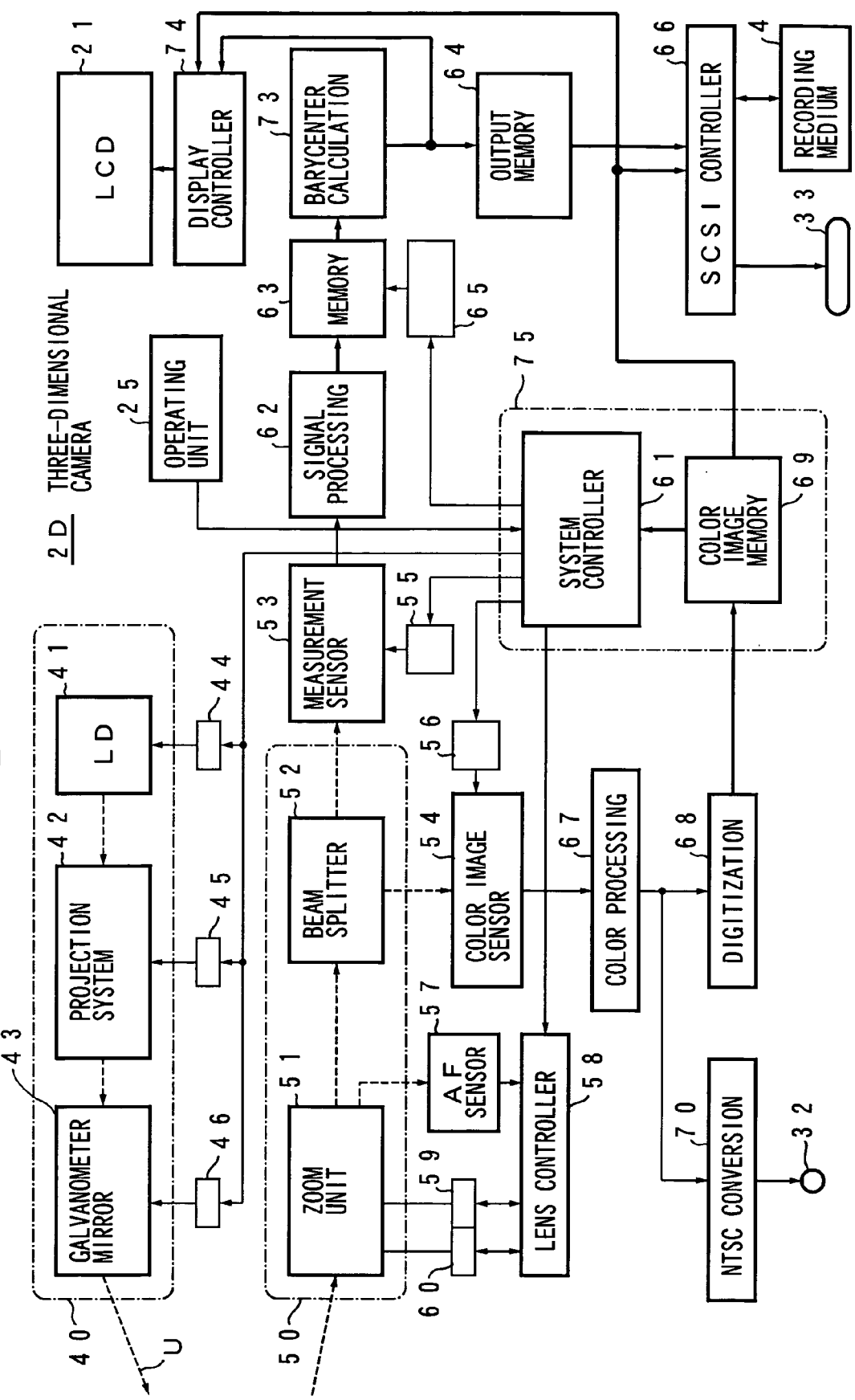
FIG. 38 is a block diagram showing another example of the functional configuration of a three-dimensional camera.

FIG. 38 is a block diagram showing an example functional configuration of the three-dimensional camera Two-dimensional.

In the three-dimensional camera Two-dimensional shown in FIG. 38, a system controller 61 reads the color image from the color memory 69, and analyzes it in the manner described later. The system controller 61 and the color image memory 69 make up means for estimating a light-receiving area. The three-dimensional camera Two-dimensional is basically the same as the three-dimensional camera 2 shown in FIG. 3. In the description that follows, therefore, the three-dimensional camera Two-dimensional will be referred to as the three-dimensional camera 2.

Figure 39A:
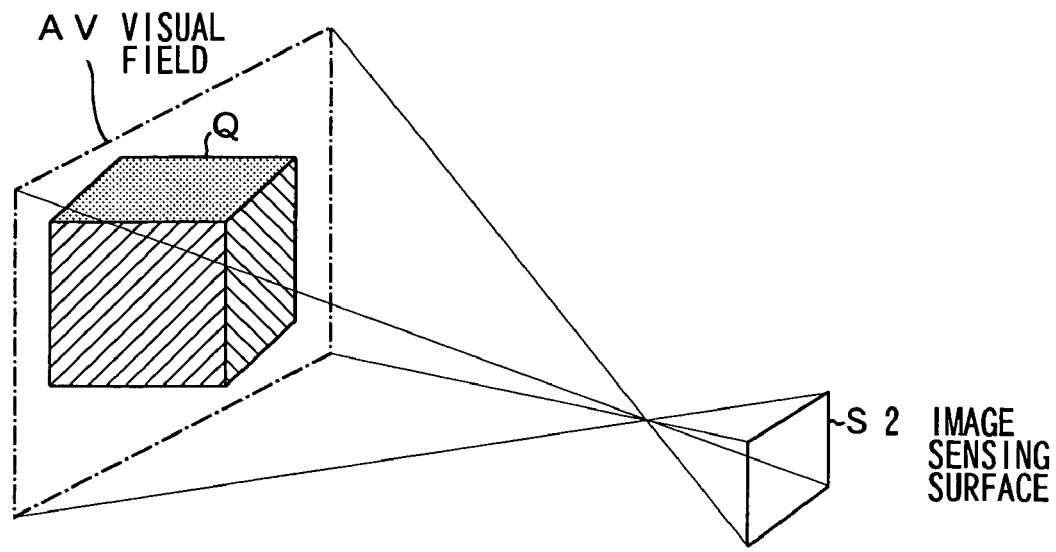
FIGS. 39A and 39B are diagrams showing the relationship between the visual field of measurement and an object.
Figure 39B:
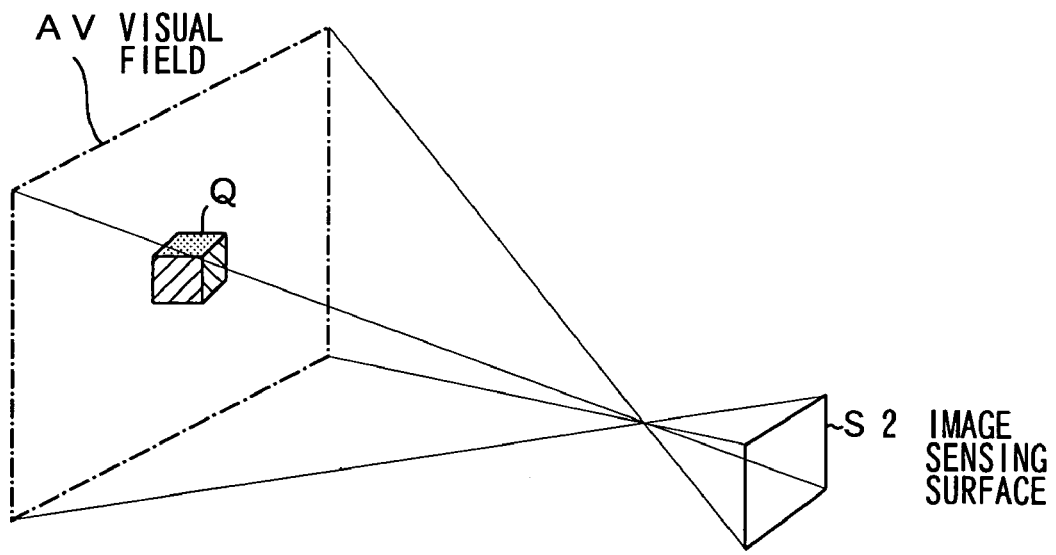

FIGS. 39A and 39B are diagrams showing the relationship between the visual field for measurement and the object.

Even in the case where the three-dimensional camera and the object Q are arranged as near to each other as possible within a measurable range and the zooming is carried out, it may occur that the object Q is extremely small as compared with the visual field AV. In order to shorten the measurement time and reduce the output data amount in such a case, the three-dimensional camera 2 has a "high-speed mode". The high-speed mode is an operation mode in which the read range of the light-receiving surface S2 of the image sensor 53 is, set according to the size of the object Q relative to the visual field AV. The user can select either "high-speed mode" or "normal mode" for maximizing the read range regardless of the size of the object Q. In high-speed mode, the three-dimensional camera 2 optimizes the read range of the three-dimensional camera automatically.

In the case where the object Q is sufficiently large as compared with the visual field AV as shown in FIG. 39A, the unrequired data represents only a small proportion of the output data even when normal mode is selected. In the case where the object Q is small as compared with the visual field AV as shown in FIG. 39B, on the other hand, the proportion of the unrequired data can be reduced by selecting the high-speed mode.

FIG. 40 is a diagram showing the read range of the image sensor.

Regardless of normal mode or high-speed mode, one frame of the image sensor 53 is read only from the effective light-receiving areas Aen, Aeh of the frame in order to assure high speed. The effective light-receiving areas Aen, Aeh are the ones where the line indicating the profile of the object in the measurable distance range is focused and shifts by one pixel each time for each frame with the deflection of the slit light beam U as described with reference to the first embodiment. According to the fourth embodiment, the number of pixels along the direction of shifting of the effective light-receiving areas Aen, Aeh is fixed to 32. The number of pixels along the length of the effective light-receiving area Aen (horizontal direction) in normal mode is 200. The number of pixels along the length of the effective light-receiving area Aeh in high-speed mode, on the other hand, is set to a value H within the range of 50 to 150, for example (H=100 in the shown case).

The read range ARn in normal mode is the sampling range ASn of 200×200 in pixel size included in the light-receiving surface S2, plus the stripe area having a width equivalent to 31 pixels on the upper and lower sides of the sampling range ASn. The sampling range ASn is a mass of pixels intended for calculation of the temporal barycenter Npeak (barycenter ip) described above. In other words, the number of sampling points in normal mode is 200×200.

The read range ARh in high-speed mode, on the other hand, is the range representing the part of the light-receiving surface S2 equivalent to the sampling range ASh having a size of H×H pixels, plus the stripe area having a width equivalent to 31 pixels each at the upper and lower ends of the sampling range ASh.

By setting the read ranges ARn, ARh wider than the sampling ranges ASn, ASh, respectively, in this way, the temporal barycenter Npeak can be calculated using the light-receiving information representing 32 frames per pixel. By the way, in FIG. 40, the read range ARn in normal mode is somewhat smaller than the light-receiving surface S2. The invention is not limited to such a case, however, but the whole light-receiving surface S2 may be set as the read range ARn. Further, the read ranges ARn, ARh may be set equal to the sampling ranges ASn, Ash, respectively, in the same mode.

In FIGS. 7A and 7B, the first frame 1 of the light-receiving surface S2 contains the light-receiving data of 32 lines from line 1 providing the leading line of the read range to line 32. Also according to this embodiment, the number of pixels per line in normal mode is 200, while the number of pixels per line in high-speed mode is smaller than 200.

The light-receiving data from frames 1 to 32 are sequentially transferred to and stored in the memory 63 through the signal processing circuit 62. In other words, the memory 63 has stored therein the light-receiving data of frames 1, 2, 3, and so on, in that order. The data of line 32 providing the leading line in the sampling range is stored on the 32nd line for frame 1, on the 31st line for frame 2, and so on. In this way, the data are stored by being shifted one line upward for each frame.

Now, a method of selectively reading in the image sensor 53 will be explained.

FIG. 41 is a model diagram showing another configuration of the image sensor.

The image sensor 5 three-dimensional is basically the same as the image sensor 53 shown in FIG. 12. Therefore, in the description that follows, the image sensor 5 three-dimensional will be referred to as the image sensor 53.

The image sensor 53 includes a scan start set register 533 for applying an initial value of the register indicating the scan start line to a vertical scanning circuit 531, whereby the read operation of the effective light-receiving areas Aen, Aeh described above is realized. Also, a scan start set register 535 is provided for applying an initial value of the register indicating the scan start column to a horizontal scanning circuit 532, whereby the read operation in high-speed mode is realized.

FIG. 42 is a diagram showing the read data amount in normal mode and high-speed mode.

In normal mode, data corresponding to 262 frames of 200 pixels per line are read from the image sensor 53 and written in the memory 63 in the same order. Concurrently with the write operation into the memory 63, however, the data can be read out for calculation of the barycenter. By writing new data into an address from which data have been read, therefore, the required memory capacity can be reduced. In high-speed mode, on the other hand, data corresponding to 162 (=H+52) frames of 100 pixels per line are read and written in the memory 63 in the same order. The smaller the read range of the light-receiving surface S2, the smaller the data amount and the shorter the time required for reading from the image sensor 53.

Figure 43A:
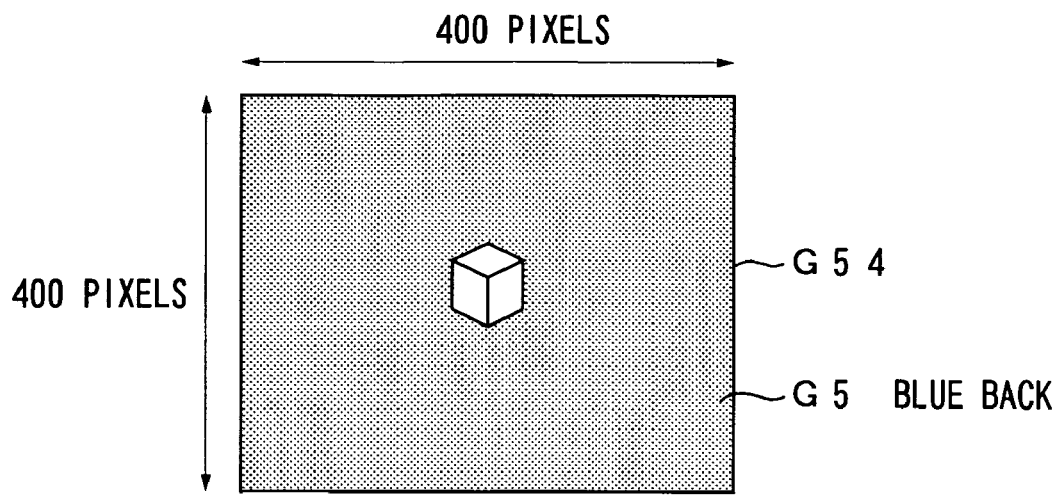
FIGS. 43A to 43C are diagrams showing procedures of setting the read range.
Figure 43B:
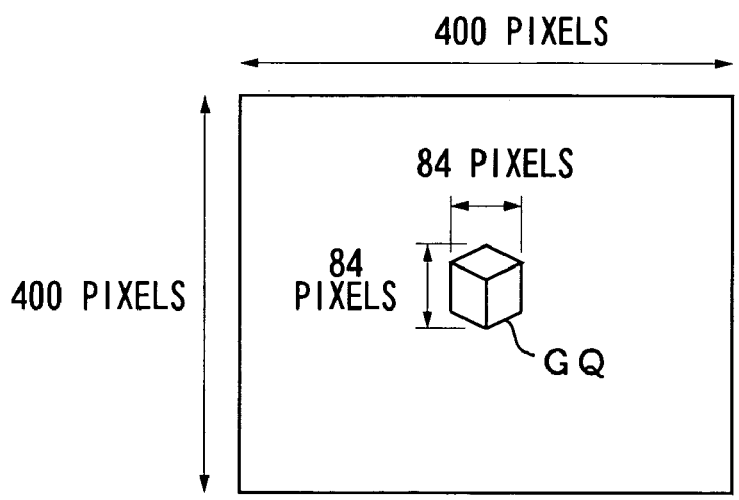
Figure 43C:
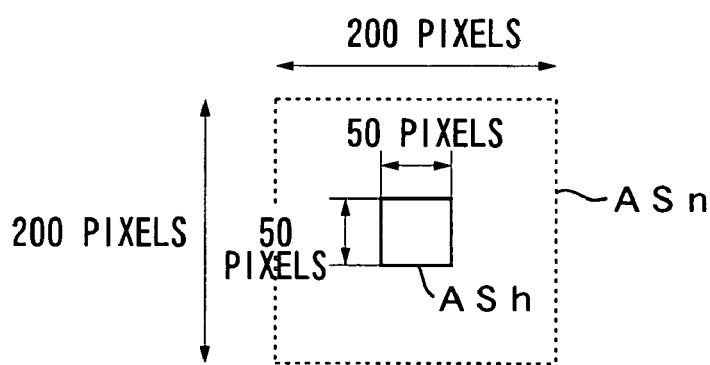

FIGS. 43A to 43C are diagrams showing the steps of setting the read range.

As shown in FIG. 43A, a color image G54 obtained by a color image sensor 54 is configured with an object image and an image (blue back) G5 of the back screen 5.

First, the object image is extracted from the color image G54 by the color discrimination process. Then, as shown in FIG. 43B, the sizes (number of pixels) in horizontal and vertical directions of the object image GQ extracted are checked. As shown in FIG. 43C, an area larger by a predetermined margin than the minimum rectangular area containing the object image GQ is calculated and a sampling range ASh is set on the light-receiving surface S2. In the process, the difference in resolution, if any, between the color image G54 and the light-receiving surface S2 is taken into account. In the example of FIGS. 43A to 43C, for example, the size of the object image GQ is 84×84 pixels for the resolution of 400× 400. Therefore, a larger rectangular area of 100×100 pixels is determined and incorporated in the light-receiving surface S2, thus setting a sampling range ASh having 50×50 pixels.

FIG. 44 is a diagram showing the manner in which a sampling range is set according to a modification.

The smaller the size of the sampling ranges ASh1 to ASh7, the smaller the output data amount. The size can be changed either in several steps, for example, in units of 50 pixels in each direction or steplessly by one pixel each. The read ranges ASh1 to ASh7 may be located at a fixed position with the center thereof coinciding with the center of the light-receiving surface S2 as shown in FIGS. 44b and 44c, or at an arbitrary position in proximity to the edge of the light-receiving surface S2 as shown in FIGS. 44e and 44f. The latter can reduce the unrequired data more. As to the size, on the other hand, the number of pixels is not necessarily the same in horizontal direction and vertical direction, but can be set differently in each direction as shown in FIGS. 44g and 44h.

Any way, the three-dimensional camera 2 sends to the host 3, as a measurement, the positional information of the sampling ranges ASh1 to ASh7 together with the temporal barycenter ip for the number of pixels in the sampling ranges ASh1 to ASh7. The host 3 calculates the three-dimensional position based on the measurement result and the apparatus information for specifying the direction of light-receiving of each pixel on the light-receiving surface S2.

Figure 45:
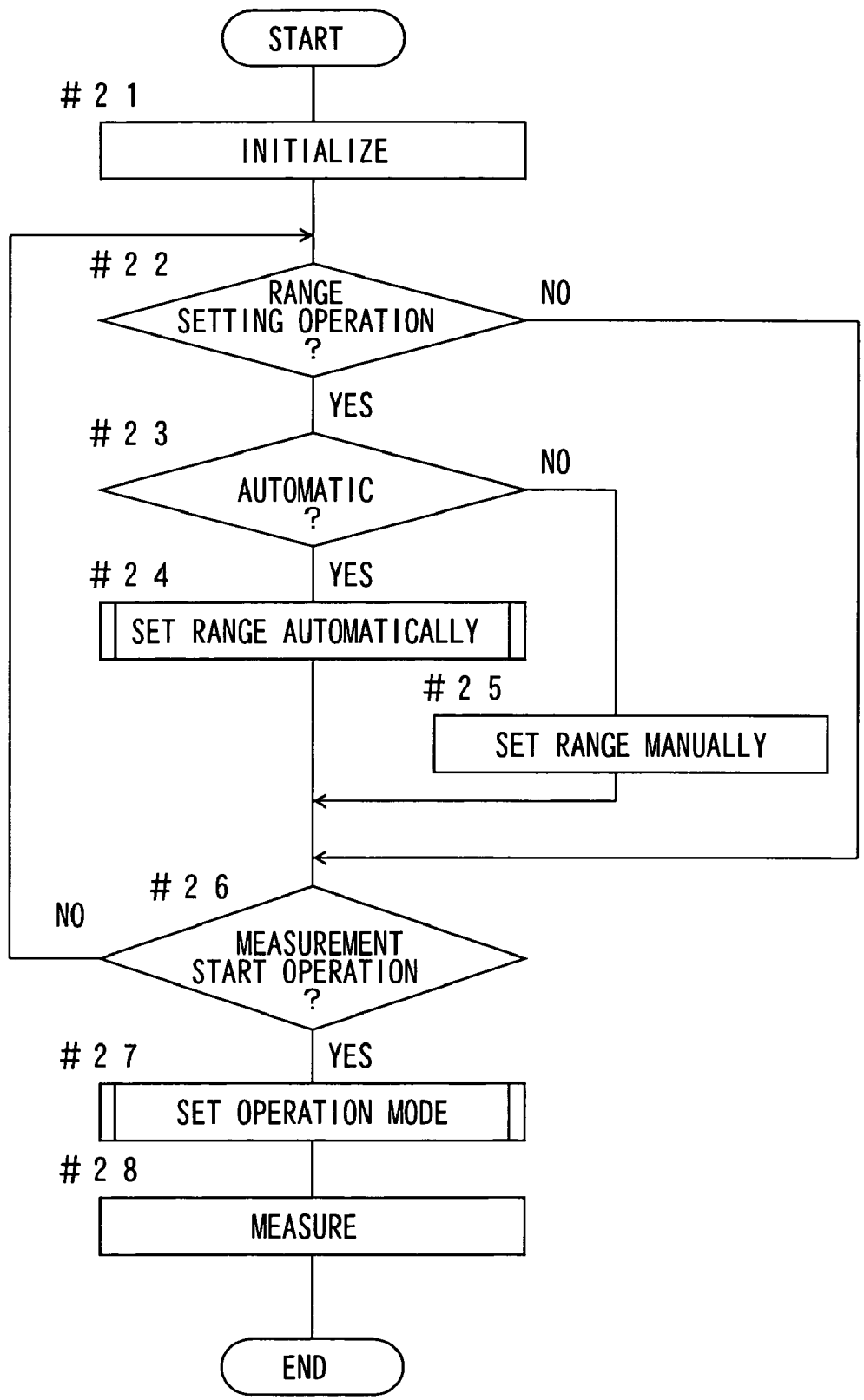
FIG. 45 is a flowchart schematically showing the operation of the three-dimensional camera.

FIG. 45 is a flowchart showing the concept of operation of the three-dimensional camera 2.

At the end of initialization with power switched on, the three-dimensional camera 2 stands by waiting for the operation by the user (#21). Upon operation for setting the read range, the automatic range setting process or the manual range setting process is performed in accordance with AUTO/MANU selection (#22 to #25). When the measurement start is designated by the turning on of a shutter button 27, the operation mode is set and then measurement is conducted (#26 to #28).

FIG. 46 is a flowchart of the automatic range setting subroutine.

As explained with reference to FIGS. 43A to 43C, the object to be measured is extracted from the color image G54 (#241). Based on the extraction result, the size of the object to be measured with respect to the visual field is calculated (#242). In accordance with the size of the effective light-receiving area estimated by analysis of the color image G54, the sampling range ASh is determined and the read range ARh is set (#243).

Also, the operation mode setting process of step #27 is performed according to the flowchart of FIG. 16.

Specifically, in the case where the high-speed mode is set in FIG. 16, the parameter for the selective read operation described above is read from a control data ROM (#151, #152). The position and size of the read range ARh described above are also read in this step. In the case where the normal mode is set, on the other hand, the parameter for the read operation in normal mode is read from the control data ROM (#151, #153). The remainder is the same as in the case of high-speed mode.

Incidentally, the scan range of the slit light is such that the angle corresponding to the upper end of the read ranges ARh, ARn is assumed to be a start angle, and the angle corresponding to the lower end of the read ranges ARh, ARn is assumed to be an ending angle. Also, the scan rate of the slit light is set based on the read time per frame. In other words, for high speed mode when the read time is short, the scan rate of the slit light is correspondingly high. As a result, the scan on one screen Q (i.e. the measurement time) is shortened. A similar effect is produced simply by increasing the scan rate while the scan range is kept in normal mode.

As described above, according to the fourth embodiment, the wasteful read operation of the image sensing device can be reduced, whereby the time required for three-dimensional input can be shortened while at the same time reducing the data processing burden. Also, the user can select the number of sampling points (resolution) in accordance with the intended application.

In each of the embodiments described above, the whole or partial configuration, the contents or sequence of the process or timing of a specific process of the three-dimensional camera 2, the host 3 or the measuring system 1 can be appropriately modified without departing from the spirit of the invention.

What is claimed is:

1. A three-dimensional input apparatus comprising:
   a projector for irradiating a detection light beam on an object;
   a scanning mechanism for scanning said object by deflecting the direction of irradiation of said detection light beam;
   an image sensing device with an image sensing surface including a plurality of two-dimensionally arranged light-receiving elements, for receiving the detection light beam reflected on said object; and
   a controller for controlling an electric charge accumulation time of said plurality of light-receiving elements such that the scanning mechanism moves the detection light beam for each sampling period and a plurality of types of outputs with different electric charge accumulation times are produced by each of said light-receiving elements in one light-receiving area for each sampling period, discriminating whether at least one of said plurality of types of output signals is saturated for each one of the two-dimensionally arranged light-receiving elements or for each part of the two-dimensionally arranged light-receiving elements, and selecting non-saturated signals among said plurality of types of output signals for each one of the plurality of two-dimensionally arranged light-receiving elements or for each part of the plurality of two-dimensionally arranged light-receiving elements, based on the result of the discrimination,
   wherein the controller controls said image sensing device so as to output a signal corresponding to the accumulated electric charge upon lapse of a first accumulation time and continue to accumulate electric charge while maintaining said accumulated electric charge until a second charge accumulation time, and
   wherein the controller outputs a signal by multiplying an output value during a first accumulation time by a multiple derived from a ratio between accumulation times.

2. An apparatus according to claim 1,
   wherein said controller selects among said non-saturated signals one having a long electric charge accumulation time.

3. A three-dimensional input apparatus comprising: a projector for irradiating a detection light beam on an object;
   a scanning mechanism for scanning said object by deflecting the direction of irradiation of said detection light beam;
   an image sensing device having an image sensing surface including a plurality of two-dimensionally arranged light-receiving elements for receiving the detection light beam reflected on said object;
   a controller for controlling said image sensing device so as to output a first signal due to a first electric charge accumulation time and a second signal due to a second electric charge accumulation time equal to a predetermined multiple of said first signal during the electric charge accumulation of said image sensing device;
   a selecting circuit for selecting said second signal in the case where said second signal has not been saturated and selecting a signal of a size equal to said predetermined multiple of said first signal in the case where said second signal has been saturated; and
   a processor for performing calculations using the selected signal, said selecting circuit including:
   a first switch, a second switch, a memory, a comparator, and an integrator, wherein
   said first switch receives the first and second signals, outputs the first signal to the memory and outputs the second signal to the second switch and to the comparator,
   the integrator receives the first signal from the memory and outputs the signal of a size equal to said predetermined multiple of said first signal to the second switch, and
   the comparator compares the second signal to a reference saturation level and outputs a control signal to the second switch to output the second signal where the second signal has not been saturated, and to output the signal of a size equal to said predetermined multiple where the second signal has been saturated.

4. A three-dimensional input method for irradiating an object using a three-dimensional input apparatus, wherein the apparatus includes a projector, a scanning mechanism, an image sensing device with an image sensing surface including a plurality of two-dimensionally arranged light-receiving elements, and a controller, the method comprising:
   irradiating a detection light beam on the object;
   scanning said object by deflecting the direction of irradiation of said detection light beam;
   controlling an electric charge accumulation time of said plurality of light-receiving elements such that the scanning mechanism moves the detection light beam for each sampling period and a plurality of types of outputs with different electric charge accumulation times are produced by each of said light-receiving elements in one light-receiving area for each sampling period, discriminating whether at least one of said plurality of types of output signals is saturated for each one of the two-dimensionally arranged light-receiving elements or for each part of the two-dimensionally arranged light-receiving elements;
   selecting non-saturated signals among said plurality of types of output signals for each one of the plurality of two-dimensionally arranged light-receiving elements or for each part of the plurality of two-dimensionally arranged light-receiving elements, based on the result of the discrimination;
   controlling the image sensing device so as to output a signal corresponding to the accumulated electric charge upon lapse of a first accumulation time and continue to accumulate electric charge while maintaining said accumulated electric charge until a second charge accumulation time; and
   outputting a signal by multiplying an output value during a first accumulation time by a multiple derived from a ratio between accumulation times.

5. A method according to claim 4, wherein said selection of the non-saturated signals is carried out so that non-saturated signals having a long electric charge accumulation time are selected.

* * * * *